US006821759B1

(12) United States Patent
Heintz et al.

(10) Patent No.: US 6,821,759 B1
(45) Date of Patent: Nov. 23, 2004

(54) METHODS OF PERFORMING HOMOLOGOUS RECOMBINATION BASED MODIFICATION OF NUCLEIC ACIDS IN RECOMBINATION DEFICIENT CELLS AND USE OF THE MODIFIED NUCLEIC ACID PRODUCTS THEREOF

(75) Inventors: Nathaniel Heintz, Pelham Manor, NY (US); Peter Model, New York, NY (US); Xiangdong W. Yang, New York, NY (US); Shiaoching Gong, New York, NY (US)

(73) Assignee: The Rockefeller University, New York, NY (US)

( * ) Notice: Subject to any disclaimer, the term of this patent is extended or adjusted under 35 U.S.C. 154(b) by 323 days.

(21) Appl. No.: 09/619,364

(22) Filed: Jul. 19, 2000

Related U.S. Application Data

(63) Continuation-in-part of application No. 09/356,987, filed on Jul. 20, 1999, now abandoned, which is a continuation-in-part of application No. 09/102,490, filed on Jun. 22, 1998, now abandoned.
(60) Provisional application No. 60/050,535, filed on Jun. 23, 1997.

(51) Int. Cl.[7] .................. C12N 15/64; C12N 15/66; C12N 15/00; C12N 15/09; C07H 21/04

(52) U.S. Cl. .................. 435/91.4; 435/6; 435/29; 435/235.1; 435/252.3; 435/320.1; 435/91.41; 435/91.42; 435/325; 435/455; 435/468; 435/471; 536/23.1

(58) Field of Search .................. 435/6, 29, 320.1, 435/235.1, 325, 440, 91.4, 91.41, 91.42, 455, 468, 471, 252.3; 536/23.1

(56) References Cited

U.S. PATENT DOCUMENTS

| 5,851,808 A | | 12/1998 | Elledge et al. | |
|---|---|---|---|---|
| 6,069,010 A | | 5/2000 | Choi | |
| 6,130,090 A | * | 10/2000 | Heintz et al. | 435/466 |
| 6,143,566 A | * | 11/2000 | Heintz et al. | 435/463 |

FOREIGN PATENT DOCUMENTS

| EP | 485701 A1 | 5/1992 |
|---|---|---|
| WO | WO 97/10343 | 3/1997 |
| WO | WO 98/59060 | 12/1998 |
| WO | WO 99/29837 | 6/1999 |

OTHER PUBLICATIONS

U.S. patent application Ser. No. 09/356,987, Heintz et al., filed Jul. 20, 1999.
U.S. patent application Ser. No. 09/102,490, Heintz et al., filed Jun. 22, 1998.
U.S. Provisional application No. 60/050,535, Heintz et al., filed Jun. 23, 1997.

Baker & Cotten, Nucleic Acids Research 25:1950–56 (1997).
Balasubramanian et al., *J. of Bacteriology* 178:273–279 (1996).
Birnboim et al., *Nucleic Acids Res.* 7:1513–1523 (1979.
Bochner et al., *J. Bacteriol.* 143:926–33 (1980).
Boren et al., Genome Research, 6:1123–30 (1996).
Boysen et al., *Genome Research*, 7:330–338 (1997).
Bradley et al., *Nature Genet.* 14:121–3 (1997).
Brinster et al. (1989) *Proc.Natl.Acad.Sci.* 86:7087–91.
Brinster et al., *Proc.Natl.Acad.Sci.* 85:836–840 (1988).
Burke et al., *Science* 236:806–12.
Chatterjee & Cohen, Nucleic Acids Research 25:2205–2212 (1997).
Chatterjee et al., Elsevier Science 13:33–42 (1996).
Cibelli et al., Nature Biotechnology, 16:642–646 (1998).
Clark et al., *Critical Reviews in Microbiology* 20:125–142 (1994).
Deng and Capecchi (*MCB*, 12:3365–3371).
Dillon et al., *Trends Genet.* 9:134–7 (1993).
Eggleston & West, Trends Genet. 12:20–25 (1996).
Fujitani et al. (1995) Genetics 140:797–809.
Gnirke et al. (1993) Genomics 15:659–67.
Hamilton et al., *J. Bacteriol.* 171:4617–22 (1989).
Harrington et al. *Nature Genetics*, 15:345–355 (1997).
Hashimoto–Gotoh et al. (1977) J. Bacteriol. 131:405–12.
Hosoda et al., *Nucleic Acids Res.* 18:3863–9 (1990).
Ioannou et al., *Nat. Genet.*, 6:84–89 (1994).
Jaenisch et al., *Science* 240:1468–74 (1985).
Joyner, A., Ed. *Gene Targeting, a practical approach*, IRL Press.
Kennison, *Trends Genet.* 9:75–9 (1993).
Kim et al., *MCB*, 12:3636–3643 (1992).
Kim et al., Genomics 34:213–18 (1996).
Kim et al., *Proc.Natl.Acad.Sci.* 93:6297–6301 (1996).
Kuhn et al., *Science* 269:1427–9 (1995).
Larionov et al., Nucleic Acids Research 22:4154–4161 (1994).
Maloy et al., *Bacteriol.* 145:1110 (1981).
McKee et al., *Chromosoma* 7:479–488 (1996).
Mejia et al., *Genome Res.* 7:179–186 (1997).
Monaco et al., *Trends Biotechnol* 12:280–286 (1994).
O'Connor et al. *Science,* 244:1307–1312 (1989).
Pain et al., Cells Tissues Organs, 165:212–219 (1999).
Palmiter et al., *Cell* 41:343–5 (1985).

(List continued on next page.)

*Primary Examiner*—Gerry Leffers

(57) ABSTRACT

A simple method for modifying genes in a recombination deficient host cell is disclosed. Such modifications include generating insertions, deletions, substitutions, and/or point mutations at any chosen site in the independent origin based cloning vector. The modified gene is contained in an independent origin based cloning vector that is used to introduce a modified heterologous gene into a cell. Such a modified vector may be used in the production of a germline transmitted transgenic animal, or in gene targeting protocols in eukaryotic cells. In particular, high throughput methodology is provided for generating the modified the independent origin based cloning vectors of the present invention.

17 Claims, 23 Drawing Sheets

OTHER PUBLICATIONS

Peakman et al., *Proc.Natl.Acad.Sci.* 93:10222–10227 (1996).
Perrimon, Proc. Natl. Acad. Sci., 95:9716–9717 (1998).
Peterson et al., *TIG (Trends Genet.)* 13:61–66 (1997).
Reiss et al.,*Proc.Natl.Acad.Sci.* 93:3094–3098 (1996).
Rorth, Development, 125:1049–1057 (1998).
Rorth, Proc. Natl. Acad. Sci., 93:12418–12422 (1996).
Shizuya et al., Proc. Natl. Acad. Sci. 89:8794–8797 (1992).
Simon, Nature Biotech 15:839 (1997).
Spencer et al. (1993) Meth.: Comp. Meth. Enzymol. 5:161–75.
Tsien et al., *Cell* 87:1317–26 (1996).
Wang et al., *Genomics* 24:527–34 (1994).
Wilson et al., *Annu.Rev.Cell.Biol.* 6:679–714 (1990).
Woo et al., *Nucleic Acids Res.,* 22:4922–31 (1994).
Wooster et al., *Nature* 378:789–92 (1995).
Yang et al., *Development* 122:555–66 (1996).
Yang et al., Nature Biotech. 15:859–65 (1997).
Yoon et al., Genetic Analysis: Biomolec. Engineering, 14: 89–95 (1998).
Zhang et al., Nature Genetics, 20(2):123–8, (1998).

\* cited by examiner

FIG. 1
I Construction of the recA(+) and temperature sensitive shuttle vector
1) Clone two small genomic fragments (> 500 bp each) into the building vector (pBV1)
2) Transfer the recombination cassette into the Ts-RecA(+) shuttle vector (pSV1.RecA)
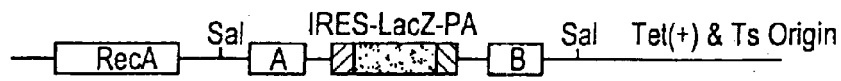
II. Transformation of the shuttle vector into the E.Coli host strain of BACs and selection for co-integrates
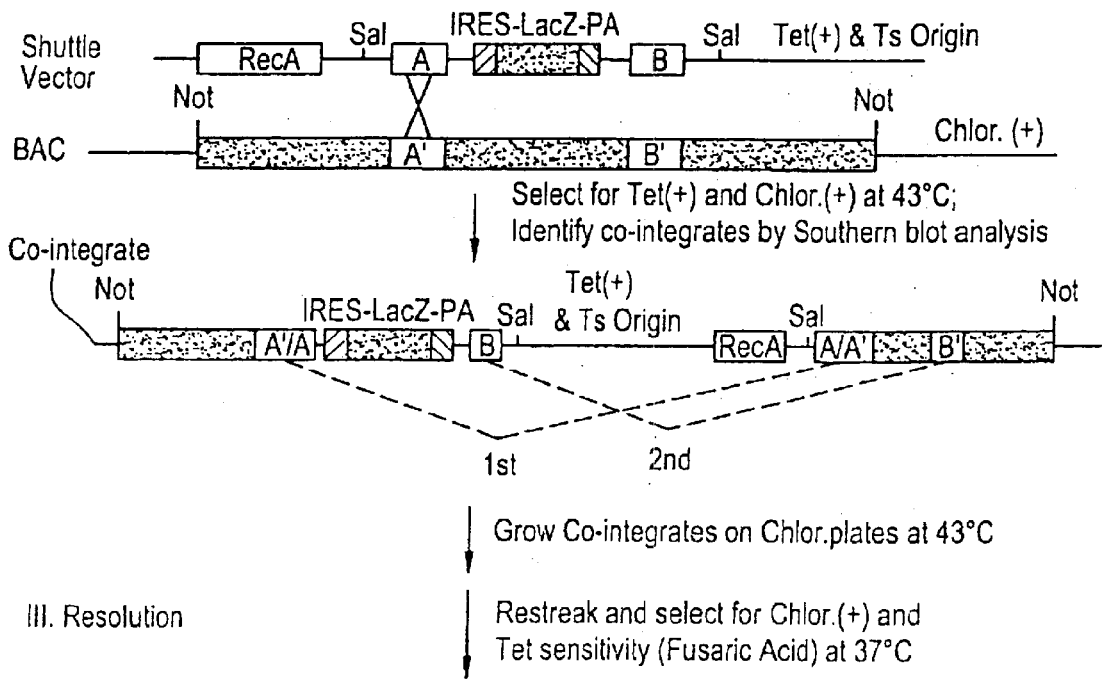
III. Resolution
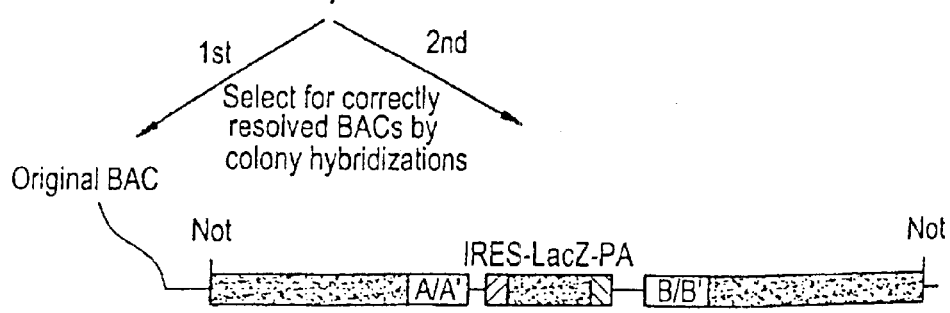

Map of the RU49 Genomic Locus within BAC169

Map of the Modifified BAC 169 with an IRES-LacZ-PolyA Insertion

FIG. 7A
Hypothetical map of a gene of interest within a selected BAC (>150kb insert size)

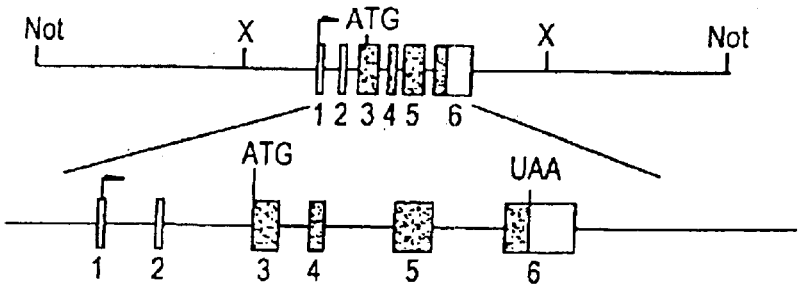

FIG. 7B
First targeted modification to introduce the positive selection marker gene

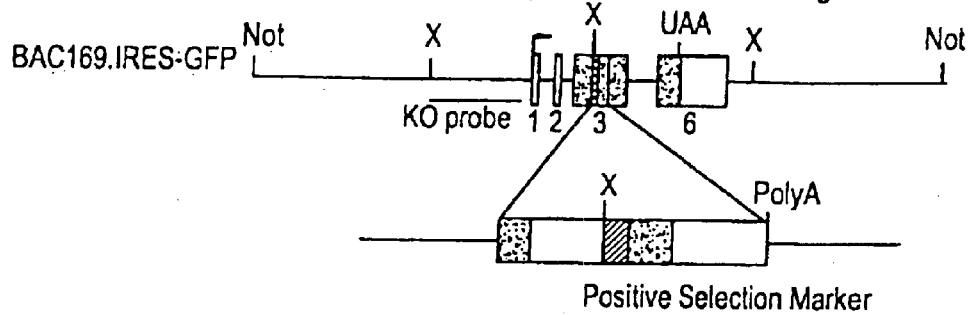

ES Cells Targeting: Marker gene=PGK-Neo-PA
Transgenic knock-out: Marker gene=IRES-EGFP-1 or IRES-LacZ

FIG. 7C
Second Modification to delete the promoter of the gene and to generate the short arm

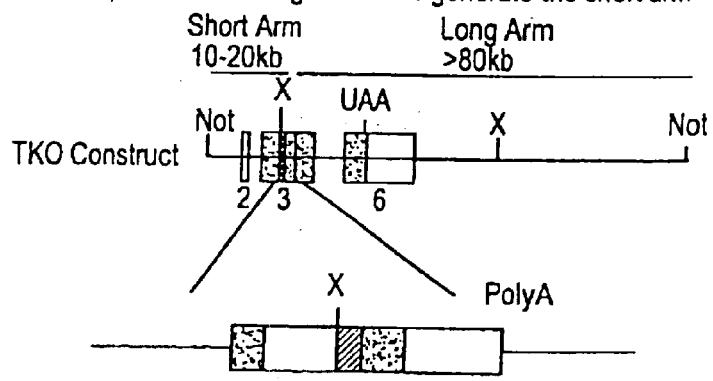

Selection of positive clones by Southern blots:
Digest DNA with enzyme X and probed with the KO probe
  Endogenous allele: >50kb
  Target allele: <20kb A
Intraculminate Fissure (ICF)
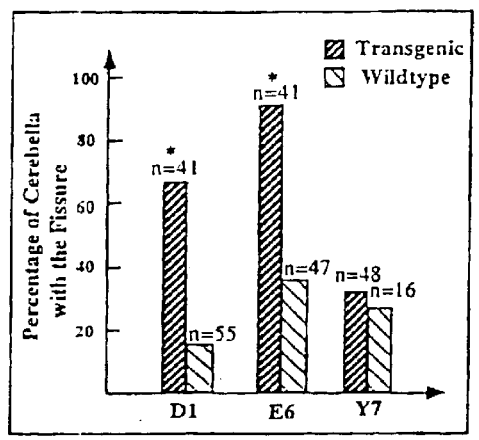
B
Crus I Fissure (CrI F)
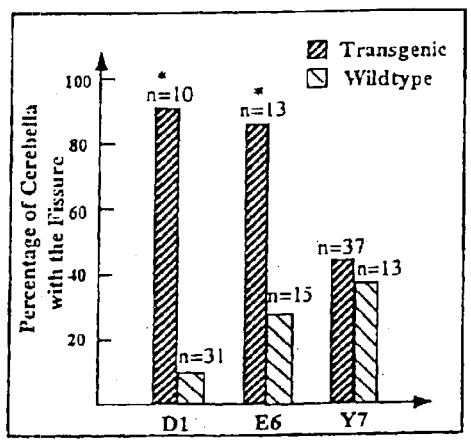
C
Crus II Fissure (CrIIF)
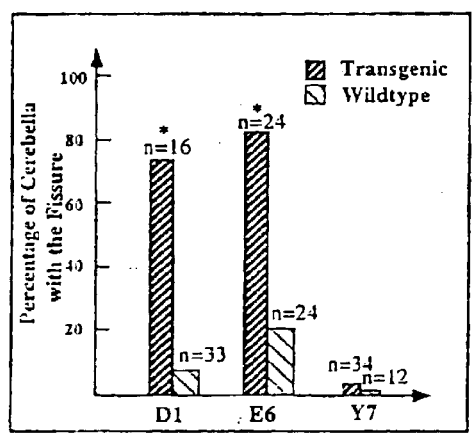
D
Paramedian Lobule Fissure (PMDF)
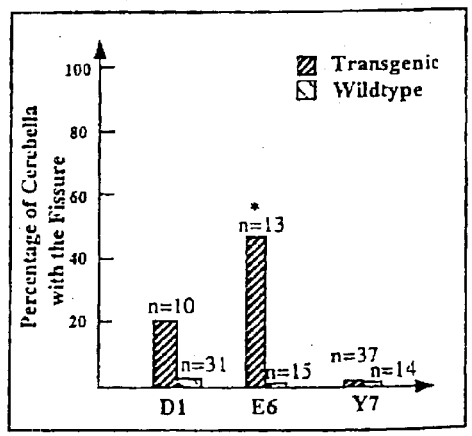
Figure 18

METHODS OF PERFORMING HOMOLOGOUS RECOMBINATION BASED MODIFICATION OF NUCLEIC ACIDS IN RECOMBINATION DEFICIENT CELLS AND USE OF THE MODIFIED NUCLEIC ACID PRODUCTS THEREOF

CROSS-REFERENCE TO RELATED APPLICATIONS

The present application is a Continuation-In-Part of copending U.S. Ser. No. 09/356,987 filed Jul. 20, 1999, now abandoned, which is a Continuation-In-Part of U.S. Ser. No. 09/102,490 filed Jun. 22, 1998 now abandoned which is a non-provisional application claiming the priority of provisional U.S. Ser. No. 60/050,535 filed Jun. 23, 1997, the disclosures of which are hereby incorporated by reference in their entireties. Applicants claim the benefits of these applications under 35 U.S.C. §§119(e) and 120.

GOVERNMENTAL SUPPORT

The research leading to the present invention was supported, at least in part, by a grant from the National Science Foundation Grant No. MCB-9316625, by NINDS PHS 30532, and NIH MSTP grant GM07739. Accordingly, the Government may have certain rights in the invention.

FIELD OF THE INVENTION

This invention relates generally to methods of modifying genes with specificity in recombination deficient cells by transiently enabling homologous recombination in the cells. Included in the invention are conditional replication shuttle vectors which bestow transient recombination capabilities to an otherwise recombination deficient cell. The independent origin based cloning vectors containing the modified genes and methods of using the independent origin based cloning vectors containing the modified genes are also included in the present invention. In particular, high throughput methodology is provided for generating the modified the independent origin based cloning vectors.

BACKGROUND OF THE INVENTION

Functional analyses of genes in vivo frequently involve the introduction of modified genomic DNA into the germline to generate transgenic animals [Jaenisch et al., Science 240:1468 (1985); Brinster, Cell 41:343 (1985)]. The genomic DNA sequences containing introns and essential regulatory sequences have been shown to be expressed in vivo in cases where simple cDNA constructs cannot be expressed [Brinster et al., Proc.Natl.Acad.Sci. 85:836–840 (1988)]. Furthermore, the size of the genomic DNA that can be readily manipulated in vitro and introduced into the germline can be a critical determinant of the outcome of the functional analysis of a gene since elements that are important for high level, tissue specific and position-independent expression of the transgene may be located at a long distance from the gene itself [Dillon et al., Trends Genet. 9:134 (1993); Kennison, Trends Genet. 9:75 (1993); Wilson et al., Annu.Rev. Cell.Biol. 6:679 (1990)].

On the other hand, the use of such large genomic transgenes has several practical problems. For example, the size of the transgene is presently limited due to constraints on the sequence length that can be cloned and stably maintained in a conventional plasmid or a cosmid. Thus DNA sequences suspected of being nonessential are often omitted when designing the constructs to be transferred because of the size limitation. In addition, in vitro manipulations of large DNAs oftentimes lead to mechanical shear [Peterson et al., TIG 13:61–66].

Yeast artificial chromosomes (YACs) allow large genomic DNA to be modified and used for generating transgenic animals [Burke et al., Science 236:806; Peterson et al., Trends Genet. 13:61 (1997); Choi, et al., Nat. Genet., 4:117–223 (1993), Davies, et al., Biotechnology 11:911–914 (1993), Matsuura, et al., Hum. Mol. Genet., 5:451–459 (1996), Peterson et al., Proc. Natl. Acad. Sci., 93:6605–6609 (1996); and Schedl, et al., Cell, 86:71–82 (1996)]. Other vectors also have been developed for the cloning of large segments of mammalian DNA, including cosmids, and bacteriophage P1 [Sternberg et al., Proc. Natl. Acad. Sci. U.S.A., 87:103–107 (1990)]. YACs have certain advantages over these alternative large capacity cloning vectors [Burke et al., Science, 236:806–812 (1987)]. The maximum insert size is 35–30 kb for cosmids, and 100 kb for bacteriophage P1, both of which are much smaller than the maximal insert for a YAC. However, there are several critical limitations in the YAC system including difficulties in manipulating YAC DNA, chimerism and clonal instability [Green et al., Genomics, 11:658 (1991); Kouprina et al., Genomics 21:7 (1994); Larionov et al., Nature Genet. 6:84 (1994)]. As a result, generating transgenic mice with an intact YAC remains a challenging task [Burke et al., Science 236:806; Peterson et al., Trends Genet. 13:61 (1997)].

An alternative to YACs are E. coli based cloning systems based on the E. coli fertility factor that have been developed to construct large genomic DNA insert libraries. They are bacterial artificial chromosomes (BACs) and P-1 derived artificial chromosomes (PACs) [Mejia et al., Genome Res. 7:179–186 (1997); Shizuya et al., Proc. Natl. Acad. Sci. 89:8794–8797 (1992);Ioannou et al., Nat. Genet., 6:84–89 (1994); Hosoda et al., Nucleic Acids Res. 18:3863 (1990)]. BACs are based on the E. coli fertility plasmid (F factor); and PACs are based on the bacteriophage P1. The size of DNA fragments from eukaryotic genomes that can be stably cloned in Escherichia coli as plasmid molecules has been expanded by the advent of PACs and BACs. These vectors propagate at a very low copy number (1–2 per cell) enabling genomic inserts up to 300 kb in size to be stably maintained in recombination deficient hosts (most clones in human genomic libraries fall within the 100–200 kb size range). The host cell is required to be recombination deficient to ensure that non-specific and potentially deleterious recombination events are kept to a very minimum. As a result, libraries of PACs and BACs are relatively free of the high proportion of chimeric or rearranged clones typical in YAC libraries, [Monaco et al., Trends Biotechnol 12:280–286 (1994); Boyseu et al., Genome Research, 7:330–338 (1997)]. In addition, isolating and sequencing DNA from PACs or BACs involves simpler procedures than for YACs, and PACs and BACs have a higher cloning efficiency than YACs [Shizuya et al., Proc. Natl. Acad. Sci. 89:8794–8797 (1992);Ioannou et al., Nat. Genet., 6:84–89 (1994); Hosoda et al., Nucleic Acids Res. 18:3863 (1990)]. Such advantages have made BACs and PACs important tools for physical mapping in many genomes [Woo et al., Nucleic Acids Res., 22:4922 (1994); Kim et al., Proc.Natl.Acad.Sci. 93:6297–6301 (1996); Wang et al., Genomics 24:527 (1994); Wooster et al., Nature 378:789 (1995)]. Furthermore, the PACs and BACs are circular DNA molecules that are readily isolated from the host genomic background by classical alkaline lysis [Bimboim et al., Nucleic Acids Res. 7:1513–1523 (1979].

Functional characterization of a gene of interest contained by a PAC or BAC clone generally entails transferring the DNA into a eukaryotic cell for transient or long-term expression. A transfection reporter gene, e.g. a gene encoding lacZ, together with a selectable marker, e.g., neo, can be inserted into a BAC [Mejia et al., *Genome Res.* 7:179–186 (1997)]. Transfected cells can be then detected by staining for X-Gal to verify DNA uptake. Stably transformed cells are selected for by the antibiotic G418.

However, while PACs and BACs have cloning capacities up to 350 kb, performing homologous recombination to introduce mutations into a gene of interest has not been demonstrated [Peterson et al., *TIG* 13:61–66]. Indeed, although BACs or PACs have become an important source of large genomic DNA in genome research, there are still no methods available to modify the BACs or PACs. Furthermore, no germline transmission of intact BACs or PACs in transgenic mice have been reported. These, as well as other disadvantages of BACs and PACs greatly limit their potential use for functional studies. Therefore, there is a need for an improved cloning vector for germline transmission of selected genes in transgenic animals. More particularly there is a need for a cloning vector that has the capacity to contain greater than 100 kilobases of DNA, which can be readily manipulated and isolated, but still can be stably stored in libraries relatively free of rearranged clones. In addition, there is a need to provide methodology for generating such cloning vectors. There is also a need to apply such vectors to improve the results of the methods of gene transfer used in gene targeting, for creating animal models for diseases due to a dominant mutated allele, e.g., Huntington's disease, and for overexpressing in vivo proteins encoded by genes having an unknown function in order to determine the biological role of such genes.

Gene targeting has been used in various systems, from yeast to mice, to make site specific mutations in the genome. Gene targeting is not only useful for studying function of proteins in vivo, but it is also useful for creating animal models for human diseases, and in gene therapy. The technique involves the homologous recombination between DNA introduced into a cell and the endogenous chromosomal DNA of the cell. However, in the vertebrate system, the rate of homologous recombination is very low, as compared to random integration. The only cell line that allows a relatively high homologous recombination rate and maintains the ability to populate the germline is the murine 129 embryonic stem cells (ES cells). Using this specialized cell, mice can be generated with a targeted mutation [Joyner, A. L., *Gene Targeting: A Practical Approach. The Practical Approach Series* (Rickwood, D., and Hames, B. D., Eds.), IRL Press, Oxford (1993)]. However, the rate of homologous recombination for some gene loci in ES cells is still extremely low (<1%), the procedure is labor intensive, and the cost of generating targeted mutant mice is very expensive. Moreover, since there are no ES cells available for vertebrates other than mice, gene targeting in a germline is still not possible for other vertebrates.

A major limitation for gene transfer procedures in vertebrate cells such as gene targeting is the low targeting frequency. One critical factor affecting the targeting frequency is the total length of homology. Deng and Capecchi [*MCB*, 12:3365–3371 (1992)] have shown that gene targeting frequency is linearly-dependent on the logarithm of the total homology length over homology lengths of 2.8 kb to 14.6 kb. Since the curve did not plateau at the 14.6 kb homology, it is likely that incorporating greater homology lengths into the targeting vector will further increase the homologous recombination rate. Using a mathematical model developed by Fujitani et al, [*Genetics*, 140:797–809, (1995)], an estimate can be made that with a total homology of 100 kb isogenous DNA (i.e., DNA from the same strain of mice), the gene targeting rate in ES cells would be 10%. This is a dramatic improvement over the conventional 14.6 kb targeting vector, which only yields a corresponding rate of only 0.03%. Further support for the present strategy i.e., using a large DNA construct for gene targeting rate comes from an experiment with *Mycobacterium tuberculosis*, the causal agent of tuberculosis. Like vertebrate cells, gene targeting in TB has a very low rate, mainly due to the predominance of random integration over homologous recombination. It has been demonstrated that using a 40–50 kb linear targeting construct, a 6% targeting frequency could be obtained, whereas no targeting event was obtained at all with a smaller (<10 kb) targeting construct [Balasubramanian et al., *J. of Bacteriology* 178:273–279 (1996)]. Therefore, there is a need to construct large gene transfer constructs to allow efficient gene transfer in many biological systems.

The citation of any reference herein should not be construed as an admission that such reference is available as "Prior Art" to the instant application.

SUMMARY OF THE INVENTION

The present invention provides a novel and efficient method of modifying independent origin based cloning vectors for in vitro and in vivo gene expression. In its broadest embodiment, the present invention provides a method of selectively performing homologous recombination on a particular nucleotide sequence contained in a recombination deficient host cell, i.e., a cell that cannot independently support homologous recombination. The method can employ a recombination cassette which contains a nucleic acid that selectively integrates into the particular nucleotide sequence when the recombination deficient host cell is induced to support homologous recombination. The method comprises introducing the recombination cassette into the recombination deficient host cell, and inducing the recombinantly deficient host cell to transiently support homologous recombination, thereby allowing the nucleic acid to integrate into the particular nucleotide sequence. In a preferred embodiment, unselected nucleotide sequence rearrangements and deletions, which are characteristic of host cells that support homologous recombination, are not evident with restriction endonuclease digestion map analysis with a restriction enzyme such as HindIII, EcoRI, XhoI, or AvrII. In a more preferred embodiment, unselected nucleotide sequence rearrangements and deletions are not evident with restriction endonuclease digestion map analysis with two or more restriction enzymes. In an important aspect of the present invention a high throughput methodology is provided for generating modified independent origin based cloning vectors e.g., BACs that comprise genomic DNA.

In a particular aspect of the present invention, the recombination deficient host cell cannot independently support homologous recombination because the host cell is RecA. In this aspect of the invention, inducing the host cell to transiently support homologous recombination comprises inducing the transient expression of a RecA-like protein in the host cell. In a preferred embodiment, inducing the transient expression of the RecA-like protein can be performed with a conditional replication shuttle vector. In a more preferred embodiment the conditional replication shuttle vector is a temperature sensitive shuttle vector (TSSV) that replicates at a permissive temperature, but does not replicate at a non-permissive temperature.

In one particular embodiment of this type, inducing the transient expression of the RecA-like protein comprises transforming the host cell with the TSSV at a permissive temperature, and growing the host cell at a non-permissive temperature. The TSSV encodes a RecA-like protein that is expressed in the host cell and supports the homologous recombination between a nucleic acid contained in a recombination cassette and the particular nucleotide sequence contained in the host cell. The TSSV encoding the RecA-like protein is diluted out when the host cell is grown at the non-permissive temperature. In one particular embodiment of this type the permissive temperature is 30° C. and the non-permissive temperature is 43° C.

In a more intricate version of the present invention, the particular nucleotide sequence which has been selected to undergo homologous recombination is contained in an independent origin based cloning vector (IOBCV) that is comprised by the host cell, and neither the independent origin based cloning vector alone, nor the independent origin based cloning vector in combination with the host cell, can independently support homologous recombination. In a particular embodiment of this type both the independent origin based cloning vector and the host cell are RecA⁻, and inducing the host cell to transiently support homologous recombination comprises inducing the transient expression of the RecA-like protein to support homologous recombination in the host cell. In one particular embodiment the independent origin based cloning vector is a Bacterial or Bacteriophage-Derived Artificial Chromosome (BBPAC) and the host cell is a host bacterium. In a preferred embodiment, inducing the transient expression of the RecA-like protein is performed with a conditional replication shuttle vector that encodes the RecA-like protein.

In one such embodiment the conditional replication shuttle vector contains an origin of DNA replication that requires the expression of a specific protein or proteins for replication that is (are) not normally present in host bacteria. In a particular embodiment of this type, the origin of DNA replication is the R6Kγ DNA replication origin [oriR (R6Kγ)] and the specific protein that is expressed by the specific host cell is the pi replication protein which is encoded by the pir gene.

In another such embodiment the conditional replication shuttle vector is a temperature sensitive shuttle vector (TSSV) that replicates at a permissive temperature, but does not replicate at a non-permissive temperature. In one particular embodiment of this type the permissive temperature is 30° C. and the non-permissive temperature is 43° C. In another such embodiment the RecA-like protein is controlled by an inducible promoter and the transient expression of the RecA-like protein is achieved by the transient induction of the inducible promoter in the host cell. In another embodiment, the RecA-like protein is controlled by a constitutive promoter with the transient expression induced by the TSSV.

In a preferred embodiment the conditional replication shuttle vector contains a TSSV that also comprises a recombination cassette and a first gene which bestows resistance to a host cell that contains the TSSV against a first toxic agent. In addition, the first gene can be counter-selected against. The recombination cassette, the RecA-like protein gene, and the first gene are linked together on the TSSV such that when the nucleic acid integrates (i.e. resolved) into the particular nucleotide sequence, the RecA-like protein gene and the first gene remain linked together, and neither the RecA-like protein gene nor the first gene remain linked to the integrated nucleic acid. In a particular embodiment of this type, the independent origin based cloning vector is a BBPAC and the host cell is a bacterium. The BBPAC further contains a second gene that bestows resistance to the host cells against a second toxic agent. Introducing the recombination cassette into the host cells is performed by transforming the host cell with the TSSV. Inducing the transient expression of the RecA-like protein to support homologous recombination comprises: (i) incubating the host cells at a permissive temperature in the presence of the first toxic agent and the second toxic agent, wherein transformed host cells containing the TSSV and the BBPAC are selected for and wherein the RecA-like protein is expressed. A first homologous recombination event occurs between the recombination cassette and the particular nucleotide sequence forming a co-integrate between the TSSV and the BBPAC, wherein the TSSV is either free or part of a co-integrate; (ii) incubating the transformed host cells at a non-permissive temperature in the presence of the first toxic agent and the second toxic agent, wherein host cells containing a TSSV co-integrate are selected for, and wherein free TSSV cannot replicate; (iii) selecting a host cell containing a co-integrate between the TSSV and the BBPAC by Southern analysis; (iv) incubating the host cells containing a co-integrate between the TSSV and the BBPAC at a non-permissive temperature in the presence of the second toxic agent, wherein a second homologous recombination event occurs between the recombination cassette and the particular nucleotide sequence, therein integrating the nucleic acid into the particular nucleotide sequence and forming a resolved host cell, i.e., a host cell containing a resolved BBPAC; and (v) incubating the host cells containing the resolved BBPAC in the presence of the second toxic agent, and a counter-selecting agent, and wherein the counter-selecting agent is toxic to host cells containing the first gene, and wherein host cells containing the RecA-like protein gene are removed. Another embodiment further comprises selecting a host cell containing the resolved BBPAC by colony hybridization with a labeled probe that binds to a DNA homologue of the nucleic acid, an mRNA homologue of the nucleic acid, and/or a protein encoded by the nucleic acid. In a particular embodiment, the permissive temperature is 30° C., the non-permissive temperature is 43° C. In a preferred embodiment the incubating of host cells containing the resolved BBPAC in the presence of the second toxic agent and counter-selecting agent is performed at 37° C. Preferred embodiments further comprise the generating of the recombination cassette by placing a first genomic fragment 5' of the specific nucleic acid that is to selectively integrate into the particular nucleotide sequence, and placing a second genomic fragment 3' of the specific nucleic acid. The first genomic fragment corresponds to a region of the particular nucleotide sequence that is 5' to the region of the particular nucleotide sequence that corresponds to the second genomic fragment. Thus, both the first genomic fragment and the second genomic fragment contain portions of the particular nucleotide sequence. In one such embodiment, both the first genomic fragment and the second genomic fragment contain 250 or more basepairs of the particular nucleotide sequence. In a preferred embodiment, the first and second genomic fragments are about the same size. In another embodiment, both the first genomic fragment and the second genomic fragment contain 500 or more basepairs of the particular nucleotide sequence. In still another embodiment, both the first genomic fragment and the second genomic fragment contain 1000 or more basepairs of the particular nucleotide sequence. In one particular embodiment the recombination cassette is generated in a building vector and the recombination cassette is subsequently transferred to the TSSV.

In a particular embodiment the first gene confers tetracycline resistance and the counter-selecting agent is fusaric acid. In a preferred embodiment the RecA-like protein is recA. In the more preferred embodiment the TSSV is pSV1.RecA having the ATCC no. 97968.

In a related aspect of the present invention the RecA-like protein is controlled by an inducible promoter, and the transient expression of the RecA-like protein is achieved by the transient induction of the inducible promoter in the host cell. In one embodiment of this type, the independent origin based cloning vector is a BBPAC and the recombination deficient host cell is an *E. coli* bacterium. In a preferred embodiment the RecA-like protein is recA.

The present invention also provides a conditional replication shuttle vector that encodes a RecA-like protein. In one such embodiment the RecA-like protein is controlled by an inducible promoter. In a preferred embodiment the conditional replication shuttle vector is a temperature sensitive shuttle vector (TSSV). The RecA-like protein of the TSSV can be controlled by either a constitutive promoter or by an inducible promoter. In another embodiment the conditional replication shuttle vector contains an origin of DNA replication that requires the expression of a specific protein or proteins for replication that is (are) not normally present in host bacteria but is (are) in a specific host cell.

In one embodiment the conditional replication shuttle vector contains a gene that can be counter-selected against. In a specific embodiment of this type the conditional replication shuttle vector contains a gene that confers tetracycline resistance. In another embodiment the conditional replication shuttle vector contains a RecA-like protein that is recA. In still another embodiment the conditional replication shuttle vector contains both a gene that confers tetracycline resistance and a RecA-like protein that is recA. In a preferred embodiment the conditional replication shuttle vector is a TSSV. In a more preferred embodiment the TSSV is pSV1.RecA having the ATCC no. 97968.

The present invention further provides conditional replication shuttle vectors that comprise an R6Kγ origin of replication and a nucleic acid encoding a recombination protein. In a preferred embodiment the recombination protein is recA. Preferably, the conditional replication shuttle vector is constructed so that it can modify a gene of interest in an IOBCV, preferably a BBPAC, and more preferably a BAC through homologous recombination. Such modifications include insertions, substitutions, and/or deletions. In a particular embodiment, the conditional replication shuttle vector further comprises a nucleic acid encoding one or more marker proteins or peptides that are to be inserted into the IOBCV so a particular gene product (encoded by the IOBCV) can be identified and/or monitored. In one such embodiment, the nucleic acid encodes the marker protein IRES-EGFP. In another embodiment, the nucleic acid encodes the marker FLAG peptide. In still another embodiment, the nucleic acid is taulacZ. In yet another embodiment, the nucleic acid is lacZ. As indicated above and exemplified below, multiple maker proteins/peptides can be encoded in the conditional replication shuttle vectors of the present invention and subsequently inserted into/or adjacent to the protein encodeded by the genc of interest.

In a preferred embodiment the conditional replication shuttle vector further comprises a gene that can be counter-selected against. In a preferred embodiment of this type, the gene that can be counter-selected against is SacB. In another embodiment, the gene that can be counter-selected against confers tetracycline resistance.

In one embodiment the conditional replication shuttle vector further comprises an A box region that either comprises or can be constructed to comprise a nucleic acid that can selectively integrate into a particular nucleotide sequence of a gene of interest contained by an IOBCV when the IOBCV and the conditional replication shuttle vector are placed in a host cell in which recombination events can occur. Preferably the A box region is bracketed by two restriction enzyme sites. Thus, the A box region and the restriction enzyme sites can be used to insert any selected nucleic acid into the conditional replication shuttle vector. In one particular embodiment, the two restriction enzyme sites are Asc1 and Sma1. Preferably the selected nucleic acid is between 300 and 500 basepairs, though substantially larger nucleic acids can be used when desired.

In a particular embodiment the conditional replication shuttle vector further comprises two frt sites. The two fit sites are positioned on opposite sides of the A box. Since the frt sites are used in the resolution step following the co-integration of the selected nucleic acid with the IOBCV, when it is desired to place one or more markers into the IOBCV, these markers are also positioned in the conditional replication shuttle vector in between the two frt sites.

In an alternative embodiment, the conditional replication shuttle vector further comprises two homologous nucleotide sequences, which are homologous to each other, but preferably are not homologous to the IOBCV that comprises the nucleotide sequence which forms the co-integrate with the selected nucleic acid of the conditional replication shuttle vector. Preferably the homologous nucleotide sequence is longer than the corresponding selected nucleic acid. In one such embodiment the homologous nucleotide sequence is greater than 500 basepairs. In another embodiment the homologous nucleotide sequence is greater than 1000 basepairs. In still another embodiment the homologous nucleotide sequence is greater than 5000 basepairs. As described above for the two frt sites, the two homologous nucleotide sequences are positioned on opposite sides of the A box. Again, since the two homologous nucleotide sequences are used in the resolution step following the co-integration of the selected nucleic acid with the IOBCV, when it is desired to place one or more markers into the IOBCV, these additional markers are also positioned on the conditional replication shuttle vector in between the two homologous nucleotide sequences. As exemplified below, the two homologous nucleotide sequences preferably encode one or marker proteins (and peptides). Thus, in a preferred embodiment the homologous nucleotide sequence encodes the enhanced green fluorescent protein (IRESEGFP).

As indicated above, the present invention provides methods of selectively performing homologous recombination with a particular nucleotide sequence of an independent origin based cloning vector (IOBCV) that is contained in a recombination deficient host cell. Such methods comprise introducing a conditional replication shuttle vector into a recombination deficient host cell and therein enabling homologous recombination in the host cell via the transient expression of a recombination protein in the host cell. The host cell comprises an IOBCV which contains the particular nucleotide sequence whereas the conditional replication shuttle vector encodes a recombination protein that is transiently expressed by the host cell. The conditional replication shuttle vector also contains a nucleic acid that selectively integrates into the particular nucleotide sequence when the recombination protein is expressed. Neither the IOBCV alone, nor the IOBCV in combination with the host cell can independently support homologous recombination.

The present invention further provides methods of selectively modifying a particular nucleotide sequence of an independent origin based cloning vector (IOBCV) that is contained in a recombination deficient host cell that are particularly conducive for high throughput procedures. These high throughput procedures are preferentially performed almost entirely in liquid rather than on plates thereby facilitating the modification of multiple BACs at one time, (e.g., performing separate modifications to different BACs at the same time).

One such embodiment comprises introducing a conditional replication shuttle vector into a recombination deficient host cell in which the host cell contains an IOBCV that comprises a gene of interest which contains a particular nucleotide sequence. The conditional replication shuttle vector encodes a recombination protein that is expressed by the host cell and permits homologous recombination to occur in the host cell since neither the IOBCV alone, nor the IOBCV in combination with the host cell can independently support homologous recombination. Preferably the recombination deficient host cell cannot independently support homologous recombination because the host cell is RecA$^-$. In one embodiment the recombination protein is the rec E and rec T protein pair. In another embodiment the recombination protein is the Lambda beta protein. In yet another embodiment the recombination protein is the *Arabidopsis thaliana* DRT100 gene product. Preferably, the recombination protein is recA. The IOBCV is preferably a BBPAC and more preferably the BBPAC is a BAC.

The conditional replication shuttle vector contains a nucleic acid that selectively integrates into the particular nucleotide sequence when the recombination protein is expressed, thereby forming a co-integrate. The nucleic acid that selectively integrates into the particular nucleotide sequence and the nucleic acid encoding the recombination protein are positioned on the conditional replication shuttle vector such that upon resolution of the co-integrate, the nucleic acid encoding the recombination protein remains with the conditional replication shuttle vector. Thus, growing the host cell under conditions in which the conditional replication shuttle vector cannot replicate dilutes out the conditional replication shuttle vector encoding the recombination protein, and thereby prevents further (undesirable) recombination events in the recombination deficient cells to occur.

In a particular embodiment of this type, the conditional replication shuttle vector further comprises a nucleic acid that encodes a marker protein or peptide. The nucleic acid that selectively integrates into the particular nucleotide sequence and the nucleic acid encoding the marker protein or peptide are positioned on the conditional replication shuttle vector such that upon resolution of the co-integrate, the nucleic acid encoding the marker protein or peptide is inserted into or adjacent to the particular nucleotide sequence. In a particular embodiment, the conditional replication shuttle vector cannot replicate in the host cell because the conditional replication shuttle vector requires a particular protein for replication, and neither the host cell nor the IOBCV encode the particular protein. In a preferred embodiment of this type, the conditional replication shuttle vector cannot replicate in the host cell because the conditional replication shuttle vector comprises a R6Kγ origin of replication and neither the host cell nor the IOBCV encode pir.

In a more preferred embodiment the conditional replication shuttle vector further comprises a first frt site that is positioned on one side of the nucleic acid that selectively integrates into the particular nucleotide sequence, and a second fit site that is positioned on the other side of the nucleic acid that selectively integrates into the particular nucleotide sequence. In this embodiment, the resolution of the co-integrate is performed by adding flip recombinase to the host cell. Flip recombinase is preferably added to the host cell by introducing a plasmid that encodes flip recombinase to the host cell. In a preferred embodiment, the plasmid contains a conditional origin of replication such as a temperature-sensitive origin of replication which allows the plasmid to be diluted out by growing the host cells at a temperature that disfavors the replication of the plasmid. The conditional replication shuttle vector can further comprise a nucleic acid encoding one or more marker proteins and/or peptides that are positioned in between the two frt sites and are also adjacent to the nucleic acid that selectively integrates into the particular nucleotide sequence, such that after the resolution, the marker protein(s) and/or peptide(s) are contained by the IOBCV.

Alternatively, the resolution step can be performed by a second homologous recombination step. In one such embodiment, the conditional replication shuttle vector further comprises two homologous nucleotide sequences that are homologous to each other but are not homologous to the IOBCV. The two homologous nucleotide sequences are positioned on the conditional replication shuttle vector to be on opposite sides of the nucleic acid that selectively integrates into the particular nucleotide sequence so that the resolution of the co-integrate is performed by a recombination event between the two homologous nucleotide sequences. As described above, since the two homologous nucleotide sequences are used in the resolution step following the co-integration of the selected nucleic acid with the IOBCV, when it is desired to place one or more markers into the IOBCV, these additional markers are also positioned on the conditional replication shuttle vector in between the two homologous nucleotide sequences. As exemplified below, the two homologous nucleotide sequences preferably encode one or marker proteins. Thus, in a preferred embodiment the homologous nucleotide sequence encodes the enhanced green fluorescent protein (e.g., IRESEGFP).

A more preferred embodiment further comprises adding a counterselection agent after the resolution of the co-integrate to remove host cells that comprise the conditional replication shuttle vector. In this case, the conditional replication shuttle vector is designed to further comprise a counterselection gene that is positioned on the conditional replication shuttle vector such that upon resolution of the co-integrate the counterselection gene remains with the conditional replication shuttle vector. In a preferred embodiment of this type the counterselection gene is SacB. In a more preferred embodiment of this type, the counterselection agent is sucrose.

The present invention also provides the independent origin based cloning vector that contains a particular nucleotide sequence that has undergone homologous recombination with a conditional replication shuttle vector in a RecA-host cell of the present invention. In a particular embodiment, the conditional replication shuttle vector encodes a RecA-like protein. The particular nucleotide sequence can be all or part of a given gene such as the gene that encodes the murine zinc finger gene, RU49 (also known as Zipro 1) as exemplified below. The nucleotide sequence can be constructed to further contain specific translational or transcription elements such as an IRES, and/or marker proteins such as the green fluorescent protein. In one preferred embodiment the independent origin based cloning vector has undergone homologous recombination with a temperature sensitive shuttle vector in a RecA-host cell, wherein the temperature sensitive shuttle vector encodes a RecA-like protein. In another embodiment the independent origin based cloning vector is a BBPAC, and more preferably a BAC. In a specific embodiment of this type the independent origin based cloning vector has undergone homologous recombination with a temperature sensitive shuttle vector that is pSV1.RecA having the ATCC no. 97968.

The present invention also provides methods of using the modified independent origin based cloning vectors of the present invention to make transgenic animals including making animal models for diseases due to a dominant mutated allele, e.g., Huntington's disease; perform gene targeting; perform gene therapy; or for overexpressing in vivo proteins encoded by genes having an unknown function in order to determine the biological role of such genes, as exemplified below. The independent origin based cloning vectors or linearized nucleic acid inserts derived from the IOBCVs, for example, can be introduced into a eukaryotic cell or animal. In one such embodiment the transgenic animal made has a particular phenotype as a result of introducing (e.g., by pronuclear injecting) a BBPAC into the transgenic animal (or a fertilized zygote) which corresponds to a symptom of a particular disease. In this case, the BBPAC had been modified to contain a dominant allele known to be associated with and/or due to the particular disease.

In a related embodiment a BBPAC is identified that contains the wildtype copy of a gene that has been associated with one or more symptoms of a particular disease when the nucleotide sequence of the gene has a particular modification. In one such embodiment the BBPAC containing the wildtype gene is modified through homologous recombination by a method of the present invention, e.g. with a conditional replication shuttle vector, so that it contains the nucleotide sequence that has been associated with one or more symptoms of the particular disease. The modified BBPAC is then placed into a transgenic animal or a eukaryotic cell (e.g., a fertilized zygote) which results in a transgenic animal that has a phenotype that can be correlated with one or more symptoms of the particular disease. The transgenic animal can then be used as an animal model for the particular disease.

In one such embodiment the eukaryotic cell is a fertilized zygote. In another embodiment the eukaryotic cell is a mouse ES cell. The gene targeting, for example, can be performed to modify a particular gene, or to totally disrupt the gene to form a knockout animal. Similarly, IOBCVs made by the methods disclosed herein can be added in multiple copies to a fertilized mammalian zygote for example, in order to achieve overexpression of a particular protein. In addition, an IOBCV made by the methods disclosed herein can be used to make an animal model for a particular disease in which the expression of a mutated allele (carried by the IOBCV) leads to the desired phenotype for the animal model.

Thus in one aspect of the present invention, the independent origin based cloning vector contains a nucleic acid that has undergone homologous recombination with a conditional replication shuttle vector in a RecA⁻ whole cell, in which the conditional replication shuttle vector includes a RecA like protein. In a preferred embodiment the independent origin based cloning vector is a BBPAC. In a more preferred embodiment, the BBPAC has undergone homologous recombination with a TSSV. In the most preferred embodiment, the BBPAC has undergone homologous recombination with the TSSV that ispSVl.RecA having the ATCC no. 97968.

One particular embodiment is a method of using the BBPAC to introduce the nucleic acid into an animal to make a transgenic animal comprising pronuclear injecting of the BBPAC (or a linearized nucleic acid insert derived from the BBPAC) into a fertilized zygote. In one embodiment the animal is a mammal. In a more preferred embodiment the mammal is a mouse. In a specific embodiment of this type the independent origin based cloning vector is a BBPAC and the fertilized zygote is a C57BL/6 mouse zygote. In a preferred embodiment of this type two picoliters (pl) of less than one $\mu$g/ml BBPAC DNA is injected. In a more preferred embodiment 2 pl of 0.6 $\mu$g/ml of DNA is injected.

The present invention also includes a method of using the BBPAC of the invention to perform gene targeting in a vertebrate cells comprising introducing the BBPAC into the vertebrate cell wherein the nucleic acid that has undergone homologous recombination with the conditional replication shuttle vector, undergoes homologous recombination with the endogenous chromosomal DNA of the vertebrate cell. In preferred embodiments of this type the vertebrate cell is a mammalian cell. In a more preferred embodiment of this type the mammalian cell is a human cell. In a related embodiment the vertebrate cell is a fertilized zygote and the nucleic acid contains a disrupted gene. In a preferred embodiment the conditional replication shuttle vector is a TSSV. In a more preferred embodiment the TSSV is pSV1.RecA having the ATCC no. 97968.

The IOBCVs (including BBPACs and BACs) that have been modified by the methods of the present invention are also part of the present invention. The present invention further provides methods of producing non-human transgenic animals using these IOBCVs. One such method comprises introducing the IOBCV into a eukaryotic cell and placing the eukaryotic cell into a recipient animal, whereby the eukaryotic cell develops into the non-human transgenic animal. In one such embodiment, the eukaryotic cell is a fertilized animal zygote. In another embodiment the eukaryotic cell is an embryonic stem cell. In another embodiment, the eukaryotic cell is an ES-like cell. In addition, all of the non-human transgenic animals generated by such methodology are also part of the present invention.

The present invention also contains kits for performing homologous recombination on selected nucleotide sequences contained on an independent origin based cloning vector, such as a BBPAC. Any of the shuttle vectors of the present invention can be included in the kits. In one particular embodiment, the kit comprises a conditional replication shuttle vector and a building vector. In a preferred embodiment of this type, the kit further contains a restriction map for the shuttle vector and/or a restriction map for one or more of the building vectors. In a more preferred embodiment, the kit further includes a protocol for using the contents of the kit to perform homologous recombination.

A particular embodiment of the kit contains a TSSV, such as pSV1.RecA and a building vector. In one such embodiment the building vector is pBV.IRES.LacZ.PA. In another such embodiment the building vector is pBV.EGFP1. In yet another such embodiment the building vector is pBV.IRES.EGFP1. In still another such embodiment the building vector is pBV.pGK.Neo.PA.

In a preferred embodiment two or more building vectors are included in the kit. In a more preferred embodiment all four of the above-listed building vectors are included in the kit. Restriction maps for one or more of the building vectors or the TSSV may also be included in the kits. In addition, the kits may also include a protocol for using the contents of the kit to perform homologous recombination. In one specific embodiment, a kit contains pSV1.RecA and one or more of the above-listed vectors also contains fusaric acid and/or chloro-tetracycline.

Accordingly, it is a principal object of the present invention to provide a method for readily and specifically modifying an independent origin based cloning vector in a recombination deficient host cell.

It is a further object of the present invention to provide a method of transiently expressing a RecA-like protein in a RecA-host cell to allow the specific modification of a gene of interest contained by an independent origin based cloning vector.

It is a further object of the present invention to provide a method of generating deletions, substitutions, and/or point mutations in a specific gene contained by the independent origin based cloning vector in a RecA$^-$ cell.

It is a further object of the present invention to provide a conditional replication shuttle vector which encodes a RecA-like protein, and which further contains a specific nucleic acid in a recombination cassette that selectively undergoes homologous recombination with an independent origin based cloning vector when both vectors are present in a recombination deficient host cell.

It is a further object of the present invention to provide a temperature dependent shuttle vector which encodes a RecA-like protein.

It is a further object of the present invention to provide a temperature dependent shuttle vector which encodes a RecA-like protein, which further contains a specific nucleic acid in a recombination cassette that can selectively undergo homologous recombination with a gene of interest contained by an independent origin based cloning vector, when both vectors are placed in a recombination deficient host cell.

It is a further object of the present invention to provide a temperature sensitive shuttle vector that is pSV1.RecA having the ATCC no. 97968.

It is a further object of the present invention to provide a modified independent origin based cloning vector that can be used for the pronuclear injection of a nucleic acid contained by IOBCV into an animal zygote.

It is a further object of the present invention to provide a modified independent origin based cloning vector that can be transfected into an embryonic stem cell.

It is a further object of the present invention to provide a method of introducing a linearized nucleic acid insert from a modified independent origin based cloning vector into a fertilized zygote of an animal.

It is a further object of the present invention to provide a method of introducing a modified independent origin based cloning vector into an embryonic stem cell.

It is a further object of the present invention to provide a method of purifying a large linearized BBPAC.

It is still a further object of the present invention to provide a method for readily and specifically modifying an independent origin based cloning vector in a recombination deficient host cell under conditions that allow multiple modifications of IOBCVs at the same time.

These and other aspects of the present invention will be better appreciated by reference to the following drawings and Detailed Description.

BRIEF DESCRIPTION OF THE DRAWINGS

FIG. 1 shows the strategy for targeted BAC modification. (1) Two cloning steps are involved in constructing the shuttle vector. The recombination cassette (genomic fragments A and B; and IRES-LacZP-Poly A marker gene) is first constructed in the building vector and then subcloned into the temperature sensitive pSV RecA shuttle vector. (II) Co-integrate formation: Co-integrates can be formed through homologous recombination at either the homology A or the homology B site, with only the former case illustrated. (III) Resolution: Resolved BACs are selected by growth on plates containing fusaric acid and chloramphenicol. Correctly resolved clones are identified by colony hybridizations with an insert specific probe (e.g., a PGK polyA probe).

FIG. 2 shows a schematic representation of targeted modifications of the BAC 169, which contains the murine zinc finger gene, RU49. BAC169 containing RU49 was obtained from screening of the mouse 129 strain BAC genomic DNA library (Research Genetics).

FIG. 3 shows Southern blot analyses of BAC co-integrates and resolved BACs.

FIG. 4 shows pulsed field gel electrophoresis analyses of modified 169 with the ILPA insertion. DNA for two independent clones of BAC169. ILPA (L1 and L2) and BAC169 were prepared by alkaline lysis, and then digested with NotI, PmeI and XhoI (in a standard buffer supplemented with 2.5 mM spermidine). The digested DNA were separated by pulsed field gel electrophoresis (Bio-Rad's CHEF-DRII, 5 to 15s, 15 hours at 14° C.) and blotted on to nitrocellulose filter (Stratagene). The same filter was probed separately with three probes. L1 and L2 are lacZ1 and LacZ2 which are independent clones which correspond to clones 1 and 2 respectively in FIGS. 3C and 3D.

FIG. 5 shows the production of BAC transgenic mice.

FIG. 7 is a schematic diagram containing FIG. 7A which depicts a hypothetical map of a gene of interest within a selected BAC; FIG. 7B which depicts the first targeted modification to introduce the positive selection marker gene; and FIG. 7C which depicts the second modification to delete the promoter of the gene and to generate the short arm.

FIG. 13a, is a schematic drawing of the targeting vector which contains a 3.7 kb HindIII-HindIII and a 6 kb BamHI-XbaI fragments as the arms. The neo gene replaces the first two coding regions. Restriction sites are abbreviated as follows: B; BamHI, H; HindIII, R; EcoRI, X; XbaI. FIG. 13b shows the Southern blot analysis of a litter obtained from a heterozygous cross; tail DNA digested with BamHI and probed with 5' fragment shown in FIG. 13a. FIGS. 13c, and 13d, show the P20 midsagittal cerebellar paraffin sections that were stained with cresyl violet at P20. FIGS. 13e, and 13f are mitotic cells shown using immunohistochemistry using antibody to phosphorylated histone 3 on midsagittal sections of P9 cerebella. Representative positive cells indicated by arrows in –/– (FIG. 13e) and +/+(FIG. 13f).

FIGS. 14d and 14e show the fine restriction mapping of the BAC169 (lanes 1 and 4), BAC169tEGFP (lanes 2 and 5) and BAC169.ILPA (lanes 3 and 6). These BACs were digested with EcoRI (lanes 1–3) or HindIII (lanes 4–6) and probed with the 1.6 kb Xba-Hind probe (FIG. 14d) or with the 131 kb BAC169 probe (FIG. 14e).

FIG. 15a displays the Southern blot analysis of four BAC169tEGFP transgenic lines (F1 mice) and two wildtype mice using an IRES.EGFP1 probe. FIG. 15b displays the Northern blot analysis of Ru49 expression in the cerebella of P10 D1 and E6 transgenic mice and wildtype littermates. (FIG. 15c), the same Northern blot filter in FIG. 15b was probed with an IRES.EGFP1 probe. FIG. 15d displays the Western blot of cerebella from P7 transgenic and wildtype mice of the E6 that were probed with M2 Flag antibody. FIG. 15e shows that direct inspection under epifluorescence reveals EGFP1 expression in the BAC169tEGFP transgenic cerebellum. EGFP1 is not observed in the adjacent pons and brainstem (BS). FIG. 15f shows that on thick cerebellar sections (100 μM), EGFP1 is expressed in the EGL, the IGL and the molecular layer (ML). But, it is not expressed in the Pukinje cell layer (PC). FIG. 15g shows the Histochemical analysis of P7 LacZ fresh frozen sagittal sections. Expression is highest in the EGL but can be detected in the IGL as well.

FIG. 16a, shows the P12 transgenic and wildtype cerebella (CE). The width of the wildtype cerebellum is indicated by the bar. FIG. 16b, is a sagittal section of a P20 transgenic cerebellum. FIG. 16c, is a sagittal section of a wildtype P20 cerebellum. FIG. 16d, is a camera-lucida drawing of the posterior surface of a transgenic cerebellum, indicating the foliation pattern including three intralobular fissures: CrIF, CrIIF and PMDF. Actual examples of the posterior view of a transgenic cerebellum (FIG. 16e) and a wildtype cerebellum (FIG. 16f) are also shown. Abbreviations.: SC, superior colliculus; IC, inferior colliculus; Po, pons; V4, fourth ventricle; CP, choroid plexus; CrI, Crus I; CrII, Crus II; PMD, Paramedian lobule; COP, Copula pyramidis lobule.

FIG. 17e shows a bar chart depicting $^3$H-thymidine incorporation assays with P8 cerebellar granule cells. The absolute incorporation values from one of the four independent experiments is shown. The average incorporation level is shown as Mean+/−SEM. Statistical significance was measured using a t-test. In FIG. 17f, the number of mitotic cells (H3 labeled) in the EGL of P9 transgenic and wildtype littermates are shown as Mean+/−SEM.

FIGS. 18a–18d show the genetic influence of the Ru49 gene dosage on the formation of four intralobular fissures in the cerebellum at P20–P22. The number of animals used for each measurement (n) is indicated. The statistical significance was measured using the $\chi^2$ analysis. The asterisk indicates a P-value of less than 0.001.

FIG. 19a is a photograph of two mice showing the appearance of a BAC169.tEGFP transgenic mouse with alopecia at P20 (right) and a wildtype littermate (left). FIG. 19b shows tails of E6 transgenic (top) and wildtype(bottom) mice at P9 that are viewed under epifluoresencent microscope. FIG. 19c depicts the LacZ histochemical staining of the whole mount skin of BAC169.ILPA (Y7) transgenic mouse (left) and wildtype littermate (right). Transgenic (FIG. 19d) and wildtype mouse (FIG. 19e) skin sections were stained with cresyl violet. Abbreviations: dp, dermal papilla; hs, hair shaft; ec, epithelioid cysts; ut, utricle;sb, sebeceous gland. Transgenic (FIG. 19f) and wildtype (FIG. 19g) skin sections were stained with anti-H3 antibodies. Arrows show the H3 positive cells.

DETAILED DESCRIPTION OF THE INVENTION

Figure 2A:
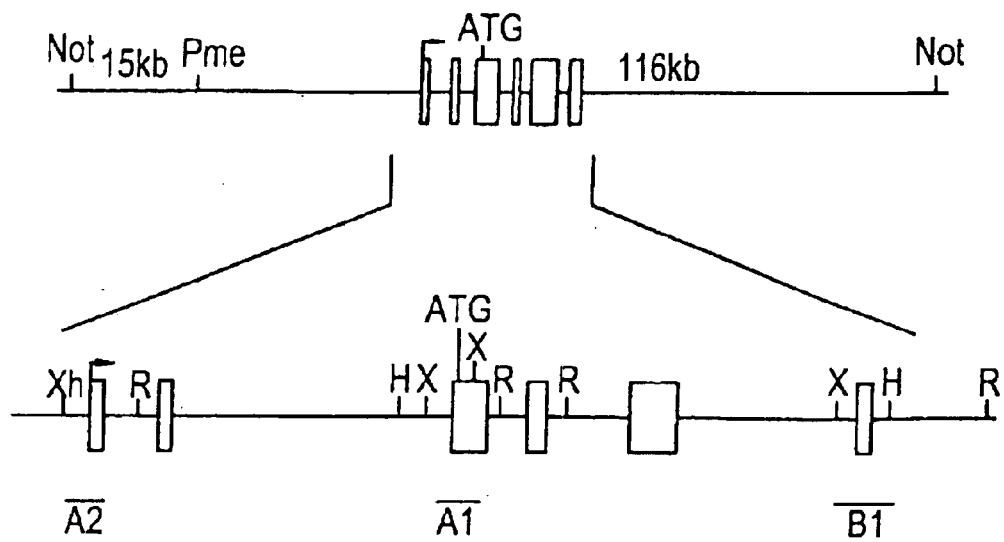
FIG. 2A depicts a restriction map of the BAC169. The position of several exons are shown. The region of homology A1 (1 kb PCR fragment) and homology B1 (1.6 kb Xba-Hind fragment) are indicated. Abbreviations: XhoI (Xh), EcoRI (R), HindIII (H), XbaI (X), NotI (Not) and PmeI (Pme).

The present invention provides a simple method for directly modifying an independent origin based cloning vector (IOBCV) in recombination deficient host cells including generating insertions (such as adding markers), deletions, substitutions, and/or point mutations in a specific gene contained in the independent origin based cloning vector. Such modifications may be performed with great specificity. The modified independent origin based cloning vectors of the present invention can be used to introduce a modified heterologous gene into a host cell. One specific use of such a modified vector is for the production of a germline transmitted independent origin based cloning vector transgenic animal.

Targeted independent origin based cloning vector modification can be used for functional studies in diverse biological systems. The ability to efficiently modify a independent origin based cloning vector and generate an IOBCV-transgenic animal has important applications for functional analyses of genes in viva. First, modified independent origin based cloning vectors can be used to study regulation of genes or gene complexes in transgenic animals such as mice. Since modified independent origin based cloning vectors can be used to study gene function in vivo, a deletion, substitution and point mutation within a given gene can be made in a independent origin based cloning vector, and the independent origin based cloning vector containing the modified gene can be reintroduced in vivo in its endogenous expression pattern. Furthermore, targeted independent origin based cloning vector modification can be used to create targeted expression of a selected gene, in the expression pattern of another gene, without prior knowledge of all of the regulatory elements of the selected gene. An important application of this type is targeted expression of the cre recominase for tissue/cell type specific gene targeting [Kuhn et al, Science 269:1427 (1995); Tsien et al., Cell 87:1317 (1996)]. In addition, modified independent origin based cloning vectors can be used to generate large DNA constructs particularly for placement into ES cells, ES-like cells [Cibelli et al, Nature Biotechnology 16:642–646 (1998); Pain et al, Cells Tissues Organs, 165:212–219 (1999)] or in vivo.

In one specific embodiment of the present invention the independent origin based cloning vector is a Bacterial Artificial Chromosome (BAC) modified in a host E. coli cell. A targeted BAC modification system has several advantages over a conventional yeast based modification system. First, a modified BAC automatically returns to the recombination deficient state after modification, ensuring stable maintenance of the modified BAC in the host strain. Second, BAC DNA can be very easily purified in relatively large quantities and high quality, allowing for use in biological experimentation including pronuclear injection. Third, since it is much easier to construct a BAC library than a YAC library, there are many more BAC libraries available from different species of animal, plants and microbes [Woo et al., Nucleic Acids Res., 22:4922 (1994); Wang et al., Genomics 24:527 (1994); Wooster et al, Nature 378:789 (1995)]. Most BACs also include all the necessary regulatory elements (i.e. LCRs and enhancers) to obtain dose dependent and integration site independent transgene expression [Dillon et al Trends Genet. 9:134 (1993); Wilson et al., *Annu. Rev. Cell. Biol.* 6–679 (1990); Bradley et al, *Nature Genet.* 14:121 (1997)]. Targeted BAC modification can be applied successively to dissect these elements. In addition, such a modified BAC may be used to generate a transgenic animal. The BAC (or PAC) stably integrates into the animal cell genome. The transgenic animal can be used for functional studies, including as an animal model for a disease, or for generating a desired gene product, such as producing a human protein in the milk of a transgenic mammal [Drohan et al U.S. Pat. No. 5,589,604, Issued Dec. 31, 1996]. Alternatively such modified BACs or PACs may be used for delivering a specific gene in gene therapy.

In the Examples below, modified BACs have been successfully inserted into murine subject animals, and in vivo heterologous gene expression has been demonstrated. In Example 2, below, a modified BAC construct was constructed so that the C-terminus of the gene product of the gene of interest was fused with two in-frame epitope tags and the gene of interest was further appended to an IRES/ EGFP marker gene. As is apparent, similar modifications can be performed so that the N-terminus of the gene product of the gene of interest comprises one or more markers. Indeed, the present methodology allows any portion of the BAC DNA to be altered/modified and therefore also allows such modifications/alterations/deletions at any site of the gene product of the gene of interest. Thus, the methods of the present invention are fully amenable to modifications, alterations, fusions and the like to selected genes of interest and/or portions thereof (e.g., the coding regions) and furthermore can be successfully employed for generating animals with desired genotypes and/or phenotypes.

Heretofore, genetic analysis in mice has most commonly employed two general strategies: phenotypic screens for spontaneous or induced mutations; and genotypic analysis using homologous recombination or gene trapping to produce deletion or insertion mutants. Although genetic analysis in invertebrates has recently emphasized over- or misexpression studies to understand gene function, the use of increased gene dosage analysis in mice has been hampered by variability in the expression patterns and levels of most conventional transgenes. As demonstrated below, bacterial artificial chromosome (BAC) mediated gene dosage analysis in transgenic mice can be employed to reveal novel genetic functions that are not evident from conventional loss-of-function mutations. In the Examples below, the role of the zinc finger transcription factor Ru49 (Zipro 1) is elucidated in the proliferation of granule cell precursors in the developing cerebellum, and the contribution of this process to the final stages of cerebellar morphogenesis is documented. Ru49 is also found to be expressed in the skin, and increased Ru49 gene dosage results in a hair loss phenotype that is associated with increased epithelial cell proliferation and abnormal hair follicle development. These results demonstrate that BAC mediated gene dosage studies as disclosed herein can play an important role in the analysis of gene expression and function in vertebrates. Indeed, the methods disclosed herein can also be used to correctly express dominant negative or gain-of-function mutations via BAC mediated transgenesis that offer additional avenues for genetic analysis in a selected animal (e.g., a mouse or a monkey).

The present invention further provides a simple and rapid method for modifying and then resolving IOBCVs (e.g, BACs) in *E. coli* which is useful for large scale modification of BACs. One such method employs a shuttle vector that comprises a conditional origin of replication (e.g., the R6Kγ DNA origin of replication), a nucleic acid encoding a recombination protein, (e.g., recA,) to induce the host cell to support homologous recombination, and a positive counter-selection marker, (e.g., the SacB gene which allows the selection for resolved BAC clones by sucrose). Preferably, the procedure is performed by a high throughput method which allows the modification of the IOBCV is liquid and allows the efficient resolution of the vector.

The methodology of the present invention is very general. Whereas the targeted independent origin based cloning vector modification is demonstrated on BACs, the system is readily applicable to BBPACs in general including PACs, P1 and other vectors propagated in the recombination deficient *E. coli*. In addition, the BAC modification exemplified herein, is also apropo to Mammalian Artificial Chromosomes. For example, Harrington et al. [*Nature Genetics*, 15:345–355 (1997)] have used BAC derived DNA as a component of their Human Artificial Chromosome. Therefore, the use of such human artificial chromosomes can include the BAC modification taught by the present invention.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

As used herein an "IOBCV" is an independent origin based cloning vector. One example of such a cloning vector is a BBPAC defined below. An IOBCV generally comprises a nucleic acid insert which either is or contains a gene of interest.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

As used herein, a "Bacterial or Bacteriophage-Derived Artificial Chromosome" or "BBPAC" denotes a vector that is derived from a bacterium or bacteriophage such as a Bacterial Artificial Chromosome (BAC) which is an *E. coli* F element based cloning system, a P1-Derived Artificial Chromosome (PAC) or a lambda-based cosmid. In one embodiment, the BBPAC encodes from 500 to 700 kilobases of genomic sequences. In another embodiment, the BBPAC encodes up to 500 kilobases of genomic sequences. In a preferred embodiment, the BBPAC encodes between 120 to 180 kilobases of genomic sequences. In one particular embodiment the BBPAC encodes 130 kilobases of genomic sequences. A BBPAC used for gene targeting can be referred to as a "BBPAC targeting construct" and contains a nucleic acid insert comprising the gene targeting construct.

A "gene targeting construct" as used herein is used interchangeably with "targeting construct" and is a nucleic acid that when introduced into a cell undergoes homologous recombination with the endogenous chromosomal DNA of the cell. The nucleic acid is introduced into the cell to induce a modification of a particular gene contained on the endogenous chromosomal DNA, including in particular cases, to disrupt that gene to create a knockout animal.

As used herein a recombinant deficient host cell is "RecA⁻" when the host cell is unable to express a RecA-like protein, including recA itself, which can support homologous recombination. In the simplest case, the gene encoding the RecA-like protein has been deleted in a RecA⁻ host cell. Alternatively the RecA-host cell contains a mutation in the recA gene that impairs its function.

A "RecA-like protein" is defined herein to have the meaning generally accepted in the art except as used herein the recA protein itself is included as being a specific RecA-like protein. RecA-like proteins are proteins involved in homologous recombination and are homologs to recA [Clark et al., *Critical Reviews in Microbiology* 20:125–142 (1994)]. The recA protein is the central enzyme in prokaryotic homologous recombination. It catalyzes pairing and strand exchange between homologous DNA molecules, and functions in both DNA repair and genetic recombination [McKee et al., *Chromosoma* 7:479488 (1996)]. A number of RecA-like proteins have been found in eukaryotic organisms and yeast [Reiss et al., *Proc.Natl.Acad.Sci.* 93:3094–3098 (1996)]. Two RecA-like proteins in yeast are Rad51 and Dmc1 [McKee et al. (1996) supra]. Rad51 is a highly conserved RecA-like protein in eukaryotes [Peakman et al., *Proc.Natl.Acad.Sci.* 93:10222–10227 (1996)].

A "recombination protein" as used herein is a protein involved in homologous recombination that can be used either alone or in conjunction with other proteins to allow homologous recombination to proceed in a cell that is otherwise recombination deficient. Examples of recombination proteins include RecA-like proteins, the rec E and rec T proteins which are encoded by the Rec E gene [Clark et al, *J.Bacteriol* 175:7673–7682 (1993); Hall et al., *J. Bacteriol* 175:277–287 (1993); Kusano et al. 138:17–25 (1994); also reviewed by Clark and Sandler, *Crit Rev Microgiol,* 20:125–142 (1994)], the Lambda beta protein [Berger and Cohen, *J. Bacteriol.* 171:3523–3529 (1989)] and the *Arabidopsis thaliana* DRT100 gene product [Pang et al., *Proc. Natl. Acad. Sci.* 89:8073–8077 (1992)].

As used herein a "gene of interest" is a gene contained by a host cell genome or more preferably an independent origin based cloning vector that has been selected to undergo homologous recombination with a specific nucleic acid contained in a recombination cassette. A gene of interest can be either specifically placed into the host cell or independent origin based cloning vector for this purpose, or already contained by the host cell or independent origin based cloning vector.

As used herein a "marker" is an indicator, whose presence or absence can be used to distinguish the presence or absence of a particular nucleic acid and preferably the corresponding presence or absence of a larger DNA which contains and/or is linked to the specific nucleic acid. In a preferred embodiment the marker is a protein or a gene encoding the protein, and thus can be more specifically termed a "marker protein" or a "marker gene". The term "marker" (and thus marker protein or marker gene) is meant to be used extremely broadly and includes fluorescent proteins such as green fluorescent protein, enzymes such as luciferase, and further includes drug resistant proteins, whose presence or absence may not solely be regarded as a means to detect cells that contain the drug resistance protein; and/or the genes that encode such proteins. However, drug resistance proteins and/or their corresponding genes can allow the preferential growth of cells that contain the drug resistant gene (or alternatively allow the counter-selection of cells that do not contain the drug resistant gene) and therefore bestow a type of selectable distinction which is meant to fall within the present definition of a marker.

The term "a gene which encodes a marker protein" is used herein interchangeably with the term "marker protein gene" and denotes a nucleic acid which encodes a marker protein.

A "cassette" refers to a segment of DNA that can be inserted into a vector at specific restriction sites. The segment of DNA encode a polypeptide of interest, and the cassette and restriction sites are designed to ensure insertion of the cassette in the proper reading frame for transcription and translation. The present invention provides a recombination cassette that includes two homology fragments interrupted by an insertion, deletion or mutation sequence.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guano sine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

"Homologous recombination" refers to the insertion of a modified or foreign DNA sequence contained by a first vector into another DNA sequence contained in second vector, or a chromosome of a cell. The first vector targets a specific chromosomal site for homologous recombination. For specific homologous recombination, the first vector will contain sufficiently long regions of homology to sequences of the second vector or chromosome to allow complementary binding and incorporation of DNA from the first vector into the DNA of the second vector, or the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein the terms "fusion protein" and "fusion peptide" are used interchangeably and encompass "chimeric proteins and/or chimeric peptides" and fusion "intein proteins/peptides". A fusion protein of the present invention comprises at least a portion of the protein or peptide encoded by a gene of interest of the present invention joined via a peptide bond to at least a portion of another protein or peptide in a chimeric/fusion protein. For example, fusion proteins can comprise a marker protein or peptide, or a protein or peptide that aids in the isolation and/or purification of the protein or peptide encoded by a gene of interest of the present invention.

A "heterologous nucleotide sequence" as used herein is a nucleotide sequence that can be covalently combined with a gene of interest of the present invention (e.g., by homologous recombination) to modify the gene of interest. Such nucleotide sequences can encode chimeric and/or fusion proteins. The heterologous nucleotide sequence can also encode peptides and/or proteins which contain regulatory and/or structural properties. In another such embodiment a heterologous nucleotide sequence can encode a protein or peptide that can function as a means of detecting a protein or peptide encoded by a gene of interest (contained by a BAC, for example). In still another such embodiment a heterologous nucleotide sequence can function as a means of detecting a nucleotide sequence of the present invention. A heterologous nucleotide sequence can also comprise non-coding sequences including restriction sites, transcriptional regulatory elements, promoters and the like.

A particular nucleotide sequence comprising a gene of interest, whether genomic DNA or cDNA, can be isolated from any source, particularly from a human cDNA or genomic library. In view and in conjunction with the present teachings, methods well known in the art, as described above can be used for obtaining such genes from any source [see, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989")].

Selectively Performing Homologous Recombination

Accordingly, any animal cell potentially can serve as the nucleic acid source for the molecular cloning of any selected gene. The DNA may be obtained by standard procedures known in the art from cloned DNA (e.g., a DNA "library"), and preferably is obtained from a cDNA library prepared from tissues with high level expression of the protein by chemical synthesis, by cDNA cloning, or by the cloning of genomic DNA, or fragments thereof, purified from the desired cell (See, for example, Sambrook et al., 1989, supra; Glover, D.M. (ed.), 1985, DNA Cloning: A Practical Approach, MRL Press, Ltd., Oxford, U.K Vol. 1,1). Clones derived from genomic DNA may contain regulatory and intron DNA regions in addition to coding regions; clones derived from cDNA will not contain intron sequences.

The present invention provides methods for selectively performing homologous recombination in a cell that normally cannot independently support homologous recombination. A specific nucleic acid is inserted into a recombination cassette that selectively integrates into a particular nucleotide sequence when the recombination deficient cell is transiently induced to support homologous recombination. More particularly, the present invention allows the integration of a specific nucleic acid into a particular nucleotide sequence of a gene of interest. The methods provided by the present invention minimize the nonspecific nucleotide sequence rearrangements and deletions, which are characteristic of other systems which involve host cells that normally support homologous recombination.

In one case the specific nucleic acid can encode an entirely different protein than the gene of interest, and the gene of interest may be selected for the tissue specificity of its promoter, for example for use in generating a transgenic animal, or in a gene therapy protocol. In one such embodiment the rat preproenkephalin gene may be used as the gene of interest since the preproenkephalin promoter has been shown to confer brain expression and synaptic regulation in transgenic mice. [Donovan et al., *Proc.Natl.Acad.Sci.* 89:2345–2349 (1992)]. In the Examples below, the murine zinc finger gene, RU49 was used as the gene of interest. Alternatively, the specific nucleic acid can be constructed so as to cause a deliberate and specific modification in the sequence of the gene of interest, for example for inducing a change in the amino acid sequence of the gene product, such as is typically done in site-directed mutagenesis protocols.

In one aspect of the present invention, the recombination deficient host cell cannot independently support homologous recombination because the host cell is RecA. However, as any person skilled in the art would readily understand, alternative causes for recombination deficiency may be rectified by methods that are analogous to those taught by the present invention and/or readily apparent in view of such teachings. For example recombination deficiency may be due to a deficiency of an alternative recombination protein such as another Rec protein including recB, recC, recD, and recE [Clark et al., *Critical Reviews in Microbiol.* 20:125–142 (1994)] which may be manipulated in a manner that is analogous to that taught herein for RecA-like proteins.

In the case of a RecA⁻ host cell, inducing the host cell to transiently support homologous recombination comprises inducing the transient expression of a RecA-like protein in the host cell. Such induction may be performed by expressing a RecA-like protein contained by the recombination deficient host that is under the control of an inducible promoter.

In a preferred aspect of the invention inducing the transient expression of the RecA-like protein is performed with a conditional replication shuttle vector that encodes the RecA-like protein. Conditional replication shuttle vectors can also include pBR322 in a polyA temperature-sensitive bacterial strain. In a particular embodiment, the conditional replication shuttle vector is a temperature sensitive shuttle vector (TSSV) that replicates at a permissive temperature, but does not replicate at a non-permissive temperature.

Inducing the transient expression of the RecA-like protein consists of transforming the host cell with the TSSV at a permissive temperature, and growing the host cell at a non-permissive temperature. The TSSV encodes a RecA-like protein that is expressed in the host cell and supports the homologous recombination between a specific nucleic acid contained in a recombination cassette and the particular nucleotide sequence contained in the host cell. The TSSV encoding the RecA-like protein is diluted out when the host cell is grown at the non-permissive temperature.

In a more intricate version of the present invention, the particular nucleotide sequence which has been selected to undergo homologous recombination is contained by an independent origin based cloning vector (IOBCV) that is comprised by the host cell, and neither the independent origin based cloning vector alone, nor the independent origin based cloning vector in combination with the host cell, can independently support homologous recombination. In a particular embodiment of this type both the independent origin based cloning vector and the host cell are RecA⁻, and inducing the host cell to transiently support homologous recombination comprises inducing the transient expression of the RecA-like protein to support homologous recombination in the host cell. The independent origin based cloning vector can be a BBPAC, such as the BAC exemplified below and the host cell can be a host bacterium, such as *E. coli*.

The independent origin based cloning vectors for use in the methods of the present invention can be obtained from a number of sources. For example, *E. coli*-based artificial chromosomes for human libraries have been described [Shizuya et al., *Proc. Natl. Acad. Sci.* 89:8794–8797 (1992); Ioannou et al., *In Current Protocols in Human Genetics* (ed. Dracopoli et al.) 5.15.1–5.15.24 John Wiley & Sons, New York (1996); Kim et al., *Genomics* 34:213–218 (1996)]. Libraries of PACs and BACs have been constructed [reviewed in Monaco et al., *Trends Biotechol.,* 12:280–286 (1994)], that are readily isolated from the host genomic background for example by classical alkaline lysis plasmid preparation protocols [Birnboim et al., *Nucleic Acids Res.* 7:1513–1523 (1979)], or alternatively, with the use of a nucleobond kit, a boiling Prep, or by cessium gradient (Maniatis, supra). BAC, PAC, and P1 libraries are also available for a variety of species (e.g. Research Genetics, Inc., Genome Research, Inc., Texas A&M has a BAC center to make a BAC library for livestock and important crops). Also BACs can be used as a component of mammalian artificial chromosomes.

An independent origin based cloning vector that is a BAC can be isolated using a cDNA or genomic DNA probe to screen a BAC genomic DNA library, for example. The use of a mouse genomic BAC library from Research Genetics is exemplified below. A positive BAC can generally be obtained in a few days. To insert a gene of interest into a selected locus in the BAC, the region of insertion can be mapped for restriction enzyme sites. Whereas subcloning is necessary for detailed mapping, it is generally unnecessary since rough mapping is usually sufficient. As is readily apparent, other independent origin based cloning vector genomic libraries can be screened and the isolated independent origin based cloning vectors manipulated in an analogous fashion.

The conditional replication shuttle vectors of the present invention are constructed so as to contain a recombination cassette that can selectively integrate into the nucleotide sequence of the gene of interest encoded by the independent origin based cloning vector. Such conditional replication shuttle vectors can be constructed by inserting a PCR amplified RecA-like gene into an appropriate conditional replication shuttle vector which either contains a specific drug resistant gene or can be subsequently modified to contain one. In a preferred embodiment the drug resistant gene can also be counter-selected against, such as with, tetracycline and fusaric acid. Alternatively, in addition to the drug resistant gene the conditional replication shuttle vector can also contain a counter-selection gene such as a gene that confers sensitivity to galactose, for example.

In the Example 1 below, the *E. coli* K12 recA gene (1.3 kb) is inserted into the BamHI site of a pMBO96 vector. In this case the vector already carried a gene that bestows tetracycline resistance, and in addition contains a pSC101 temperature sensitive origin of replication, which allows the plasmid to replicate at 30 degrees but not at 43 degrees.

The RecA-like protein of a conditional replication shuttle vector can be controlled by either an inducible promoter or a constitutive promoter. In one particular embodiment the transient expression of the RecA-like protein is achieved by the transient induction of the inducible promoter in a host cell. In another embodiment, the constitutive promoter is the endogenous *E. coli* recA promoter.

The conditional replication shuttle vector should also contain at least one unique cloning site. When a building vector is used for the construction of the recombination cassette as described below, one unique site is reserved for transferring the recombination cassette containing the specific nucleic acid from the building vector to the conditional replication shuttle vector. For example a polylinker can be inserted between two specific restriction sites to create additional restriction sites that allow cloning of the recombination cassette into the conditional replication shuttle vector. In any case the conditional replication shuttle vector created should minimally contain a recombination cassette comprising the specific nucleic acid, (e.g., containing a point mutation, deletion or a marker gene) flanked at both the 5' and 3' ends by genomic fragments containing preferably about 350 basepairs (e.g. 250 basepairs to 600 basepairs though less may be sufficient) or more of the gene of interest of the independent origin based cloning vector.

In certain cases a building vector is used to construct the recombination cassette. Two small genomic fragments, each containing about 350 basepairs (e.g. 250 basepairs to 600 basepairs though less may be sufficient) or more of the gene of interest are cloned into the building vector (e.g., pBB1) in appropriate order and orientation to generate the flanking regions of the recombination cassette. DNA containing a promoter sequence 5' to the specific nucleic acid, which in turn is 5' to a polyadenine addition signal sequence, is inserted between the two genomic fragments in the proper orientation. The recombination cassette is then transferred into the conditional replication shuttle vector (e.g., pSV1RecA). The recombination cassette, the RecA-like protein gene, and the drug resistant gene are linked together on the conditional replication shuttle vector such that when the specific nucleic acid integrates into the particular nucleotide sequence, the RecA-like protein gene and the drug resistant gene remain linked together, and neither the RecA-like protein gene nor the drug resistant gene remain linked to the integrated specific nucleic acid. In a preferred embodiment the conditional replication shuttle vector is a TSSV and the TSSV is pSV1.RecA having the ATCC no. 97968.

According to the methods of the present invention the conditional replication shuttle vector is transformed into a RecA⁻ host cell containing the independent origin based cloning vector. The independent origin based cloning vector can also contain a gene which bestows resistance to a host cell against a corresponding toxic agent/drug such as an antibiotic or in a specific embodiment, chloramphenicol. The cells are grown under the conditions in which the conditional replication shuttle vector can replicate (e.g., when the conditional replication shuttle vector is a TSSV which replicates at 30° but not at 43°, the host cell is grown at 30° C.) and the transformants can be selected via the specific drug resistant gene (or first drug resistant gene) carried by conditional replication shuttle vector, and the second drug resistant gene carried by the independent origin based cloning vector. Since the conditional replication shuttle vector also carries the RecA-like protein gene, homologous recombination can occur between the conditional replication shuttle vector and the independent origin based cloning vector to form co-integrates through the sequence homology at either the 5' or the 3' flanking regions of the recombination cassette. The co-integrates then can be selected by growing the cells on plates containing the first and second drugs at non-permissive conditions (e.g. for the TSSV above, at 43° C.) so that the non-integrated, free conditional replication shuttle vectors are lost. This results in the selection for host cells carrying the integrated conditional replication shuttle vectors, (which co-integrate either into the independent origin based cloning vector or into the host chromosome). Correct independent origin based cloning vector co-integrates can be identified by PCR or more preferably with Southern blot analyses.

The co-integrates can then be re-streaked onto plates containing the second drug, (i.e., the drug which the gene initially carried by the independent origin based cloning vector protects against) and grown under non-permissive conditions overnight. A fraction of the co-integrates undergo a second recombination event (defined as resolution), through sequence homology at either the 5' or the 3' flanking regions of the recombination cassette. The resolved independent origin based cloning vector automatically loses both the first drug resistant gene (i.e., the specific drug resistant gene contained by the conditional replication shuttle vector) and the RecA-like protein gene due to the linkage arrangement of the RecA-like protein gene, the drug resistant gene and the specific nucleic acid on the conditional replication shuttle vector, described above. In addition, the excised conditional replication shuttle vector cannot replicate under the non-permissive conditions and is therefore diluted out.

The resolved independent origin based cloning vectors can be further selected for by growing the host cells (e.g., at 37° C.) on plates containing the second drug and an agent that counterselects against cells containing the gene resistant to the first drug (e.g., a gene conferring tetracycline resistance may be counter-selected against with fusaric acid). The resolved independent origin based cloning vector will be either the original independent origin based cloning vector or the precisely modified independent origin based cloning vector. One method to identify the correctly resolved BAC is to choose 5–10 colonies and prepare a miniprep DNA. The DNA can then be analyzed using Southern blots to detect the correct targeting events. Alternatively, the desired clones can be identified by colony hybridization using a labeled probe for the specific nucleic acid contained by the recombination cassette. Such probes are well known in the art, and include labeled nucleotides probes that hybridize to the nucleic acid sequence. Alternatively, a marker nucleic acid can be included in the recombination cassette and constructed so as to remain with the specific nucleic acid upon integration into the independent origin based cloning vector.

The marker can be a marker gene or marker nucleic acid that encodes a marker protein that confers a specific drug resistance to the host cell, as exemplified above, against drugs such as antibiotics, e.g., ampicillin, chloramphenicol, and tetracycline, a protein that confers a particular physical characteristic to the cells, such as a green fluorescent protein or a modified green fluorescent protein as described in U.S. Pat. No. 5,625,048, Issued Apr. 29, 1997 and WO 97/26333 Published Jul. 24, 1997 (the disclosures of which are hereby incorporated by reference in their entireties), or an enzyme such as luciferase. Alternatively, it can be another marker protein including e.g., β-galactosidase.

The methods of homologous recombination of the present invention are selective, and nonspecific nucleotide sequence rearrangements either do not occur, or are essentially undetectable by one or more conventional methods of analysis. One such method includes pulsed field gel mapping of the modified independent origin based cloning vector and the unmodified independent origin based cloning vector to determine whether any unexpected deletions, or insertions or rearrangement were generated during the modification procedure. In one particular embodiment, the same filter can be probed separately with a probe for the whole independent origin based cloning vector, with a probe for the specific nucleic acid, and a probe for a region of the gene of interest that has not been modified. A restriction enzyme digestion can reveal a finger print of the modified independent origin based cloning vectors indicating whether the fragments are preserved. Such a restriction enzyme digestion is exemplified below. Restriction enzyme digestions can be repeated with one or more additional restriction enzymes selected with respect to the restriction site map of the independent origin based cloning vector.

In an alternative method, the modified independent origin based cloning vector and the unmodified independent origin based cloning vector can be assayed with both a probe specific for any region of the DNA contained by the recombination cassette predicted to be inserted into the independent origin based cloning vector (e.g., the promoter sequence, the specific nucleic acid, and a polyadenine addition signal sequence) and a probe specific for a region outside of the modification region (e.g., near the promoter region but outside of the modification region).

A modified independent origin based cloning vector of the present invention can be purified by gel filtration, e.g. a column filled with SEPHAROSE CL-4B yielded intact linear BAC DNA. The column can be pre-equilibrated in an appropriate buffer, as described in the Example 1 below. The purified DNA can be directly visualized with ultraviolet light after ethidium bromide staining, for example. Columns such as the SEPHAROSE CL-4B column also can efficiently separate degraded DNA from the pure linear DNA.

Methods of Using Modified IOBCVs

The present invention also provides methods of using the modified independent origin based cloning vectors of the present invention. Such modified independent origin based cloning vectors contain a nucleic acid that can be inserted into an animal to make a transgenic animal. The modified independent origin based cloning vectors of the present invention can be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, *J. Biol. Chem.* 267:963–967; Wu and Wu, 1988, *J. Biol. Chem.* 263:14621–14624; Hartmut et al., Canadian Patent Application No. 2,012,311, filed Mar. 15, 1990).

Constitutive expression of any selected gene, even if at low levels is contemplated by the present invention. Various therapeutic heterologous genes can be inserted into an independent origin based cloning vector of the invention such as but not limited to adenosine deaminase (ADA) to treat severe combined immunodeficiency (SCID); marker genes or lymphokine genes into tumor infiltrating (TIL) T cells [Kasis et al., *Proc. Natl. Acad. Sci. U.S.A.* 87:473 (1990); Culver et al., ibid. 88:3155 (1991)]; genes for clotting factors such as Factor VIII and Factor IX for treating hemophilia [Dwarki et al. *Proc. Natl. Acad. Sci. USA*, 92:1023–1027 (1995); *Thompson, Thromb. and Haemostatis*, 66:119–122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, ornithine transcarbamylase, apolipoproteins, and the like. In general, see U.S. Pat. No. 5,399,346 to Anderson et al.

One particular method comprises the pronuclear injection of the modified independent origin based cloning vector into a fertilized animal zygote. Such a method is exemplified below with the modified independent origin based cloning vector being a BAC which has been linearized, and the animal zygote being a mouse zygote. 2 pl of 0.6 μg/ml of BAC DNA was injected. Alternatively, the BAC can be introduced into an embryo which is then transplanted into a recipient animal.

The presence of both ends of the modified independent origin based cloning vector can be assayed for in the transgenic animal to determine if the intact nucleic acid insert of the IOBCV has been integrated into the genome. Since both ends of the nucleic acid insert contain some vector sequence, PCR primers specific to the vector sequence can be generated and used to amplify the transgenic DNA. The amplified products can then be probed with a third labeled oligonucleotide probe within the amplified region.

The transgenic animals that are formed give rise to germline transmission after appropriate breeding (B6/CBA mice were used in the Example 1). The ratio of transgenic animals to wild type animals should follow Mendelian genetics.

The expression of the specific nucleic acid and/or the gene of interest inserted into the transgenic animal can be determined by a variety of methods well known in the art which depend on the nature of the insert. For example, enzymes can be appropriately assayed for activity, in the case of β-galactosidase, whole mount staining can be performed, in situ hybridization can be used to detect the corresponding mRNA, and specific antibodies can be used to identify the expression of a corresponding protein. In preferred embodiments such expression will be evident only in cells in which the endogenous gene of interest is expressed. In Example 1, in which the gene of interest was the murine zinc finger RU49, and the specific nucleic acid inserted therein was the lacZ marker gene, analyses of the expression of the lacZ marker gene in the entire cerebellum of postnatal day 6 transgenic mice closely resembled the corresponding endogenous RU49 expression pattern. In Example 2, RU49 was epitope-tagged with FLAG and His, and coexpressed with enhanced green fluorescent protein using an IRES.

The present invention also provides the use of targeted BBPAC modification to obtain a high rate of gene targeting in vertebrates. The BBPAC contains a nucleic acid insert comprising the gene targeting construct. The circular BBPAC can be used, or preferably the linearized nucleic acid insert is used. In either case, the BBPAC or linearized nucleic acid insert can be purified by gel filtration as described herein.

In one aspect of the invention the gene targeting is performed in ES cells using a BBPAC gene targeting construct that is greater than 100 kb. In a general sense, the BBPAC gene targeting construct is similar to the conventional positive selection gene targeting construct (FIG. 7): it contains two regions of homology, a long arm (>80 kb) and a short arm (10–20 kb), with the neo cassette (pgk-neo-polyA) introduced into the middle of the BBPAC. Two targeted BBPAC modifications are used to make this construct. The first modification is to introduce the neo gene to disrupt the gene of interest in the BBPAC. A second modification is to create the short arm (10–20 kb). The reason for the second modification is enable the use of an endogenous probe flanking the short arm (KO probe) to detect a polymorphism between the targeted allele and the wild type allele in screening ES cell clones (FIG. 7; *Gene Targeting, a practical approach*, supra).

A preferred version of the BBPAC gene targeting methodology of the present invention also includes negative selection. The conventional negative selection cassettes, such as the use of the herpes thymidine kinase cassette or the diphtheria toxin gene cassette, may not always work with BBPAC constructs since BBPAC DNA tends to exist in transfected mammalian cells as episomal DNA for a long period of time [Baker et al., *NAR* 25:1950–1956]. In one example, the EGFP1 cassette can be used as a negative screening cassette. In this case, in the second step of modification to generate the short arm, the CMV promoter driven green fluorescent protein (EGFP-1) and the polyA signal can be introduced. Unlike other negative selection cassettes, GFP is not toxic to the cells but serves as a fluorescent marker protein. When gene targeting occurs, the EGFP-1 cassette will be lost and the cell will not exhibit a green fluorescence under UV light. On the other hand, when the BBPAC integrates non-homologously, the EGFP-1 cassette also integrates, and the cells will therefore exhibit the green fluorescence under UV. For the definitive Southern blot analyses only those neo resistant cell lines which do not exhibit a green fluorescence under UV light are chosen.

The process of generating the targeted ES cells with a BBPAC targeting construct is essentially the same as with the conventional protocols (Gene Targeting, A Practical Approach, supra), except for the following steps. First the linearized intact BBPAC nucleic acid insert (for example) is purified using the gel filtration procedure described herein. Next, the transfection of ES cells with the linearized intact BBPAC nucliec acid insert is performed as described by Baker [NAR, 25:1950–1956 (1997)], using psoralen-inactivated adenovirus as carriers, for example.

The method enables transfection efficiency in mammalian cells with linear BBPAC DNA to be similar to the transfection efficiency of a conventional DNA construct. On the other hand, the BBPAC targeting construct can potentially provide 10–100 fold higher targeting frequency than the conventional targeting construct, thereby making gene targeting in mouse ES cells easier and cheaper, since only a few dozen colonies need to be isolated and screened to obtain the targeted clones.

The present invention further provides a method of performing gene targeting in fertilized vertebrate zygotes by the injection of a BBPAC targeting construct, or preferably the linearized intact BBPAC nucleic acid insert containing the targeting construct to generate a transgenic knock-out animal (TKO). A large targeting construct (>100 kb) can provide a very high targeting rate (predicted by mathematical modeling described above) and gene targeting can be directly performed with a fertilized vertebrate zygote via pronuclear injection of the modified BBPAC targeting construct. TKO methodology has previously been attempted by Brinster et al. [PNAS, 86:7087–91 (1989)] with a small DNA construct (2.6–8.9 kb) but those workers only obtained a relatively low targeting rate (0.2%). The large homology DNA in the BBPAC (>100 kb) of the present invention increases the targeting rate to a favorable range of 2% to 10%.

In one such embodiment, the design of the gene targeting construct is similar to the ES cell targeting construct except that instead of the neo gene, an IRES-GFP cassette or an IRES-lacZ cassette is fused to an exon of the gene of interest to disrupt the gene (FIG. 7). As described above, two consecutive steps of BBPAC modifications are involved in generating the BBPAC containing the gene targeting construct.

The modified BBPAC TKO construct can be prepared in milligram quantities and linearized as described above. The linearized DNA then is introduced into the fertilized zygote by a standard protocol, e.g., pronuclear injection (Hogan et al., (1986) supra). The transgenic animal is then identified by standard Southern blots. The gene targeting event can be further identified by digesting DNA of the transgenic animal with appropriate enzymes, such as enzyme X, (FIG. 7) and probed with the flanking KO probe (FIG. 7). Mice with the targeting event will have an additional band of the appropriate size. Such gene targeting events can further be confirmed by expression of the GFP or LacZ marker gene in the expression pattern of the targeted endogenous gene, since the construct is designed to trap the endogenous promoter.

The TKO method has important ramifications in the field of vertebrate genetics. It enables gene targeting in many organisms that do not have ES cells, such as zebra fish, rats and other mammals. This will help to generate better animal models for human diseases (e.g., rats and monkeys), or to create genetically targeted animals suitable for organ transplants (such as pigs or baboons) or for commercial reasons (e.g., leaner pork or beef). This method also has additional advantages, even for gene targeting in mice. For example, this method will automatically provide germline transmission, since transgenic animals are rarely chimeric. It also enables targeted mice in strains other than the 129 strain to be obtained, and avoids the expensive and time-consuming out-breeding protocols.

In still another aspect of the present invention, methods of performing gene targeting in somatic cells using BBPAC targeting constructs are provided. Since gene targeting in somatic cells is also dependent on the length of homology, using large DNA targeting construct also improves the targeting rate in somatic cells. The experimental design in this case is similar to that with the ES cells described above. Somatic cell gene targeting is useful in gene therapy, for example, in a targeted insertion of a functional gene in a hereditary disease of the hematopoietic system. Such methods are also useful to generate targeted cell lines for experimental purposes.

The present invention further provides alternative methods of utilizing BBPAC transgenic analysis for the characterization of specific genes and their encoded protein products. In a particular aspect of the invention, ESTs are selected from mammalian UniGene sets. The EST clones are used for the identification of BBPAC clones (preferably BAC clones) containing the genes of interest. The gene expression and protein localization in selected animals can then be analyzed and these data can then be tabulated. Specific BAC/EGFP or P-lactamase constructs for example, can also be used to prepare cell specific probes for gene expression analysis using chips or arrays. The isolation of these cell types can be achieved using fluorescence activated cell sorting (FACS). cDNA probes can also be prepared from these cell types and they can be hybridized to cDNA arrays or chips. The application of these methods can be also used to characterize cell specific changes in gene expression in selected biological paradigms or transgenic models of human disease.

Therefore the present invention also includes the use of marker insertion into BBPACs clones and transgenic analysis to precisely map the patterns of expression of tissue (or system, such as the CNS) specific genes including through determining the localization of their protein products. The method can include the utilization of the human and mouse UniGene projects as informatics engines for the identification of genes that are predominantly expressed in a particular tissue or system. The UniGene databases compile "sets" or "clusters" of EST sequences to identify those representing a single gene, and collate information about these genes into an easily accessible online database. For example, the human project has incorporated EST sequences from 150 cDNA libraries prepared either from brain tissue or CNS derived cell lines, and organized these data in the "Genome Anatomy Summary" according to sites of expression of each cluster of cDNAs. The "Digital Differential Display (DDD)" project is a "computational method for comparing sequence-based gene representation profiles among individual cDNA libraries" and it results in the classification of genes present in these libraries into useful categories. Thus, in the Genome Anatomy Summary under "Brain", there are 152,160 EST sequences isolated from 163 brain cDNA libraries, generating 737 "tissue-specific" and 2,177 "tissue unique" sets of ESTs. Most of the "sets" represent novel, unexplored genes. Specific notes on possible homologies of these clusters with known proteins, notes on chromosomal positions of the ESTs, the presence of possible repetitive sequences, etc. are also included.

The present invention further provides methods preparation of transgenic mice with the modified BBPACs of the present invention. In a particular embodiment 4 founders for each BAC are generated so that the expression patterns can be analyzed at e13, P0, P9, and adult stages. Data for the P9 and adult stages can be obtained directly from founders since they can be identified prior to these ages. Data for e13 and P0 mice will require one round of breeding to generate F1 animals. The founder(s) chosen for breeding are preferably males to maximize the yield of F1 progeny. For the e13 time point, pregnant females can be sacrificed, embryos typed and analyzed. P0 animals from additional litters can also be sacrificed, typed and analyzed. At least two transgenic F1 progeny from each strain can be allowed to age to detect any apparent phenotypes due to increased gene dosage due to integration of multiple copies of the BAC (see Example 2, below). The BBPACs obtained can be used in many ways including to make further modifications (e.g., cre insertion, or generation of dominant negative mice, etc.) or to isolate specific cell types and/or to characterize cell types in slice preparations The present invention further provides methods of analysis of marker gene expression patterns and localization of epitope tagged protein products. Thus there are many options for visualization of the marker gene expression pattern. One such procedure is to perfuse in 4% paraformaldehyde, dissect the brain, postfix in 4% para, cryoprotect in 10% PVP, 4% sucrose, freeze in OCT, section at 40 microns, and float sections on PBS for direct visualization or processing for immunofluorescence. Direct visualization is effective for GFP, as is immunofluorescence with AGFP antibodies. If the expression level is very low, it is sometimes advantageous to amplify the signal using immunoflourescence. In a particular embodiment the sections can be processed for immunofluorescence with the myc epitope tag f, double immunofluorescence or direct visualization combined with immunofluorescence for the myc tag. Alternatively, vectors using β-lactamase as the marker gene can be constructed to assess whether this is advantageous for detection.

The sections chosen for analysis should be optimized to obtain the most information in the least number of images. One procedure entails collecting lateral, midsaggital and medial sections from each developmental stage and recording digital images for each of these time points. Images can be saved at both low and high magnifications to record the generalized expression pattern, the morphology of cells expressing the marker, and the localization of the epitope tagged protein in individual cells. One half of a brain can be used to run a Western blot to determine the size of the epitope tagged protein.

As disclosed herein, the epitope tag is placed on the carboxyl-terminal amino acid. However, the epitope tag can also be placed in other positions of the protein being expressed. For example, certain classes of proteins will not be properly localized if the epitope tag is fused to the C-terminus, e.g., the terminal three amino acids of many receptors are critical for interaction with scaffolding proteins carrying PSD domains [Korneau et al., Science 269:1737–1740 (1995)]. In this case insertion of the epitope tag just N-terminal to these crucial C-terminal amino acids can be performed. Thus in cases where the UniGene set reveals a probable C-terminal assembly site, a consensus site for GPI linkage, etc., specific primers can be designed to insert the epitope tag at an alternative position in the protein. In addition, the present invention provides a multiplex approach that utilizes multiple markers and allow analysis of several genes in each transgenic animal strain.

Conditional replication shuttle vectors that encode a RecA-like protein are also provided by the present invention. The RecA-like protein can be controlled by either an inducible promoter or a constitutive promoter. The conditional replication shuttle vector is preferably a temperature sensitive shuttle vector (TSSV), though for large scale procedures, the use of the R6Kγ DNA replication origin along with the pir replication protein may be used instead [see above]. In one such embodiment the conditional replication shuttle vector contains both a gene that confers tetracycline resistance and a RecA-like protein that is recA. In a particular embodiment, the conditional replication shuttle vector is a TSSV such as the pSV1.RecA having the ATCC no. 97968.

Independent origin based cloning vectors that contain a gene of interest that has been modified by the methods of the present invention are also included in the present invention. More particularly such independent origin based cloning vectors have undergone homologous recombination with a conditional replication shuttle vector in a RecA⁻ host cell, wherein the conditional replication shuttle vector encodes a RecA-like protein. In a preferred embodiment the independent origin based cloning vector has undergone homologous recombination in a RecA⁻ host cell with a temperature sensitive shuttle vector encoding a RecA-like protein. In a preferred embodiment the modified independent origin based cloning vector is a BAC that has undergone homologous recombination with the temperature sensitive shuttle vector pSV1.RecA having the ATCC no. 97968.

As discussed above, the present invention further provides methods of generating animal models for diseases associated with and/or due to a dominant allele. One such model is for Huntington's disease which has recently been generated with a YAC construct [Hodgson et al., Neuron 23:181–192 (1999)]. As disclosed herein, the BBPACs modified by the methods of the present invention are superior to the YACs since the BBPACs of the present invention can be generated with a higher cloning efficiency, have a higher stability, and have minimal chimerism. Such an animal model can be generated by placing BBPAC into an animal zygote, wherein that BBPAC contains a nucleic acid that has undergone homologous recombination, in a RecA⁻ host cell, with a conditional replication shuttle vector that encodes a RecA-like protein. Since the BBPAC can contain the entire gene encoding a particular protein, (which depending on the particular animal model desires can comprise a particular mutation), the gene can be expressed in the cells of the animal model that it is normally expressed in the disease.

In short, a mutation is identified in a gene that has been linked to a particular disease. A BBPAC library is screened for the wildtype gene (e.g., with a nucleic acid probe, or by computer searching). The precise alteration/modification of the gene is performed by a homologous recombination procedure disclosed herein using a conditional replication shuttle vector of the present invention. The resulting modified BBPAC is isolated and then placed into an animal thereby forming the animal model (e.g., injecting into the nucleus of a zygote). In a particular embodiment, the BBPAC further comprises a marker so as to readily identify animals that contain the BBPAC.

In one particular embodiment the conditional replication shuttle vector is a TSSV. In a particular embodiment of this type, the TSSV is pSV1.RecA having the ATCC no. 97968. In a preferred embodiment, the nucleic acid is introduced into the animal by pronuclear injecting the BBPAC into a fertilized zygote and thereby forming the animal model.

Any dominant allele can used to generate the corresponding animal model for the disease. Such dominant alleles include but in no way is limited to: huntingtin (htf) involved in Huntington's Disease [Hodgson et al., *Neuron* 23:181–192 (1999)]; PKD2 involved in polycystic kidney disease [Makowitz et al., *Am. J. Physiol.* 277:F17–F25 (1999)]; CACNA1A involved in Familial hemiplegic migraine [Carrera et al., *Neurology*53:26–33 (1999)]; the RP1 gene involved in retinitis pigmentosa [Guillonneau et al., *Hum. Mol. Genet.* 8:1541–1546 (1999)]; and presenilin-1 (PSEN1) involved in Alzheimer's Disease [Jonghe et al. *Hum. Mol. Genet.* 8:1529–1540 (1999)]. In one such embodiment, the BBPAC comprises a mutant huntingtin (htt).

Any non-human animal can be used for the animal model, including standard laboratory rodents such as mice, rats, rabbits, and guinea pigs; farm animals such as sheep, goats, pigs, and cows; and higher primates such as monkeys, and the great apes such chimpanzees and gorillas. The non-human animals are also part of the present invention.

High Throughput Procedures

The present invention further provides a method of preparing modified IOBCVs, e.g., BBPACs that can be used in high throughput procedures. Such high throughput procedures are invaluable for gene mapping, for example. Indeed, such high throughput procedures can be used to readily generate high resolution atlases of gene expression in specific organs and tissues which involve thousands or even tens of thousands of genes.

Thus, one aspect of the present invention allows the labeling of specific gene products including placing epitope tags and/or visually detectable labels (e.g., green fluorescent protein, LacZ, and tau-LacZ) on the gene products. Such labeling allows the expression of the gene to be monitored. In addition, the present invention permits phenotypic analysis, see Example 2. Importantly, the high throughput procedures disclosed herein also provide a means to rapidly and reliably increase the gene copy number of a large number of individual genes by rapidly generating the appropriate BACs. Such methodology is particularly helpful when studying a specific pathway, disease and/or organ or tissue. In addition, this methodology permits archiving such modified BAC constructs for local reinjection and regeneration of a particular transgenic animal rather than warehousing expensive animal strains (e.g., transgenic mice) for long periods in a central facility.

One such high throughput method is based on a series of plasmids constructed for allele replacement into the bacterial chromosome. In one particular embodiment, the vector contains a protein-dependent origin of replication, e.g., pLD55, which comprises the R6Kγ origin of replication. The R6Kγ origin is completely dependent on the pir gene, which is not carried in the BAC strains [Metcalf et al., *Plasmid* 35:1–13 (1996), the contents of which are hereby incorporated by reference in its entirety; Shizuya et al., *PNAS*, 89:8794–8797, (1992)]. Therefore, cloning into the shuttle vector can be carried out in a pir+bacterial strain in which the shuttle vector can be propagated effectively. The R6Kγ origin of replication allows growth at a high copy number in strains that express the pir protein, ie., contain the pir gene. This is advantageous both because it is very simple to obtain large amounts of DNA for cloning into this vector and because the plasmid cannot persist on its own in the BAC strain. A nucleic acid encoding a recombination protein, e.g., the recA gene, can be inserted into the pLD55 forming the pLD55.recA, for restoration of homologous recombination in the BAC strain as disclosed above.

Importantly, conditional replication shuttle vectors that have a R6Kγ origin of replication are not replicated during or following the homologous recombination step between the conditional replication shuttle vector and the BAC. This is because the R6Kγ origin of replication has an absolute requirement for pir to replicate and the homologous recombination step takes place in the BAC strains, which do not express pir. This means that there is no further replication of the conditional replication shuttle vectors that comprise a R6Kγ origin of replication in BAC strains. In fact, it was surprising that these shuttle vectors could successfully support transient homologous recombination without replicating in the cells in which the homologous recombination was occurring. This result is also in distinct contrast with conditional replication shuttle vectors having a temperature-sensitive origin of replication, since a small but significant percentage of temperature-sensitive vectors that can replicate at 30° C. and supposedly cannot replicate at 43° C., still replicate at 43° C.

The lack of independent shuttle vector replication is important since it significantly increases the percentage of cells that will comprise the vector-BAC cointergrate, after the cells are grown under conditions that require the presence of both the BAC and the shuttle vector. Indeed, this high efficiency makes it practical to modify BACs as disclosed herein, in liquid media rather than on plates. Furthermore, it is the use of a liquid media that makes it possible to modify numerous different BACs at one time. Thus the Ori R6Kγ conditional replication shuttle vector takes advantage of an analogous selection system as disclosed herein for the temperature sensitive conditional replication shuttle vector, but is far more preferable for liquid media high throughput procedures.

In one particular embodiment the vector also comprises the tet R and amp R selectable markers. Preferably a more robust tet R gene is used since the allele present in the original pLD55 vector was not optimal for the fusaric acid negative selection that is used in the resolution step of the BAC modification procedure, yielding pLD55.recA.tet. This vector thus carries both the recA gene and selectable markers used in the BAC modification protocol disclosed herein, and in a particular embodiment merely substitutes the original temperature-sensitive plasmid origin taught herein with the conditional R6Kγ origin [Metcalf et al., *Plasmid* 35:1–13 (1996)].

When this shuttle vector is electroporated into the BAC strains, as stated above, it absolutely cannot replicate since the BAC strains do not express the pir protein. Thus, the only way the BAC strain can contain both the chloramphenicol resistance and the tetracycline resistance markers (other than do to potential background, see below) is if the shuttle vector integrates into the BAC episome forming the cointegrant that is sought (the BACs contain a chloramphenicol resistance gene).

There are three reasons for generating potential background. The first is dependent on the efficiency of the negative selection for the conditional replication shuttle vector, i.e., whereas the R6Kγ origin of replication yields a background of $10^{-8}$, the temperature-sensitive origin produces a background of $10^{3}$–$10^{-4}$. Thus, the use of the R6Kγ origin of replication very significantly reduces the background. The second form of background is due to the cointegration of the conditional replication shuttle vector into the host cell DNA by undesired homologous recombination. The third form of background is due to the conditional replication shuttle vector integrating into either the IOBCV or more likely, the host cell DNA by random recombination. The latter two factors are less significant than the first, which has been overcome by the use of the R6Kγ origin of replication as disclosed herein.

One such protocol can include:
1. Preparation of competent cells from the BAC.
2. Electroporation of the shuttle vector into the BAC strain; (preferably two separate vials).
3. Selection in liquid culture in high ampicillin (e.g., 100 ug/ml).
4. Dilute 1:1000, selection again in high ampecillin.
5. Preparation of BAC DNAs.
6. Assaying cointegrant by PCR.

Preferably two separate vials are electroporated for each BAC strain.

Preferably a streamlined version of the vector containing only the tetr, oriR, and recA genes is used. The Ori R6Kγ conditional replication shuttle vector can also carry a marker cassette containing a myc tag in all three reading frames followed by a stop codon, and/or an IRES/EGFP/polyA gene for creation of a fusion transcript expressing enhanced green fluorescent protein from an internal ribosome entry site (IRES). In a particular embodiment LoxP sites can surround the vector sequences.

One protocol for BAC modification using this Ori R6Kγ conditional replication shuttle vector is as follows:
1. Prepare competent cells from four independent BAC isolates.
2. Electroporate with pLD55 3'trap vector.
3. Select for growth in liquid culture containing chloramphenicol and tetracycline.
4. Dilute culture, repeat selection.
5. Miniprep DNA, cleave with Not1 (introduced by the pLD55 3'trap cointegration); select clone with gene located in the center of the BAC.
6. Prepare competent cells and transform 2 vials with pWM91/cre.
7. Plate on fusaric acid plates to select against BACs that still carry the tetR marker.
8. Prepare DNA and PCR assay for appropriate modification.
9. Midiprep modified BAC clone and prepare for transgenesis.

Using such a procedure, modification and characterization of multiple BACs can be performed in a relatively short period of time. Furthermore, this protocol can be fully automated by changing the fusaric acid selection from plates to liquid culture if the project is to be scaled up for all expressed genes of a particular tissue or system. Preferably, the counterselection marker used can be the SacB gene. The SacB gene encodes levansucrase, an enzyme that converts sucrose to levan, which is toxic to the host cells [Frengen et al., *Genomics* 58:250–253 (1999)].

To further increase the efficiency of the cointegration and resolution, a more preferred strategy has been developed that allows for high throughput liquid modification and resolution of a BBPAC, (e.g., a BAC see Example 3). This method can employ a BAC shuttle vector that has been adapted from the shuttle vectors described above. Again, this particular vector can be modified from PLD55, and can contain a R6Kγ DNA origin of replication. As indicated above, the vector containing a R6Kγ DNA origin of replication can only replicate in bacteria expressing the pir replication protein, but it cannot replicate in DH10B, the host for the BACs. Therefore, it will not persist on its own in the BAC strains. The vector also encodes a recombination protein, such as recA, which is used to transiently allow homologous recombination in the otherwise recombination deficient bacterial cells. The cointegrates can be achieved through homologous recombination of the selected nucleic acid sequence inserted in the A box of the shuttle vector with the nucleotide sequence of the BAC (see Example 3). In a preferred embodiment, the shuttle vector is designed to contain a specific drug resistant gene, such as Ala, which provides ampicillin resistance. The cointegrates thus can be selected by growing the cells in LB media supplemented with the corresponding antibiotic, e.g., ampicillin. The double Ampicillin/Chloramphenicol resistant colonies (a chloramphenicol resistant gene is on the BAC) should contain the homologously recombined plasmids. The BAC shuttle vector is constructed to also contain the positive counterselection marker, e.g., a SacB gene, which is lost upon final resolution (see FIG. 22). The SacB gene product, levansucrase, converts sucrose to levan, which is toxic to the host cells. Thus the SacB gene facilitates the selection of resolved BAC clones when the media contains sucrose since unresolved BAC cointegrants still retain the counterselection Sac B gene and are therefore, selected against when grown in media containing sucrose. A marker gene, IRESEGFP can also be introduced into the shuttle vector, which contains the ribosome entry site (IRES) and expresses enhanced green fluorescent protein. Analyses of the expression of EGFP gene in transgenic mice, for example, allows the individual gene expression pattern to be observed.

Preferably, AscI and SmaI sites are also included in the shuttle vector preceding the marker gene. These two sites allow a selected nucleic acid sequence to be readily inserted in the A box of the shuttle vector allowing the preparation of the shuttle vector for directional cloning, see Example 3, with very little background due to failure of the recircularization of the vector.

Figure 20:
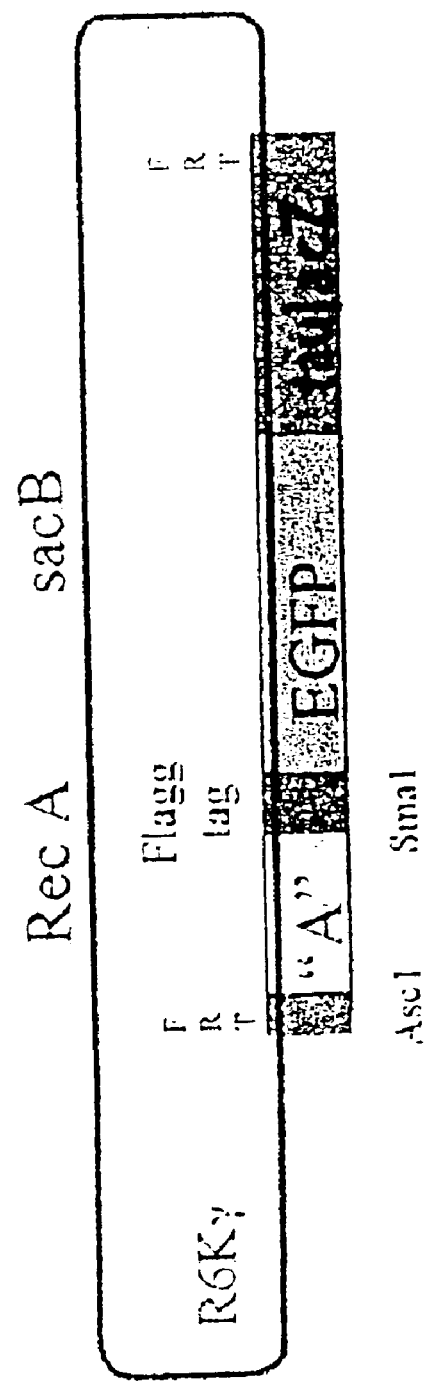
FIG. 20 depicts a conditional replication shuttle vector that comprises a gene encoding Rec A, a gene encoding the enzyme levansucrase (sacB), the R6Kγ origin of replication, the two restriction sites Asc1 and Sma1, an "A" Box, nucleic acids encoding an enhanced green fluorescent protein (EGFP) and the epitope tag (FLAG), tau lacZ and two FRT sites.

"A box" amplification: A selected nucleic acid sequence, i.e., a homology region, from a gene of interest contained by an IOBCV (e.g., a BAC) can be amplified by PCR using one or more specific primers. The amplified PCR product can then be placed into a conditional replication shuttle vector as indicated in FIG. 20 in the "A box". Thus, once a gene has been selected for analysis, the first step in BAC modification is to design oligos for amplification of an approximately 300–500 basepair segment of the BAC. In the Example below, (Example 3) the 3' UTR region of the gene of interest was used for the preparation of the selected nucleic acid sequence to be placed in the A box. The oligonucleotides can be designed to include an Asc1 site at the 5' end of the amplified fragment because the shuttle vector (SV) is designed for very highly efficient and directional cloning of the "A box" fragments into an Asc1/Sma1 cleaved shuttle vector. The PCR amplification of the "A box" can be done from any genomic DNA that is contained by an IOBCV (e.g. a BAC), including the DNA from C57BL/6J mice exemplified in Example 3 below. This ensures that the "A box" is isogenic with the BAC DNA (e.g., from the BAC library RPCI 23 used in Example 3 below).

Cointegrates are selected after homologous recombination: As in the methods described above, each shuttle vector is transformed into an individual BAC containing strain. Homologous recombination can then occur between the shuttle vector and BAC. However, since the shuttle vector contains the R6Kγ origin, it cannot replicate in the BAC host cells, DH10B. Therefore, the selection for both the chloramphenicol marker on the BAC and the ampicillin marker on the shuttle vector yields only those colonies in which the cointegrates have been produced (other than the small background discussed above). The advantage of the R6Kγ is that it allows a dramatical improvement in the efficiency of the BAC modification procedure. Furthermore, the entire selection process can be done in a liquid culture simply by serial dilution (see Example 3).

Screening the resolved clones from the modified BACs: To improve the efficiency for removal of the shuttle vector from the cointegrates to generate the modified BACs, several different strategies can be employed. Two are exemplified herein. One strategy uses an integration/excision system, e.g., excision by flip recombinase [Hoang et al., *Gene* 212:77–86 (1998), the contents of which are hereby incorporated by reference in their entirties] which employs a broad host range Flp-FRT system for site specific excision of DNA sequences integrated into the bacterial chromosome. The other employs an integration/resolution methodology as detailed below. Either way, it is preferred that the system is readily adaptable for use in liquid culture.

The first step in either modification procedure occurs by homologous recombination through the approximately 500 basepair homologous "A box", discussed above to produce the cointegrate carrying both the marker and the shuttle vector sequences within the BAC. During this step the cells are grown in ampicillin and chloramphenicol to select for both the shuttle vector and the BAC. In this particular system, the R6Kγ origin of replication in the shuttle vector cannot operate in the BAC strain and the shuttle vector plasmid cannot persist on its own. Thus, the only way to obtain stable antibiotic resistance to both ampicillin and chloramphenicol is for the shuttle vector to integrate into the BAC or the host chromosome. Using this strategy, the cointegration can be upwards of 70% efficient with respect to the desired product and all of the selections could be transferred to liquid culture. This allows this step to occur in 96 well plates (or larger) so that concurrent modification of a large number of constructs can be achieved.

Figure 22:
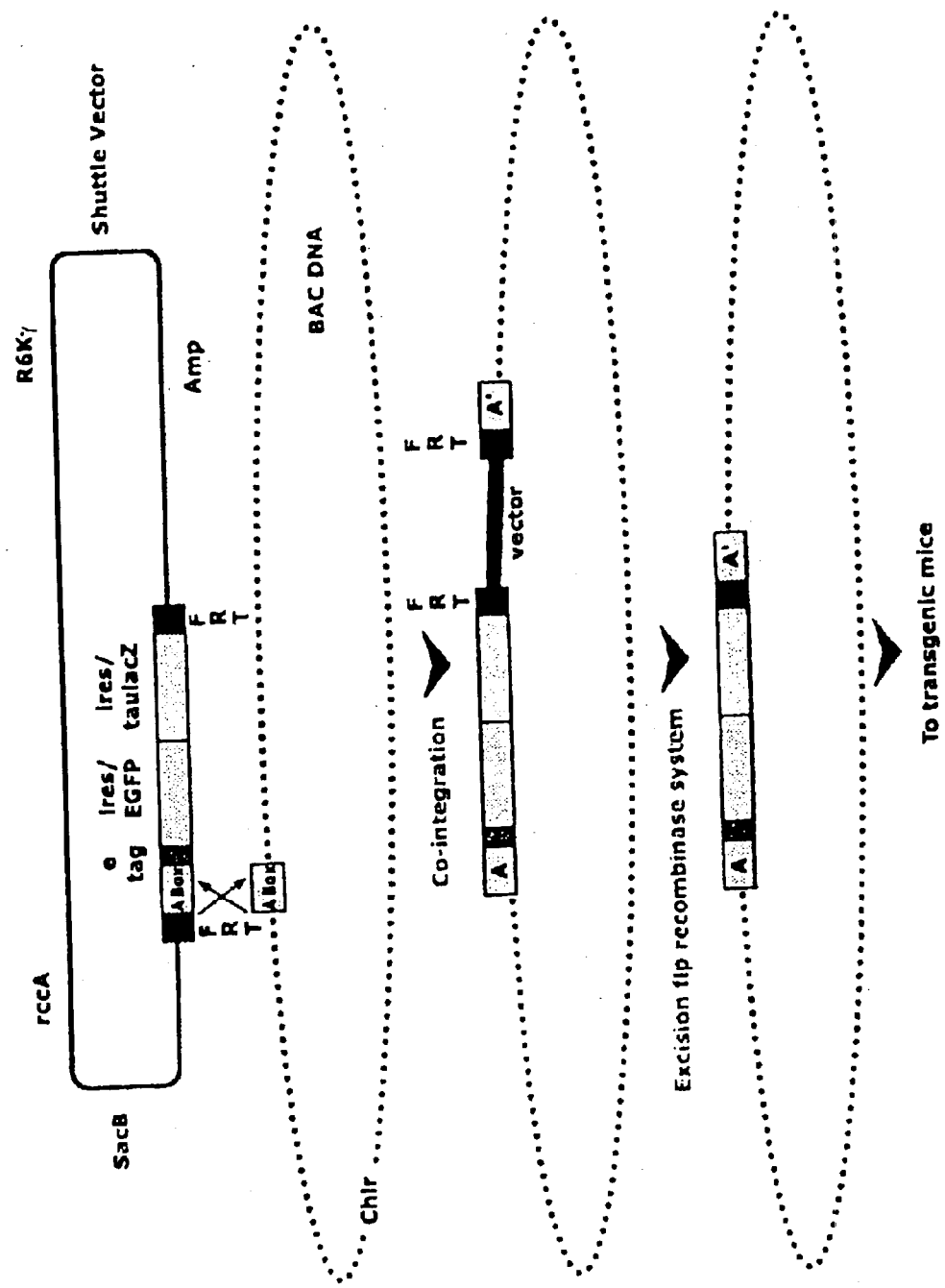
FIG. 22 depicts a schematic drawing of a procedure for using a conditional replication shuttle vector to modify a BAC, culminating in using the modified BAC to make transgenic mice. This procedure includes the expression of flp recombinase within the cells containing the cointegrate to excise the shuttle vector sequences [Hoang et al., Gene 212:77–86 (1998)]. The flp recombinase works via the "frt" sites surrounding the shuttle vector.

The next step in the first procedure is to express flp recombinase within the cointegrate containing cells to excise the shuttle vector sequences (see FIG. 22). The flp recombinase works via the "frt" sites surrounding the shuttle vector and it is highly efficient for excision [Hoang et al., *Gene* 212:77–86 (1998)]. At the same time, a powerful negative selection of sucrose can be used relying on the SacB gene product. In this case, therefore, those cells that did not excise the shuttle in the flp recombinase step cannot grow, allowing the efficiency of the resolution process to be greater than 25%. It is particularly noteworthy that those cointegration events that occur inappropriately into the bacterial genome instead of the BAC are also selected against in this step of the procedure. This is because if integration occurs outside of the "A box" the resultant product retains frt sites surrounding the marker. Therefore, in these cases the excision step deletes the marker instead of the vector sequences, leaving the Sac B gene in the chromosome. This marker is then selected against in the sucrose, resulting in the death of cells carrying the aberrant recombination events.

The particular system allows all of the manipulations of the BACs to be performed in liquid culture, with exception of the last step, which requires growth on plates. Furthermore, the increased efficiency of the cointegration step and the selection against unwanted products in the excision procedure has eliminated the need to identify proper cointegrates before proceeding with the resolution phase. Operationally, this has resulted in a simplified method that is well suited to the generation of more than twenty BAC constructs per week. Finally, it is important to note that this new strategy is composed of very well established techniques for highly efficient allele replacement in *E. coli* (see Example 3).

Figure 23:
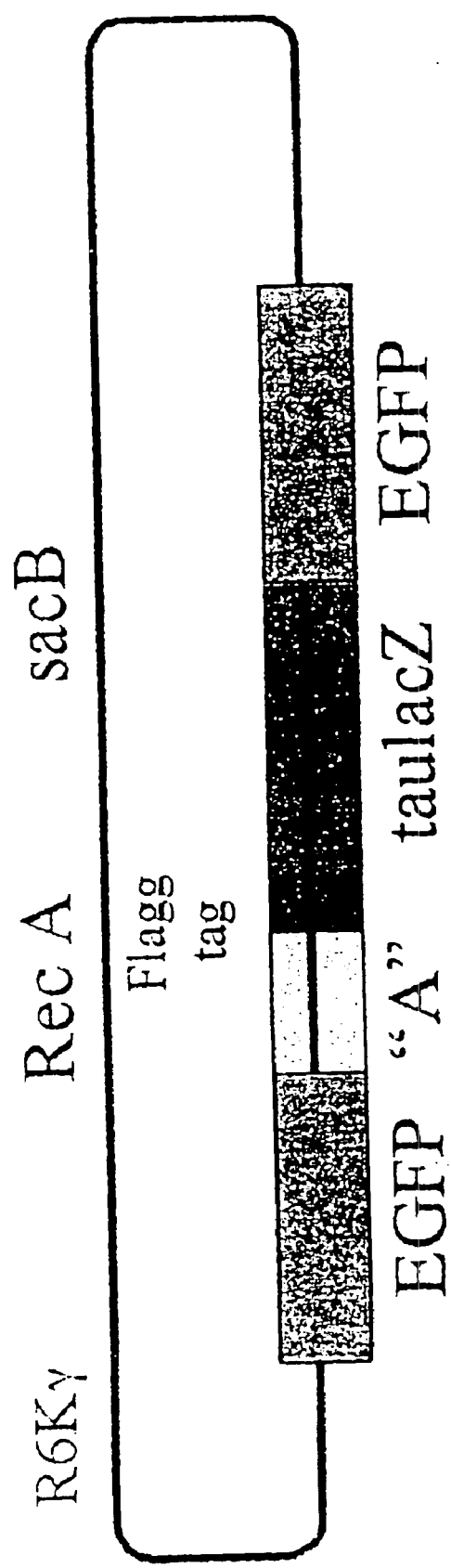
FIG. 23 depicts a conditional replication shuttle vector that comprises a gene encoding Rec A, a gene encoding the enzyme levansucrase (sacB), the R6Kγ origin of replication, an "A" Box, tau lacZ, a nucleic acid encoding the epitope tag (FLAG) and two copies of a nucleic acid encoding an enhanced green fluorescent protein (EGFP).

An alternative protocol employs an integration/resolution methodology, as the RecA activity is further exploited to allow an additional recombination step to complete the resolution of the modified IOBCV (e.g., a BAC). In this protocol the shuttle vector is constructed to contain two homologous sequences that are homologous to each other, but not homologous to the BAC. In Example 3 below, a second copy of IRESEGFP is used (see FIGS. 23 and 24). The first homologous recombination event occurs through the homologous nucleic acid of the "A box" to form the shuttle-vector-BAC cointegrate, whereas the second homologous recombination event serves to resolve out the vector sequence. In Example 3 below, the IRESEGFP sequence is much larger than the A box homology sequence that is used for the cointegration, and therefore, the resolution step occurs with much greater frequency through the IRESEGFP sequences (see Example 3). Thus, it is preferred that the two homologous sequences that are homologous to each other, but not homologous to the BAC be longer than the selected nucleic acid sequence in the A box.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Homologous Recombination Based Modification in *E. coli* and Germline Transmission in Transgenic Mice of an 131 Kilobase Bacterial Artificial Chromosome Introduction Bacterial based artificial chromosomes, such as Bacterial artificial chromosomes (BACs) and P-I derived artificial chromosomes (PACs), are circular bacterial plasmids that may propogate as large as 300 kb of exogenous genomic DNA [Shizuya et al., *PNAS*, 89:8794–8797, (1992); Ioannou et al., *Nature Genet.*, 6:84–90 (1994)]. For the majority of BAC and PAC libraries, the average size of the insert is 130–150 kb. There are several advantages of using bacterial based artificial chromosomes for genomic and functional studies, compared to the yeast based system (i.e. YACs): First, BAC and PAC libraries are much easier to construct due to higher cloning efficiency. Second, BACs and PACs are propagated in recombination deficient *E. coli* host cells, so they have high stability and minimal chimerism. No rearrangements have been observed in BACs or PACs after 100 generations of growth. Third, isolation of BAC and PAC DNA is very easy since they exist as supercoiled circular plasmids that are resistant to shearing. Conventional bacterial plasmid DNA isolation methods can be applied to obtain milligrams of intact BAC or PAC DNA. Finally, direct DNA sequencing can be applied to BAC or PAC DNA, which is not possible for YAC DNA. These advantages have made BACs and PACs important tools for genome studies in many species.

Although BBPACs are useful for physical mapping in genome studies, no simple method is available to modify BBPACs, as is available for the YACs. A simple homologous recombination based BBPAC modification method is disclosed, termed targeted BBPAC modification (See FIG. 7 for a schematic representation of the method). This method allows precise modification, such as marker insertion, deletion, point mutation, at any chosen site within a given BBPAC. This method involves several steps: isolation of BBPACs using cDNA or genomic DNA probes, simple mapping and partial sequencing of the BBPACs, cloning of the shuttle vector, targeted modifications, pulsed field gel analyses of the modified BBPACs, and finally preparation of linearized BBPAC DNA for functional studies, such as pronuclear injection to produce BBPAC transgenic mice. Since the method is simple and reliable, it is reasonable to expect that the entire procedure, from the step of screening for a BBPAC with a cDNA or genomic DNA probe to the step of modified BBPACs ready for functional studies, can be completed within 6–8 weeks.

Using this method, the IRES-LacZ marker gene has been introduced into an 131 kb bacterial artificial chromosome (BAC) containing the murine zinc finger gene, RU49. No rearrangements or deletions are detected in the modified BACs. Furthermore, transgenic mice are generated by pronuclear injection of the modified BAC and germline transmission of the intact BAC has been obtained. Proper expression of the lacZ transgene in the cerebellum has been observed, which could not be obtained with conventional transgenic constructs. In summary, a novel and efficient method has been developed to modify BACs, PACs and P1 for in vivo studies of gene expression and gene function.

Materials and Methods
1. Isolation and Initial Mapping of BACs
(I) BAC Isolation (3–4 Days):

A BAC clone is isolated with either a unique cDNA or genomic DNA probe. BAC libraries for various species, (in the form of high density BAC colony DNA membrane) are available from Research Genetics, Inc. and Genome Research, Inc. The mouse 129 genomic BAC library from Research Genetics has proved to be a good source for genomic DNAs. To avoid damage to the membrane, the probe is first tested on a mouse genomic Southern blot to ensure that the probe does not contain any repetitive elements. The library is screened according to manufacture's direction. The positive clones can be obtained from the company within a few days.

(II) Preparation of Bidiprep BAC DNA by Alkaline Lysis Method (1 Day):
Reagents:
1. Solution I: 50 mM glucose, 25 mM Tris.HCl (pH 8.0); 10 mM EDTA (pH 8.0)
2. Solution II: 0.2N NaOH, 1% SDS (0.4 g NaOH, 45 ml ddH20, 5 ml 10% SDS).
3. Solution III: 5M KOAc (60 ml), glacial acetic acid (11.5 ml), H20 (28.5 ml).
Protocol:
1). Inoculate each BAC containing bacterial to 50 ml LB containing 12.5 ug/ml chloramphenicol. Grow overnight in 37° C.
2). Spin the overnight culture in a 50 ml Falcon tube for 20 min. at 3500 RPM at 4° C. Pour off the supernatant.
3). Resuspend the pellet in 1 ml cold solution I. Transfer the cell mix to a 15 ml polybrene centrifugation tube and place on ice for 5 min.
4). Then add 2 ml fresh (<2 weeks old) solution II. Mix well by inverting vigorously a few times.
5). Immediately add 1 ml cold solution III, mix by inverting gently several times, and place on ice for 10 min (this solution may be left overnight).
6). Spin at 10,000 rpm for 12 min. at 4° C. Transfer the supernatant to a new polybrene tube.
7). Add 4 ml Phenol (pH6.0)/Chloroform (1:1), and mix well by inverting the tube several times. Spin again at 10,000 rpm for 12 min. at 4° C.
8). Transfer the upper layer to a new tube, and add 8 ml 100% ethanol to it. Invert the tube vigorously several times to mix well. Spin at 10,000 rpm for 30 min at 4° C. It can also be kept in −20° C. for overnight prior to centrifuging.
9). Wash the pellet with 70% ethanol. Dry by vacuum and resuspend the DNA in 200 ul TE. The BAC midiprep DNA may be stored in 4° C. for months (Do not freeze the BAC DNA, since repetitive freezing and thawing will result in degradations).

(III) BAC Maxiprep DNA Preparation:
Two methods were used to prepare large quantities of RNA-free BAC maxiprep DNA. The first method is the standard cesium chloride banding method (see Maniatis, supra). This method was used routinely to obtain >500ug BAC DNA from 1 liter bacteria culture. The second method, uses a commercially available column, the Nucleobond AX-500 (made by The Nest Group, Southborough, Mass.) .The maxiprep DNA are also stored in 4° C. for long-term storage.

(IV) Mapping the BACs by Pulsed Gel Electrophoresis and Southern Blots (3–5 days):

To determine the size of each BAC and to confirm that the BAC contains the gene of interest, a simple mapping of the BACs is done. The following enzymes are used to map each BAC: Not I (to release the BAC insert), Mlu I, NotI/MluI (double digest), PmeI, PmeI/NotI and XhoI. Digestion is done in a 40ul total volume, which contains the following: 5 ul midiprep DNA, 4 ul digestion buffer, 4 ul 10×BSA(if necessary), 1 ul 100 mM spermidine(final concentration 2.5 mM), 2 ul enzyme(10–40 units), and ddH2O. Digestion is done at 37° C. for >5 hrs.

The digested BACs are resolved on a pulsed field gel (Bio-Rad's CHEF-DRII). The gel is 1% agarose in 0.5× TBE. The gel is run in 0.5×TBE. The separation condition is the following: 6 v/cm, 5s to 15s linear ramping for 15 hrs to 18 hrs at 14° C. The New England Biolab's PFGE marker I or II as the high molecular weight marker and 1 kb DNA ladder (Life Technologies Inc.) as the low molecular weight marker are used.

The gel is then stained with ethidium bromide (1 to 5000, or 1 to 10,000 dilution of 10 mg/ml stock) for 30 min prior to taking the photograph. Then the gel is blotted onto the nitrocellulose membrane and hybridized to cDNA and genomic DNA probes according to standard protocols (Maniatis, supra). To ensure the entire cDNA is included in the BAC, probes/or oligonucleotides from both the 5'end and the 3' end of the gene are used to probe the blot separately. Those large BACs containing the entire gene are usually selected for BAC modification.

2. Construction of the Shuttle Vector With the Recombination Cassette

Since targeted BAC modification is a method based on homologous recombination, homologous sequence from the BAC has to be obtained. Two homologous sequences of about 500 bp each (namely A and B, FIG. 7) is all that is needed to construct the shuttle vector for BAC modification. The homologous sequences are chosen such that a given modification (i.e. insertion, deletion and point mutation) will be introduced between A and B in the BAC. A and B can be obtained by direct sequencing of the BACs. The sequencing oligonucleotides are designed based on the cDNA sequence.

(I) Direct Sequencing of the BAC (2–3 Days):
1) If maxiprep DNA is used, go directly to step 2. If midiprep DNA is used, first add 100 ul ddH2O and 10 ul 10 mg/ml RNAse A to 100 μl midiprep BAC DNA, and incubate at 37° C. for >1 hr. (This step is critical, incomplete RNAse treatment will result in poor precipitation and sequencing).
2) Add 132 ul PEG mix (2.5M NaCl and 20% PEG 8000) to the treated DNA. Put on ice for 5 min.
3) Spin for 15 min at 4° C. Discard the supernatant. Spin again for 2 min. Completely remove the remaining supernatant, which contains the PEG mix.
4) Wash the pellet with 70% ethanol. Dry in Speedvac and resuspend in 20 ul ddH2O.
5) Run 2 ul on a agarose gel to estimate the final concentration. Usually use 6–8 ul (500 ng–1000 ng) DNA for automatic sequencing, also use 150 ng sequencing oligos.

Each sequencing reaction will result in up to a 500 bp sequence. Sequence more than one BAC for a given primer to compare the sequences. The main purpose for sequencing is to design a 20 bp PCR primer, which is about 500 bp away from the sequencing oligo (which usually is the other PCR primer), to enable PCR amplification of this genomic fragment and to clone it into the building vector. Therefore, as long as a 20 bp sequence can be identified which is at the appropriate position, and which is the same in several independent sequencing reactions, the goal is achieved. The quality of the DNA sequence in between is not very critical.

(II). Vectors Used in Targeted BAC Modification:

A two vector system is designed to construct the shuttle vector for BAC modification (FIG. 1). The first vector is a pBS.KS based building vector, which is used to construct the recombination cassette containing homologous sequence A and homologous sequence B and the modification to be introduced between them. The recombination cassette was not constructed in the pSV1.RecA shuttle vector was for the following reasons: first, it is a low copy plasmid so that it is difficult to obtain high quantity DNA; second, it is a large plasmid (11 kb), so it is relatively difficult to clone. The building vector contains the marker gene to be introduced into the BAC, cloning sites flanking it (usually EcoRI for cloning the homology A and XbaI for homology B, and rare restriction sites such as MluI, PmeI and Pac I for mapping of the modified BAC). There are two Sal I sites (or one Sal I, one XhoI) flanking the multiple cloning sites. They are used to release the recombination cassette and subclone it into the Sal I site of the pSV1.RecA vector, to complete the shuttle vector construction. One thing about designing the building vector is that there should not be any Not I sites within the recombination cassette, since NotI sites are used in the end to release the linear modified BAC for biological experiment (e.g., pronuclear injection). The map and utility of various building vectors and the shuttle vector are described below.

Figure 9:
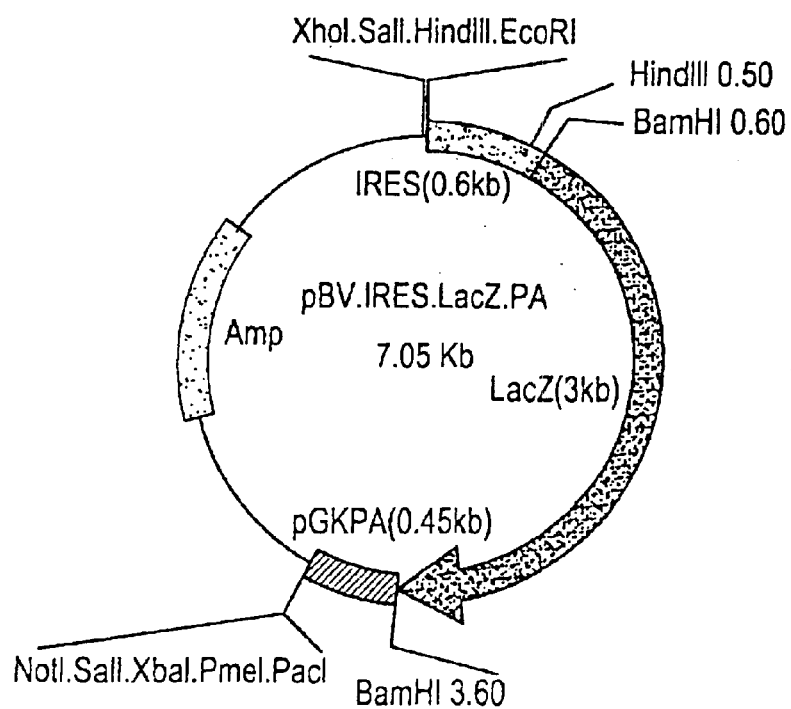
FIG. 9 is the restriction map of pBV.IRES.LacZ.PA. This vector was modified from the pWH10 vector originally constructed by Kim et al. [*MCB*, 12:3636–3643 (1992)].
Figure 10:
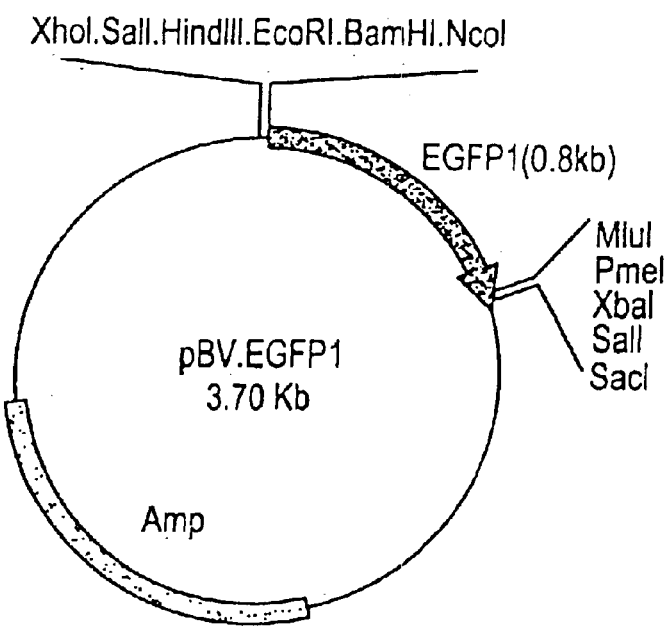
FIG. 10 is the restriction map of pBV.EGFP1. The plasmid is based on pBluescript.KS(+). EGFP1 was from Clonetech.

(A) Building Vectors (pBV) All based on pBS.KS (Stratagene)

pBV.IRES.LacZ.PA (FIG. 9) This vector is designed to introduce lacZ marker gene into a coding exon or the 3' UTR of a given gene, to study gene expression and gene regulation in vivo. IRES will enable the translation of the marker gene independent of the endogenous translation initiation codon.

pBV.EGFP1 (FIG. 10) This vector is designed to introduce the brighter version of the green fluorescent protein, EGFP1 (Clontech), into an exon of a given gene before the endogenous ATG or fused in frame with the endogenous gene. The green fluorescent protein will mark gene expression in living cells and living organisms. Since the marker gene does not contain its own polyA addition sequence, the endogenous polyA sequence is used.

Figure 11:
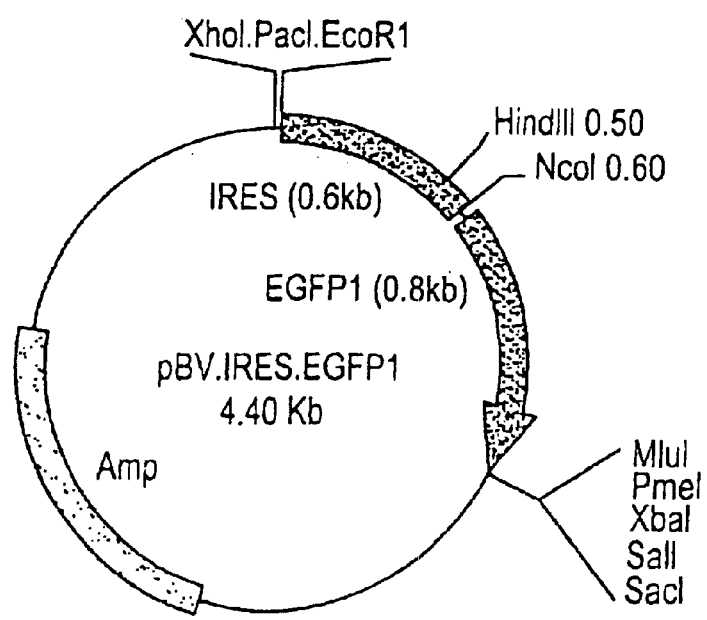
FIG. 11 is the restriction map of pBV.IRES.EGFP1. The plasmid is based on the pBluescript.KS backbone. EGFP1 was from Clonetech.
Figure 12:
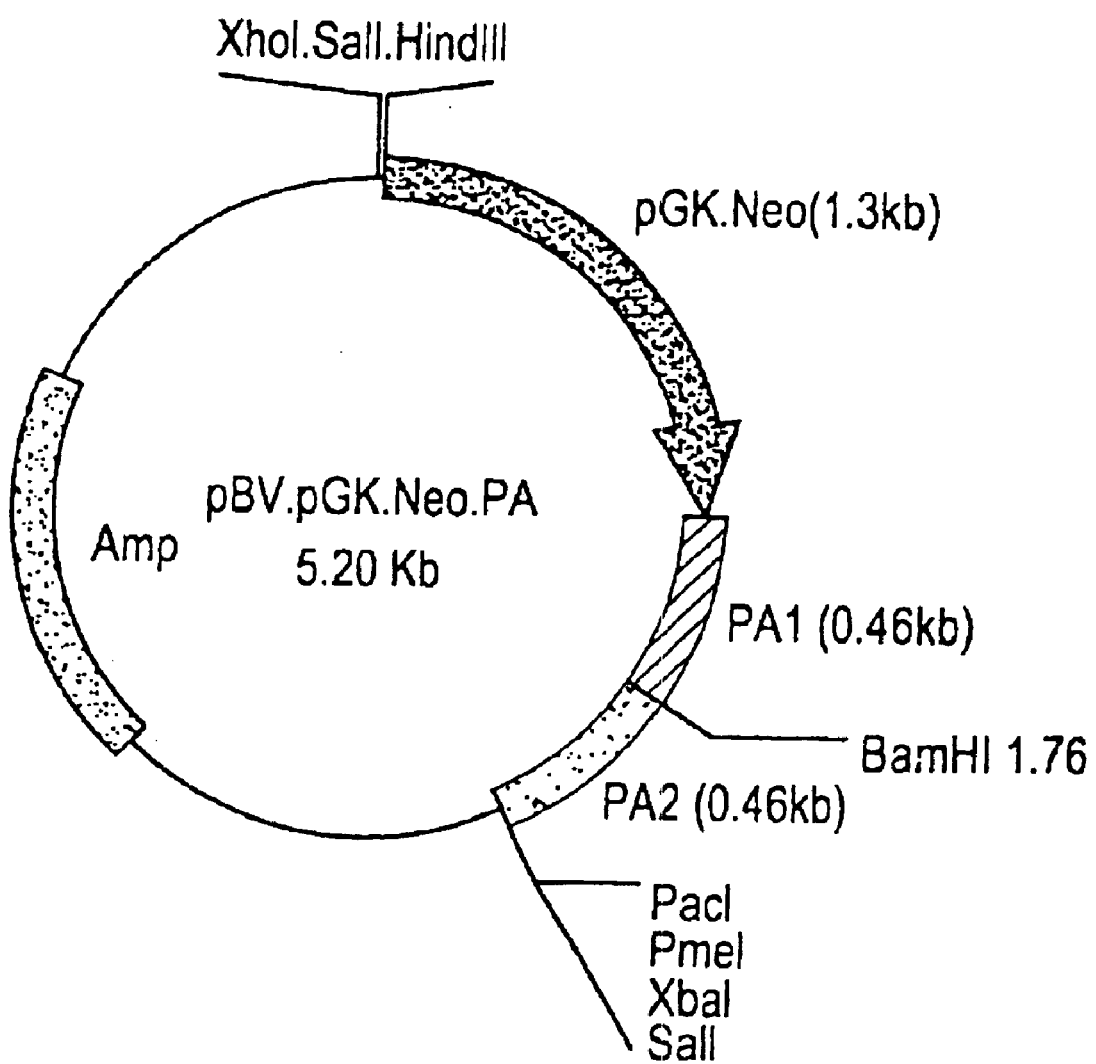
FIG. 12 is the restriction map of pBV.PGK.Neo.PA. The vector is based on a pBS.KS backbone. The pGK.Neo.PA sequences was excised from a pKS.NT vector by digestion with HindIII and BamHI and subcloned into the HindIII/Bam fragment of the pBV.IRES.LacA.PA.

PBV.IRES.EGFP1(FIG. 11) This vector is used to introduce EGFP1 gene into the coding region or the 3' UTR of a given gene, with its translation independent of the endogenous translation frame.

pBVpGK.Neo.PA (FIG. 12) This vector is designed to introduce a neo expression cassette into the BAC, containing the neo gene with the pgk promoter and the polyA addition signal. Modified BAC can be introduced into tissue culture cell lines (i.e. ES cells) to obtain stable transfected cells by selecting for neomycin resistance. This vector is particularly useful for gene targeting with modified BACs. Notice that although there are two identical pgkpA sequence at the 3' end of the neo gene, it will not interfere with the proper expression of the neo gene. The only consequence is that during BAC modification, one of the pgkPA sequence may be deleted due to homologous recombination.

Figure 8:
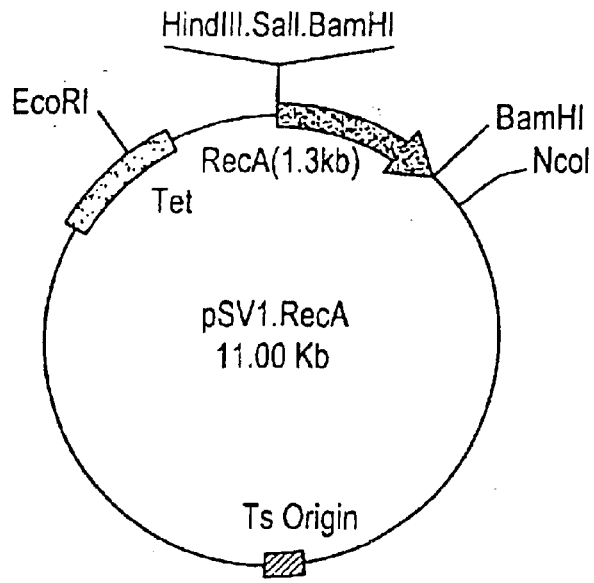
FIG. 8 is the restriction map of pSV1.RecA. This temperature sensitive shuttle vector is based on the pMBO96 vector originally constructed by M. O'Connor et al. [*Science*, 244:1307–1312 (1989)].

(B) Temperature Sensitive, Recombination Inducing Shuttle Vector (pSV1.RecA) (FIG. 8)

This plasmid vector was modified from the pMBO96 vector originally constructed by O'Connor et al (Science, 1989, Vol 244, pp.1307–1312). The pMBO96 vector was a gift from Dr. Michael O'Connor. The original vector carries tetracycline resistance, and contains a pSC101 temperature sensitive origin of replication, which allows the plasmid to replicate at 30° C. but it will cease replication and is lost at 43° C. The E. coli RecA gene was amplified by PCR and sub-cloned into the Bam HI site, to create the pSV1.RecA vector. The Sal I site is used to subclone the recombination cassette from the building vector.

(III) Cloning two PCR Amplified BAC Fragments Into the Building Vector (6–8 Days):

The first step of targeted BAC modification involves the subcloning of two small genomic fragments (A and B) into an appropriate building vector, which includes two steps of conventional sub-cloning. One should pay attention to the following points when designing the A and B fragments.

1. Each fragment should be >500 bp (the shortest attempted was 450 bp). PCR amplified fragment with appropriate restriction sites designed at the end of the PCR primer is the method of choice. Frequently, an additional restriction site is designed into one of the two PCR primers to assist in determining the orientation of the cloned PCR fragment. The relative imprecision of PCR amplification does not appear to affect the BAC modification efficiency.

2. As mentioned before, neither A nor B fragments should containing internal XbaI, EcoRI and Sal I sites, since these sites will be used for subcloning. Nor should they contain NotI sites since NotI is used to linearize the BAC 3. The orientation of the arms must be preserved as in the endogenous loci.

(IV) Subcloning the Recombination Cassette From the Building Vector Into the pSV1.RecA Shuttle Vector (4 Days):

1. Prior to cloning the recombination cassette into the shuttle vector, the following plates are usually prepared: the tetracycline (10 ug/ml) LB agar plates and the tetracycline (10 ug/ml)+chloramphenicol (12.5 ug/ml) LB agar plates. Plates are made according to standard protocol [Sambrook et al., (1989) supra].

2. Prepare pSV1.RecA and building vector midi-prep DNA by the alkaline lysis method (see above). For the pSV1.RecA vector, Qiagen columns can also be used to obtain high purity DNA, though yield is usually low. This is due to the low copy number of the PSV1 plasmid. For preparation of pSV1.RecA DNA, the culture should be grown at 30° C. in LB+tetracycline (10 ug/ml). The final midi-prep DNA is usually dissolved in 200 ul TE or ddH2O.

3. Digest 2–5 ug of the pSV1.RecA and pBV with Sal I. For pSV1.RecA, the reaction is done in 200 ul volume:
   100 µl medi-prep DNA (2–5 ug) or
   20 µl of Qiagen midi-prep of pSV1.RecA
   20 µl H buffer (Boehringer Mannheim)
   8 ul Rnase (10 mg/ml) (for alkaline lysis preps)
   10 ul Sal I (200 units, Boehringer Mannheim)
   62 ul ddH2O The reaction is performed at 37° C. for >6 hours (usually overnight), then 30 units more Sal I is added, and the digestion continue for another 1–2 hours. (Optional) A small sample of the digestion (5 ul) may be run on a gel to ascertain that a complete digestion has been achieved.
4. At the end of the digestion, Sal I is inactivated by heating to 65° C. for 15 minutes.
5. The vector is then treated with alkaline phosphatase by adding 20 ul 10×dephosporylaiton buffer, 4 ul (1 unit/ul) calf intestinal alkaline phosphatase (Boehringer Mannheim) for 30 minutes at 37° C. The enzyme is then inactivated by adding 20 ul 50 mM EDTA (to a final concentration of 5 mM), and heating at 75° C. for 15 minutes.
6. The digested pSV1 vector and pBV with recombination cassette are run on a 1% low melting Seaplaque GTG agarose at 75 V for 8–10 hours. The DNA should be run in a large well created by taping together several teeth of the comb.
7. An 11 kb linearized plasmid band should be visible on the gel for pSV 1.RecA. Cut this band and also the recombination cassette insert band from the gel. Purity these DNA fragments using Geneclean Spin columns (Bio 101, Inc.) according to manufacture's direction. Run a small portion of the purified DNA on a gel to estimate the DNA concentration.
8. Ligation reaction: Each ligation reaction is done in 20 ul total volume containing: >50 ng pSV1.vector, 100–200 ng insert, 2 ul 10× ligation buffer (Boehringer-Mannheim), 2 ul 10 mM ATP, 1 ul ligase (Boehringer-Mannheim) and ddH2O. Ligation is carried out at 16° C. overnight.
9. Transformation of DH5a competent cells with pSV1 vectors: Half of the ligation reaction (10 ul) is used for transformation, by adding to 100 ul of cold, chemical-induced DH5a competent cells. Incubate 15 minutes on ice, then heat shock at 37° C. for 2 minutes, add 1 ml LB to the tube, and shake at 30° C. for 30 minutes. The cells are then centrifugated at 6000×g for 4 minutes and the pellet is resuspended in 100 ul LB and spread onto Tet (10 ug/ml) LB agar plates. Incubate the plates at 30° C. for >15 hrs hours.
11. Pick colonies and do colony hybridization according to standard protocols [Sambrook et al., (1989), Supra], probing with a fragment derived from the pBV1, such as homology arms (A or B) or the marker gene. Positive clones are further analyzed by restriction digest, and if necessary, Southern blots.

3. Targeted BAC Homologous Recombination in Bacteria (I) Equipment
   Bacterial incubator: set either at 30° C. or at 43° C.
   Shakers: set either at 30° C. or at 43° C.

(II) Reagents and Plates
   The following reagents and plates should be prepared prior to the targeted modification experiment. All the plates can be stored at 4° C. for up to one month. Detailed methods for preparation of various antibiotic resistant plates can be found in Maniatis.
   1. Tetracycline stock solution (1000X): 10 mg/ml in 50% ethanol, wrapped in aluminum foil and stored in −20° C. for up to one month.
   2. Chloramphenicol stock solution (1000X): 12.5 mg/ml, dissolved in ethanol (>50%), stored in −20° C.
   3. Tetracycline plates (tet plates): LB agar plates containing 10 ug/ml tetracycline. Store in 4° C. and wrapped in aluminum foil to avoid the light.
   4. Chloramphenicol plates (Chl plates): LB plates contain 12.5 ug/ml Chloramphenicol.
   5. Tetracyline+Chloramphenicol plates: LB plates contain 10 ug/ml tetracycline and 12.5 ug/ml chloramphenicol.
   6. Fusaric acid+Chloramphenicol TB plates (FA+Chl plates): Prepared as following.
   First, make tryptone broth agar, or TB agar:

|  | 500 ml TB | 1 L TB |
|---|---|---|
| Tap H$_2$O(not distilled H$_2$O) | 500 ml | 1 L |
| Bacto tryptone | 5 g | 10 g |
| Yeast extract | 0.5 g | 1 g |
| Glucose | 0.5 g | 1 g |
| NaCl | 4 g | 8 g |
| 0.1 M ZnCl$_2$ | 0.25 ml | 0.5 ml |
| Chlorotetracycline (6.3 mg/ml) | 4 ml | 8 ml |
| Bacto agar | 7.5 g | 15 g |

Autoclaving the above TB. Also autoclave 500 ml of 1M NaH$_2$PO$_4$H$_2$O. After autoclave, wait till the TB agar drop to about 60° C., then add the following:

|  | 500 ml TB | 1 L TB |
|---|---|---|
| NaH$_2$PO$_4$.H$_2$O (1 M) | 36 ml | 72 ml |
| Fusaric Acid (2 mg/ml, filter ster.) | 3 ml | 6 ml |
| Chloramphenicol (12.5 mg/ml) | 0.5 ml | 1 ml |

Pour the plates and leave the plates outside overnight and then store at 4° C. There is no need to avoid the light.

(III) Making Competent BAC Containing Bacteria (1 Day):
   A chemical method is used to prepare competent cells from BAC containing bacteria host (Inoue et al, Gene 96, p23–28, 1990).
   (1) Media and Plates:
      LB+Ampicilin (50 ug/ml) agar plates;
      TB media (10 mM Pipes, 55 mM MnCl$_2$, 15 mM CaCl$_2$ and 250 mM KCl), all the components except for MnCl$_2$ are mixed and the pH is adjusted to 6.7 with KOH. Then, MnCl$_2$ was dissolved, the solution was sterilized by filtration through a 0.45 u filter unit and stored at 4° C. All salts were added as solids.
   (2) Frozen stock of BAC containing DH10B cells were taken by a metal loop and inoculated into 3 ml of LB+chloramphenicol (12.5ug/ml). Grow the culture with rigorous shaking in 37° C. for overnight.
   (3) Take 0.5 ml overnight culture, add to 50 ml LB+chloram. (12.5 ug/ml) and grow at 37° C. with rigorous shaking till an optical density at 600 nm of about 0.6 is achieved.
   (4) Place the flask on ice for 10 min. Then transfer to a 50 ml falcon tube and centrifuge at 3000 rpm for 10 min at 4° C.
   (5) Pour the supernatant. Resuspend the pellet in 16 ml ice-cold TB. Incubate on ice for 10 min, then spin again as above.
   (6) The cell pellet was gently resuspend in 4 ml of TB supplemented with 7% DMSO. Incubate on ice for 10 min, then dispense 0.5 ml aliquot and immediately frozen by immersion into liquid nitrogen. The tubes are stored in −80° C. for further use.

(IV) Co-Integrate Formation and Identification Through Southern Blot Analyses (4 Days):
1. Transform the competent BAC cells with the Ts shuttle vector, using 10 ul of the midiprep DNA and 200 ul BAC containing competent cells. Transformation is done as in (IV) of part II. Plate 1/10 of the transformed cells onto Tet+Chl plates, and grow overnight at 30° C.
2. To generate co-integrates, single colonies (up to 6 in total) are picked up with a sterilized metal loop and diluted each into 1 ml LB. Vortex to disperse the bacteria in LB. Plate 100 ul LB+Bacteria on to two Tet+Chl plates. Incubate one at 43° C. incubator, and incubate the other at 30° C. overnight.
3. A thick lawn of bacteria will grow on the plates incubated in 30° C. For the plates incubated in 43° C., only dozens of individual colonies will grow on top of a hazy background of very small satellite colonies. Pick 20 of these large colonies, inoculate each colony to 2 ml LB supplemented with tet (10 ug/ml) and chloramphenicol (12.5 ug/ml), and streak the same colony onto a tet+chl plates. Grow the miniculture with rigorous shaking at 43° C. overnight. Incubate the master plate at 43° C. incubator overnight and stored in 4° C. for further use.
4. Make miniprep DNA from a 1.5 ml miniculture using standard alkaline lysis methods. Dissolve the DNA in a 30 $\mu$l TE and use 5–10 $\mu$l of the DNA for restriction enzyme analysis.
5. Restriction digest with appropriate enzymes and analysis of the co-integrate by Southern blot. Due to the high efficiency of co-integrate formation even with 500 bp homology (>10%), I usually only analyze co-integration on one homology side (either A or B). For example, to analyze co-integrate on A side, use fragment A as a probe and digest the BAC DNA with an enzyme that will detect the co-integrate formation on A side (such as EcoRI). Standard southern blots are done to reveal the co-integrates. As controls, the original BAC and the shuttle vector should be included in this analysis. The reason to use the homology arms as Southern blot probes is that it will hybridize to two bands of appropriate size in the co-integrate BAC. As controls, the original BAC and the shuttle vector should be included in this analysis.

(V) Resolution and Southern Blot Analyses of Correctly Resolved BACs (6 Days):
1. Once the co-integrates are identified, a purified single colony of the co-integrate from the Tet+Chl plates grown at 43° C. is picked and streaked onto a Chlrorampenicol plate (12.5 ug/ml)) to grow single colonies.
2. Incubate the Chl plate at 43° C. overnight, to allow some bacteria to resolve and to lose the temperature sensitive pSV1 plasmid, and hence lose the tet resistance gene.
3. To select for tet sensitivity in the resolved BAC, 8 to 16 single colonies from the Chl plate are picked, and streaked onto Fusaric acid+Chloramphenicol plate (2 to 8 individual colonies can be streaked onto each plate). Two controls can be done to test the effectiveness of antibiotic selection of the FA+Chl plates: one is streaking a Tet-resistant colony (from the Tet+Chl plate), and the second is a tet-sensitive colony (from the plate growing the original BAC). Another control can be done is to streak the co-integrate colonies on just Chl plate (without fusaric acid).
4. Incubate the FA+Chl plates at 37° C. for 2–3 days. A long incubation time is necessary since the resolved colonies grow very slowly due to the presence of the fusaric acid. Tet containing colonies should not grow even in 48 hrs incubation. Therefore, there should be much fewer colonies on the Chl+Fusaric acid plates than on the Chl plates. These colonies are the resolved colonies.
5. A) Two alternative methods can be used to identify the correctly resolved BACs. If both A and B homology are about the same length, one can just pick 10–20 colonies, prepare miniprep DNA by alkaline lysis and do Southern blot to analyze the targeting events. About half of the resolved BACs should contain the correctly targeted marker genes. B) If the two homology arms are not the same length (>500 bp difference), one should use the colony hybridization to select the correctly resolved BACs. Pick 50–100 individual colonies from FA+Chl plates, streak them onto Chl plates and also onto the Tet+Chl plates, as a control for Fusaric acid selection. Each plate can accommodate 50 test colonies and two positive control colonies, which are the co-integrate colonies from the Chl plate. Grow the colonies overnight at 37° C. Abundant colonies should grow on the Chl plate, and none on the Tet+Chi plate, except the positive co-integrate controls. The selection for tet sensitivity at step 4 is very stringent and has essentially no background. Therefore, all the colonies that grow on FA+Chl plates have been found to contain resolved colonies. Colony hybridizations is performed, according to the standard protocols [Sambrook et al., (1989) supra], to select for the colonies that are resolved and resulted in targeted modification. The colony hybridization probe should be part of the recombination cassette excluding the arms, such as lacZ, Neo, GFP or polyA sequences.
6. Midi-prep DNA are prepared for the positive clones by the alkaline lysis method as described above. Restriction digests and Southern blots are performed to confirm targeting event on both homology side (A and B).
7. Pulse field gel analyses should be done to confirm the modification event and to determine if there are any rearrangements in the modified BACs. Since there are two Not I site flanking the BAC insert (Research Genetics), digestion with Not I should reveal the size of the modified BAC. Generally MluI, PacI and PmeI sites are included in the recombination cassette. Digestion with these enzymes will confirm the targeting events. Double digestion with these enzymes and with Not I will help to determine the integration site of the recombination cassette in the BAC. XhoI is usually used to fingerprint the modified BAC, since it has a wide distribution of fragment sizes. Comparing the Xho digestion pattern of the modified BAC with the original BAC will reveal any gross rearrangements in the modified BAC. Other enzymes, such as BamHI and AvrII can also be used for this purpose. Targeted BAC modification has been found not to introduce any unwanted rearrangements into the BACs. Probes used to hybridized to the PFGE blots include: insert specific probes (s.a. lacZ, PolyA, GFP and Neo) and whole BAC probe (to reveal all the digested bands from the BAC). Once the modified BACs are confirmed to have the specific targeted modification events and the lack of rearrangements, these BACs are ready to be used for the biological experiments, such as producing transgenic mice or transfecting cells.

4. Preparation of Large Quantity, High Quality Linearized BAC DNA for Pronuclear Injection (I) Maxiprep BAC DNA Preparation(1 day):
See the isolation and initial mapping of BACs section above.

(II) Prepare Intact Linearized BAC DNA for Pronuclear Injection (1 Day):
1. Digest 50 ug cesium banded BAC maxiprep DNA overnight in 500 ul total volume containing:

50 μg DNA

50 μl 10X NotI buffer or Buffer 3 (NEB)

50 μl 10XBSA 12.5 μl 100 mM Spermidine (final concentration 2.5 mM)

25 μl (250 units) Not I (NEB)

ddH2O to 500 ul total volume

Digestion is carried out at 37° C. for >10 hrs.

2. Preparation of the CL4b Column (performed at room temperature): Take a 5 ml plastic pipette, air-blow the cotton to the tip and clamp the pipette on a stand. Shake the CL4b sepharose (Phamacia) well, and gradually add the sepharose into the plastic pipette. Add until the packed sepharose to almost the top (with about 1 ml space to spare). Never let the column dry.

3. Once the column is ready, use a 10 ml syringe to set a reservoir on top of the column (buffer is added to the reservoir). Then equilibrate the column with 30 ml of the injection buffer (10 mM Tris.HCl,pH7.5, 0.1 mM EDTA and 100 MM NaCl). This takes about 2–3 hours.

4. Now add 5 ul 10X DNA dye into the 0.5 ml digested BAC DNA. Take the reservoir out and gently add the DNA(+ dye) onto the top of the column with a pasteur pipette. Wait until the DNA+dye just goes into the column, gently add 0.5 ml of injection buffer on top of the column.

5. Once the injection buffer almost goes in, the reservoir is put back with 10 ml of injection buffer in it. Now start collecting 0.5 ml fraction with a 24 well plate. Generally about 12 fractions are collected (or until the blue dye is almost at the bottom of the column).

6. Run 50 ul of each fraction on a pulse field gel to identify the appropriate fractions. The bands should be visible after ethidium bromide staining. A Southern blot is performed in order to choose the fractions with highest yield, and the least degradations.

7. Purified DNA is stored at 4° C. It is stable for weeks (e.g., no degradation was detected after 3 weeks).

Results

BACs are useful as tools for studying the regulation of gene expression in vivo. In one particular example, a BAC can include the murine brain specific zinc finger gene, RU49 [Yang et al., *Development* 122:555 (1996)]. RU49 has been shown by in situ hybridization to be expressed in the granule cell population of the murine cerebellum, the dentate gyrus and the olfactory bulb in the brain. However, proper expression of the lacZ marker gene could not be obtained in the cerebellum with a 10 kb RU 49 promoter-lacZ construct in transgenic mice, e.g., only one out of ten lines showed partial expression in the cerebellum. To overcome this problem, an homologous recombination based method for inserting an IRES-lacZ marker gene into the BAC containing RU49 was developed. The germline transmission in transgenic mice of an intact modified BAC and proper expression of the lacZ transgene in the cerebellum is demonstrated.

To modify BACs in *E coli*, a temperature sensitive shuttle vector based system for homologous recombination was employed [O'Connor et al., *Science* 244:1307–1312 (1989); Hamilton et al., *J. Bacteriol.* 171:4617 (1989)]. This temperature sensitive plasmid will replicate in cells growing at the permissive temperature (30° C.), but will be lost in cells growing at the restrictive temperature (42–44° C.) because its origin of replication can not function at the restrictive temperature [Hashimoto-Gotoh et al., *J. Bacteriol.* 131:405–412 (1977)]. To overcome the recombination deficiency of the BAC host i.e., a RecA⁻ host cell, the *E. coli* recA gene was introduced into the temperature sensitive shuttle vector. When transformed with the temperature sensitive shuttle vector (carrying a recombination cassette containing the recA gene) the host strain becomes conditionally competent to perform homologous recombination allowing in vivo modification of the resident BAC.

The general strategy for targeted BAC modification is shown in FIG. 1, which illustrates the steps involved in inserting a marker gene, e.g., IRES-lacZ-pGKpolyA (ILPA), into the BAC. First, two small genomic fragments, e.g., A and B, each containing greater than 500 basepairs of a gene of interest are cloned into the building vector (pBV1) in appropriate order and orientation to generate the recombination cassette. The recombination cassette is then transferred into the temperature sensitive shuttle vector (e.g., pSV1.RecA). The reason the recombination cassette is not built directly in the shuttle vector is due to the relative difficulty in manipulating its DNA, due to low copy number [Bochner et al., *J. Bacteriol.* 143:926 (1980); Maloy et al., *Bacteriol.* 145:1110 (1981)] and large vector size (11 kb).

This shuttle vector is then transformed into *E. coli* containing the BAC. The transformants can be selected by tetracycline resistance (carried by pSV1.RecA) and chloramphenicol resistance (carried by the BACs) at 30° C. Since the shuttle vector also carries the recA gene, homologous recombination can occur between the shuttle vector and the BAC, through either homology at A or B to form co-integrates. The co-integrates are selected by growth on tetracycline and chloramphenicol plates at 43° C. This temperature is non-permissive for shuttle vector replication, so that the non-integrated, free shuttle vectors are lost, resulting in the selection for bacteria carrying the integrated shuttle vectors, (either into the BACs or into the bacterial chromosomes). Correct BAC co-integrates can be identified by Southern blot analyses.

The co-integrates are then restreaked onto the chloramphenicol plates and grown at 43° C. overnight. A fraction of the co-integrates will undergo a second recombination event (resolution), through either homology at A or B. The resolved BACs will automatically lose the tet and the recA genes, since the excised shuttle vector plasmids cannot replicate at the non-permissive temperature. The resolved BACs can be selected by growing on chloramphenicol and fiusaric acid plates at 37° C., as growth on fusaric acid plates selects for the loss of tetracycline resistance, i.e., counterselecting against BACs that are resistant to tetracycline. As illustrated in FIG. 1, depending on which pair of homologous fragments undergo the second recombination event, the resolved BAC can be either the original BAC or the precisely modified BAC. The desired clones can be identified by colony hybridization using a labeled probe for the inserted marker. One important aspect of the method is that the recA gene is only temporally introduced into the bacterial host. Once the modification is finished, the bacteria will automatically lose the recA gene, returning to the recombination deficient state suitable for stable maintenance of the modified BACs.

Figure 2B:
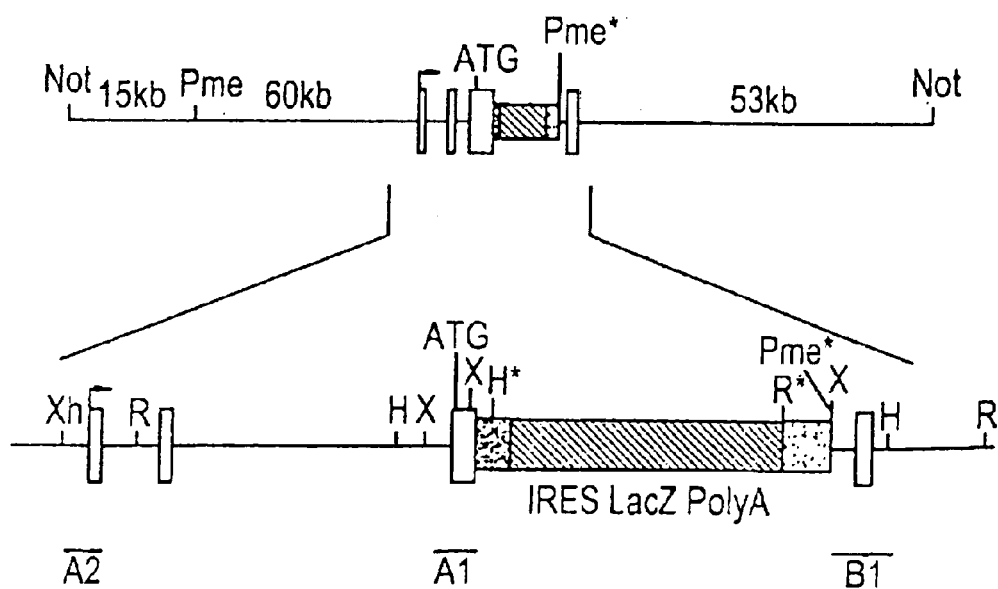
FIG. 2B depicts a map of the modified BAC169 with IRES LacZ PolyA insertion (BAC169. ILPA). An extra PmeI site is inserted with the marker gene (asterisk). The size of the two Pme-Not fragments and the PmeI fragment are indicated. Since the marker gene (4 kb) is less than the deleted genomic region (7 kb), the total size of the modified BAC (128 kb) is smaller than the original BAC (131 kb).
Figure 3C:
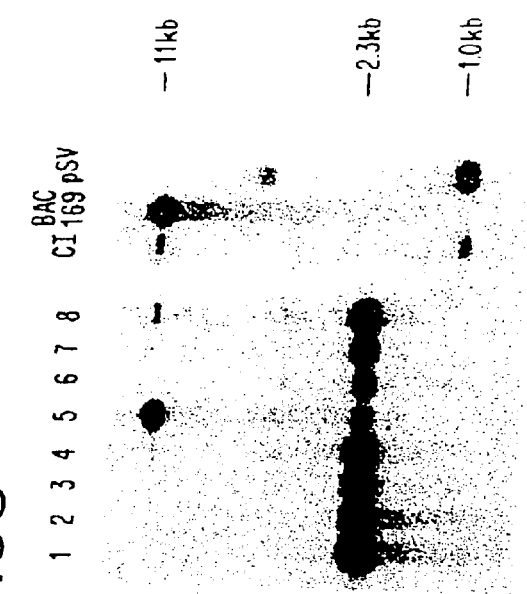
FIG. 3C shows the analyses of the 5' ends of the resolved BACs. Resolved BAC clones (1–8) were digested with HindIII and probed with homology A1. The controls are homology B1 co-integrates (CI), BAC 169 and the shuttle vector with recombination cassettes.
Figure 3D:
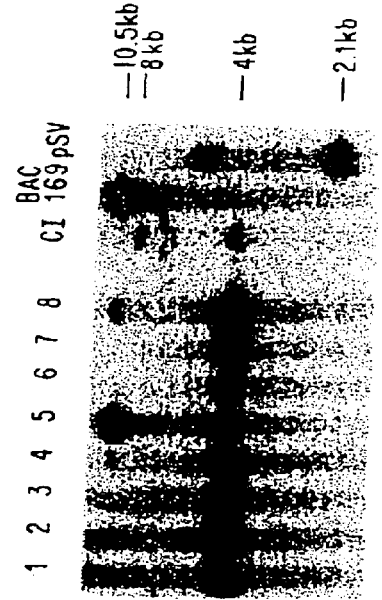
FIG. 3D shows the analyses of the 3' ends of the resolved BACs. The same procedure is used as described above except the resolved BAC clones were digested with EcoRI and probed with homology B1.
Figure 3A:
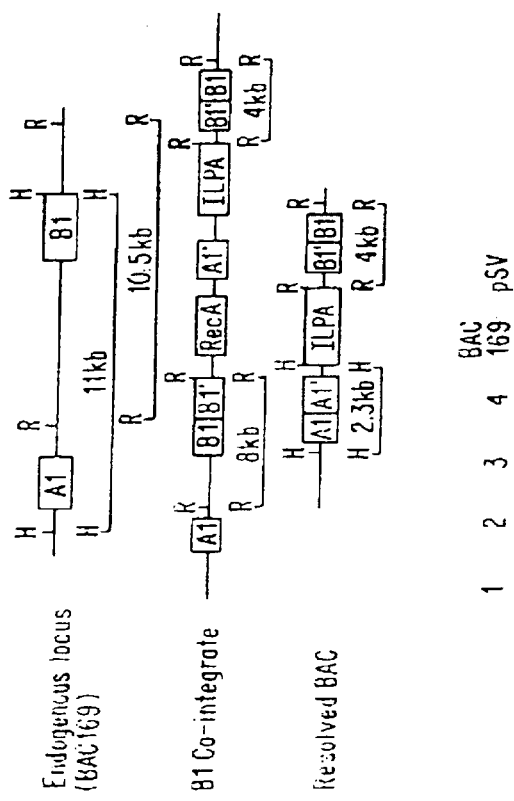
FIG. 3A shows a schematic representation of expected Southern blot fragments in BAC169, in co-integrates through homology B1, and in correctly resolved BACs. When analyzing recombination through homology B1, an EcoRI digest is used and homology B1 is used as the probe; when analyzing the recombination through homology A1, a HindIII digest is used and the homology A1 is used as probe.
Figure 3B:
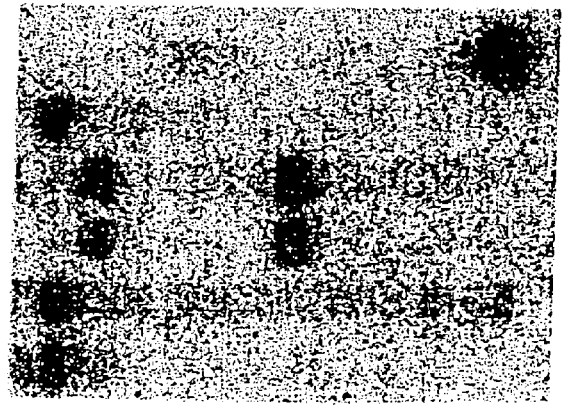
FIG. 3B shows homology B1 co-integrates. The EcoRI digest of BAC clones and controls are probed with homology B1. 1-4 represent four clones. BAC169 and pSV1 with the recombination cassette were used as controls.

This strategy termed targeted modification of BACs, was tested by introducing the IRES-lacZ-polyA (ILPA) marker into the 131 kb murine BAC169 containing the RU49 locus (FIG. 2A). In this case, the marker gene to the first coding exon of the RU49 gene was targeted with homology fragments being 1 kb and 1.6 kb respectively (FIG. 2B). Placing the IRES sequence before the lacZ gene ensures the translation of the marker gene even when lacZ gene is placed after the translation start site [Pelletier et al., *Nature* 334:320 (1988)]. The pSV1.RecA temperature sensitive shuttle vector containing the recombination cassette was transformed into the DH10 E. coli strain containing the BAC169 and selected by growth at either 30° C. or 43° C. on plates containing chloramphenicol and tetracycline. In contrast to growth at 30° C., which produced a thick lawn of transformed cells, growth at 43° C. resulted in growth of individual colonies. Twenty of these were picked and tested by Southern blots for co-integration of the shuttle plasmid into BAC169. As shown in FIG. 3B, analysis of twenty clones using the B1 fragment of the RU49 homology cassette resulted in the identification of two clones containing the appropriate 4 and 8 kb EcoRI bands (10%), indicating that these clones carry co-integrates that have occurred through this region of homology.

The co-integrates are then resolved as described above by growing the cells first on chloramphenicol plates at 43° C. and then on chloramphenicol and fusaric acid plates at 37° C. Fusaric acid provides a strong counterselection against bacteria containing the tetracycline resistance gene. Indeed, 200 colonies picked from these plates were all tet sensitive, indicating the stringency of the selection. Duplicated colonies growing on the chloramphenicol plates were used for colony hybridization with the pgkpolyA probe. Eight out of 200 colonies were positive (4%). Southern blot analyses using either homology at A1 or B 1 as the probe showed that all these clones contained correctly resolved BACs (FIGS. 3C and 3D). Three BACs (lanes 4,5 and 8) also contained wild type bands, which may represent either contamination from other clones, or a BAC containing two copies of co-integrates that resolved through two different homologous regions.

Figures 4A, 4B, 4C:
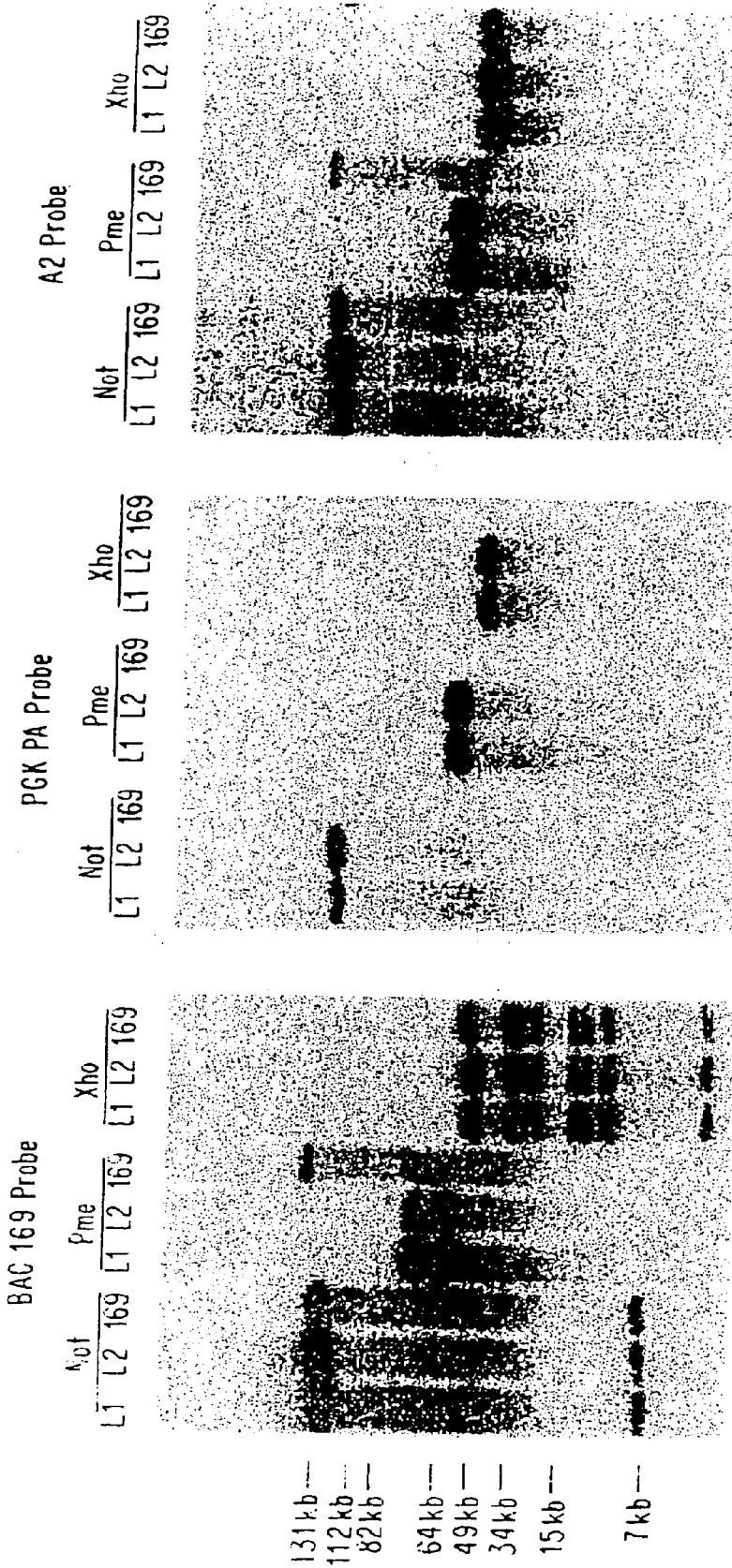
FIG. 4A shows the use of the BAC169 probe which revealed all the restriction fragments.
FIG. 4B shows the use of the pgkpoly A probe which only hybridized to the ILPA insert fragment.
FIG. 4C shows the use of the A2 probe which hybridized to a fragment outside the region of modification. The position of the markers are indicated.

The next step in our analysis was extensive mapping of the modified BACs to determine whether any unexpected deletions or insertions were generated during the modification procedure. FIG. 4 shows pulsed field gel mapping of the modified BAC L1 and L2 and the original BAC 169. The same filter was probed separately with the whole BAC169 probe, with a probe from the inserted marker gene (pgkpolyA) and a probe from the 5' non-modified region of the RU49 gene (A2). BAC169 probe (left panel) hybridizes with all the restriction fragments for each BAC. Thus, XhoI digestion reveals a finger print of the modified BACs showing that essentially all fragments are preserved. The only difference is that the fragment containing the ILPA insert is slightly smaller than the corresponding wild type fragment due to the replacement of the 7 kb RU49 fragment with the 4 kb marker gene (FIG. 2B). Digestion with NotI, which releases the entire BAC insert, also reveals a slightly smaller DNA insert in modified BACs for the same reason. Since the marker gene was engineered to carry an additional PmeI site (FIG. 2), digestion of the BAC L1 and L2 DNAs with this enzyme results in the generation of two fragments, in contrast to the single fragment seen in the original BAC169. The sizes of these fragments allow the determination that these BACs contain approximately 75 kb 5' to the PmeI site, and 53 kb 3' to it (FIG. 2). No apparent rearrangements have occurred during the modification procedure.

To confirm this conclusion, the modified BACs and BAC169 were probed with both a marker specific probe (pgkpolyA) and a probe near the promoter region and outside the modification region (A2). Consistently, both modified BACs contained a single band homologous to the marker gene probe which is not present in BAC169. When the A2 probe was used, a single band of expected size appeared in all three BACs. Additional fingerprinting of all eight modified BACs with HindIII, EcoRI and AvrII digests showed that no detectable rearrangements or deletion existed in these BACs. Thus, the temporary introduction of the recA gene into the BAC host strain does not introduce any rearrangements or deletions.

To test the reproducibility and reliability of the targeted BAC modification, the BAC L1 was further modified by replacing the IRES-lacZ sequence with pgk-neo sequence. In this case, homologous fragments of about 500 bp each were used. The modified BACs were also efficiently obtained and shown not to have any rearrangements or deletions. Therefore, targeted BAC modification is a simple method to precisely modify BACs without introducing any unwanted changes in the BACs.

Figure 5A:
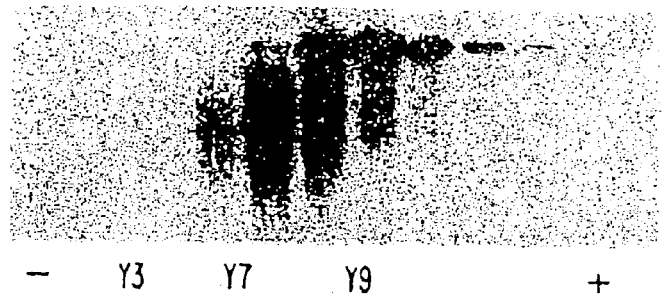
FIG. 5A depicts purified linearized BAC L1 128 kb Not I insert for pronuclear injection. The pulsed field gel is probed with pgkpolyA probe. The numbers represent different fractions. The smear below the intact fragment represent degradation and undigested DNA.
Figure 5B:
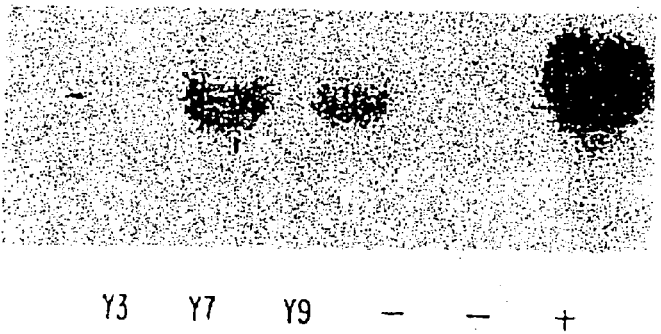
FIG. 5B shows Southern blot analyses of the founder transgenic mice with the lacZ probe. The tail DNA were digested with Bam HI and Southern blot analysis was performed. The negative control consisted of littermates of Y3, Y7 and Y9 mice. The positive control was a conventional transgenic mouse with the lacZ transgene.

To demonstrate the possibility of using the modified BACs for in vivo studies for gene expression and gene function, transgenic mice carrying the modified BAC169 with the IRES-LacZ insertion were generated. To purify the 128 kb BAC insert for pronuclear injection, several established methods for purifying large YAC DNA were attempted, and resulted in considerable amount of DNA fragmentation. In contrast, when a simple gel filtration column filled with SEPHAROSE CL-4B was tried, very pure fractions of intact linear BAC DNA insert were obtained in an appropriate injection buffer, e.g., 100 mM NaCl, 10 mM Tris.HCl, pH 7.5 and 0.1 1 mM EDTA (FIG. 5A). Unlike YAC DNA purification which typically results in a low DNA yield, the purified fractions using the SEPHAROSE CL-4B column contained a large quantity of high concentration linear DNA (e.g., 0.5 mls of 3 µg/ml DNA or more). The purified DNA could be directly visualized with ultraviolet light after ethidium bromide staining. The SEPHAROSE CL-4B column could also efficiently separate the degraded DNA (in this case in fractions 3–6) from the pure linear DNA (fractions 7–9) (FIG. 5A). Fraction 8 contained 3 µg/ml DNA and was used directly for pronuclear injection. Pronuclear injection into the fertilized C57BL/6 mouse zygote is performed according to a standard protocol [Hogan et al., in Manipulating the Mouse Embryo (Cold Spring Harbor Laboratory Press, New York, 1986)]. Two different concentrations of fraction 8 BAC DNA (obtained as described above) were used: 3 µg/ml and 0.6 µg/ml. No newborns were obtained with the high concentration DNA, suggesting that the high concentrations may be toxic to the zygote. However, with the lower concentration of pure linear DNA, 15 newborn mice were obtained and two of them (13%), Y7 and Y9, contained the lacZ marker gene as demonstrated on a Southern blot (FIG. 5B). The intensity of the bands allows an estimate of 2–3 transgene copies for Y7 and one copy for Y9.

Figure 5C:
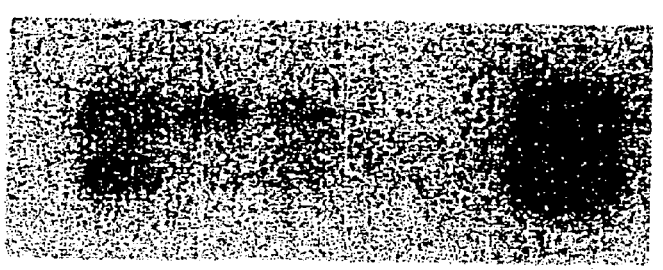
FIGS. 5C and 5D show the results of using PCR to determine the presence of BAC ends in the transgenic mice. The DNA at each end corresponding to the vector sequence is amplified and probed with a third oligonucleotide in the middle of the fragment. The appropriate size fragment is indicated. The negative controls are littermates. The positive control was BAC169 DNA.
Figure 5D:

To determine if the intact BACs have been integrated into the genome, the presence of both ends of the BAC ends was assayed for in the transgenic mice. Since both BAC ends contain some vector sequence, PCR primers specific to the vector sequence were generated and used to amplify the transgenic DNA. The amplified products were then probed with a third labeled oligonucleotide probe within the amplified region. As shown in FIG. 5C and FIG. 5D: Y3, Y7 and Y9 have both ends present, while the negative controls do not. Since Y7 and Y9 also have the lacZ gene, they are likely to contain intact BAC transgenes. For Y3, whereas it has both ends it does not contain the lacZ gene. This may be due to either a rearrangement or fragmentation during the injection prior to integration.

Figure 5E:
FIG. 5E shows the germline transmission of the lacZ transgene in the Y7 mouse line. Tail DNA from two litters having eight mice each were prepared and digested with BamHI. Southern blot analysis was performed with the lacZ probe.

The Y7 transgenic mice also gave rise to germline transmission after breeding with B6/CBA mice. In two litters having a total of eight pups, three pups carried the LacZ transgene (FIG. 5E). Further analysis demonstrated that the transgene was transmitted in a Mendelian distribution to more than fifty Y7 offspring.

Figure 6B:
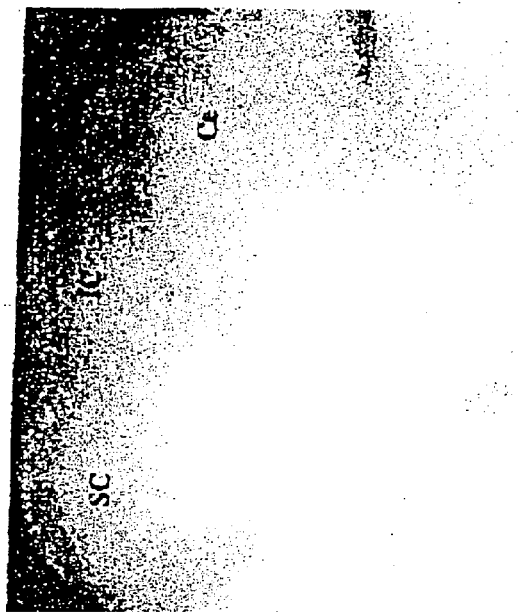
FIG. 6 shows the expression of the lacZ transgene in the brain of the Y7 BAC transgenic line. P6 mice brain from Y7 transgenic mice (FIG. 6A) and a wild type control litter mate (FIG. 6B) were whole mount stained to reveal lacZ expression in the Y7 cerebellum. Thick saggital sections (5 mm) from Y7 transgenic mice were also stained for lacZ expression.
FIG. 6C shows the low magnification and FIG. 6D shows the high magnification of the rectangle area indicated in FIG. 6C. Expression in the cerebellum, the detate gyrus and the lineage of the olfactory bulb are indicated (i.e. SVZ, RMS and the OB). Abbreviation Ce, cerebellum; SC, superior collicoli; IC, inferior colliculi; DG, dentate gyrus; VZ, ventricular zone; SVZ, subventricular zone; LV, lateral ventricle; RMS, rostral migratory tract; OB, olfactory bulb; Co, cortex.
Figure 6D:
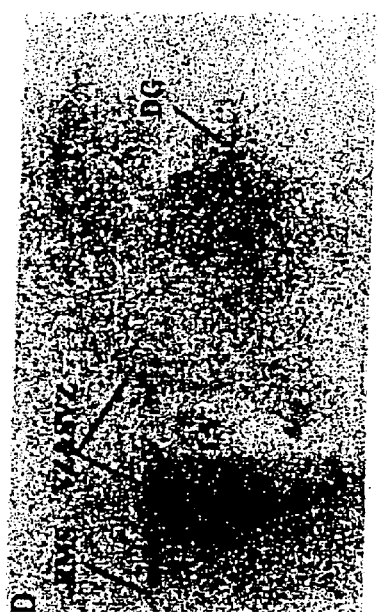
Figure 6A:
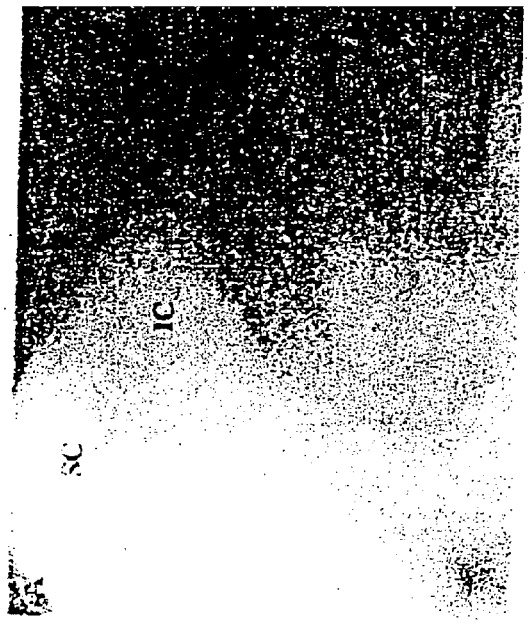
Figure 6C:
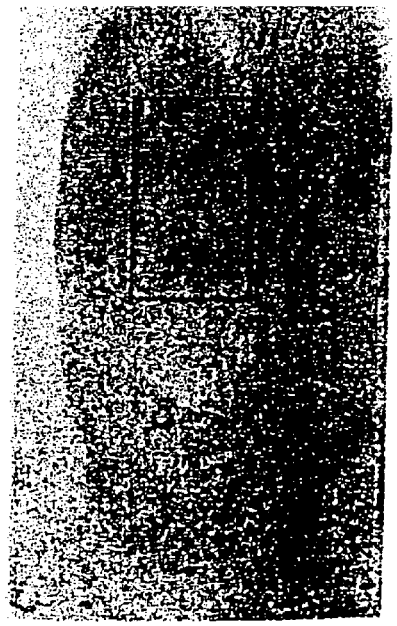

Next the expression of lacZ gene in the cerebellum of the Y7 transgenic mice was determined by whole mount lacZ staining. RU49 is normally expressed in the granule cells of the cerebellum, the dentate gyrus and the olfactory bulb (including the subventricular zone, the rostral migratory stream, and the olfactory bulb proper) [Yang et al., *Development*, 122:555–566 (1996)]. In previous studies, RU49 promoter lacZ transgenic mice with 10 kb promoter had been generated. However, all of the transgenic lines showed strong positional effects: either they did not express in the brain at all, or they were ectopically expressed in the cortex, but not the cerebellum. One particular 10 kb-lacZ transgenic line did show restricted expression in the cerebellum, however, the expression was restricted to the caudal half of the cerebellum. With 128 kb of RU49 endogenous sequence surrounding the lacZ gene in the Y7 line, at postnatal day 6, the transgenic mice showed a lacZ expression pattern closely resembling the endogenous expression pattern FIG. 6). In the cerebellum, the marker gene is expressed throughout the cerebellum (FIG. 6A) and no expression is seen in five control littermates (FIG. 6B). Further analysis showed that the transgene is expressed at high level in the EGL and lower level in the IGL. The lacZ marker gene is also expressed in the dentate gyrus and the rostral migratory stream and the olfactory bulb (FIGS. 6C and 6D). The pattern of the BAC transgene expression closely resembles the endogenous RU49 expression pattern in the brain. It is evident that the large genomic DNA in the BAC transgene can overcome the positional effects and confer the proper expression of RU49 in vivo, in contrast to our results using conventional transgenic constructs.

As taught herein, bacterial based artificial chromosomes (BACs and PACs) are ideal for constructing large DNA for gene targeting. As demonstrated herein with the targeted BAC modification method, BACs and PACs can be readily modified to introduce selection genes, marker genes, and deletions. Making a BBPAC gene targeting construct will take about the same time as making a conventional targeting construct (1–3 months). Moreover, BBPAC targeting construct DNA can be easily isolated in milligram quantity and high quality. This is advantageous over the YAC system, since it is difficult to purify large quantities of high quality YAC DNA.

EXAMPLE 2

BAC Mediated Gene Dosage Analysis: A Role for ZIPRO1 (RU49/Zfp38) in Progenitor Cell Proliferation in Cerebellum and Skin Introduction Analysis of loss-of-function phenotypes has played a central role in the discovery of complex morphogenetic pathways in a variety of organisms. For example, the seminal loss-of-function screens for genes affecting cell cycle traverse in yeast [Hartwell et al., *Science* 183(120):46–51 (1974)] and for mutations affecting early *D. melanogaster* development [Nusslein-Volhard and Wieschaus, *Nature* 287:795–801 (1980)] have provided the basis for our current understanding of cell division and of embryonic patterning. However, in both cases, it was readily appreciated that loss-of-function genetics would not yield all the genes in the pathway under study, and alternative strategies for genetic analysis were therefore devised. Thus, high copy number suppression screens have been highly successful in identifying additional genes important for cell division in yeast [Levine, et al., *Prog. Cell Cycle Res.* 1:101–114 (1995)], and over- or misexpression studies [P. A. Rørth, *Proc. Natl. Acad. Sci.* 93:12418–12422 (1996); Perrimon, *Proc. Natl. Acad. Sci.* 95:9716–9717 (1998); P. A. Rørth, Development 125:1049–1057 (1998)] are currently being used to uncover functions for the approximately two-thirds of fly genes that have no readily observable loss-of-function phenotype [Miklos and Rubin, *Cell* 86:521–529(1996)].

Expression of the gene encoding the zinc finger DNA binding protein Zipro (now also known as Ru49 and Zpf38, though throughout this Application it will be referred to as RU49) is restricted to granule neurons in the developing and adult mouse brain [Yang et al., *Development* 122:555–566 (1996)]. Cerebellar granule cells are the most numerous neuronal population in the mammalian CNS, accounting for about 80% of the total neurons in the human brain [Williams and Herrup, *Ann. Rev. Neurosci* 11:423–453 (1988)]. Granule cell precursors are specified during embryogenesis [Alder et al., *Neuron* 17:389–399 (1996)], forming a secondary proliferative zone called the external granular layer (EGL) [Miale and Sidman, *Exp. Neurol.* 4:277–296 (1961); Fujita et al., *J. Comp. Neurol.* 128:191–208 (1996)]. Most mature granule cells arise in a period of rapid cell division that extends from birth until the acquisition of full motor function [Fujita et al., *J. Comp. Neurol.* 128:191–208 (1996); Altman, *J. Comp. Neurol.* 136:269–294 (1969)]. Loss-of-function genetic study showed that the murine helix-loop-helix transcription factor, Math1, is essential for the establishment of the cerebellar granule cell lineage during the embryonic development [Ben-Arie et al., *Nature* 390:169–172 (1997)].

Recent studies also demonstrated the participation of the Sonic hedgehog (Shh) pathway in the postnatal granule cell proliferation in vivo [Vorechovsky et al., *Oncogene* 15:361–366 (1997); Goodrich et al., *Science* 277:1109–1113 (1997); Wechsler-Reya and Scott, *Neuron* 22:103–114 (1999)], supporting a model for local control of granule cell proliferation in response to Purkinje cell production of this mitogen [Wechsler-Reya and Scott, *Neuron* 22:103–114 (1999)]. However, the molecular mechanisms downstream of the Shh signal transduction remain unknown.

Methods

Generation of Ru49 loss-of-function mice. The Ru49 genomic locus was mapped using four lambda phage clones and four BAC clones derived from 129 SvE strain of mice. The Targeting vector contained a 3.7 kb 5' arm and a 6 kb 3' arm in a pKSNT vector [Tybulewicz et al., *Cell* 65:1153–1163 (1991)]. ES cell selections were performed at The Rockefeller University Gene Targeting Facility. Initial typing was done by Southern blot using a 500 bp pair probe from the 5' region (FIG. 13a) yielding a 15 kb wildtype allele and 11.5 targeted allele upon digestion with BamHI. Subsequent typing was done using PCR primers internal to the neo gene and a second pair within the disrupted region (5' primer: 5'AAAGTCCTGCTGGCTCGGGAATC-3' (SEQ ID NO: 1) and 3'primer: 5'-GCCTCCTCTGCATTTCAGGG-3') (SEQ ID NO:2).

Generation of the transgenic mice. The FLAG and His tags and the IRES.EGFP1 marker gene (internal ribosome entry site followed by a nucleic acid encoding an enhanced green fluorescent protein) were inserted into the BAC169F 1 (Research Genetics) and generated the transgenic mice as described [Yang et al., Nat. Biotech. 15:859–865 (1997), Example 1 above]. The transgenic founders were in C57BL6/CBA F1 background and were backcrossed to C57BL6 in successive generations. F1, F2 and F3 offsprings from this backcross were used for analyses.

Northern blot, Southern blot analyses and fine restriction mapping of the modified BACs. Total RNA was prepared from postnatal day 10 D1 and E6 cerebella using the RNeasy Midi columns (Qiagen). Northern blots were performed with a Ru49 cDNA probe and with an IRES.EGFP1 probe. The intensity of each band was measured using a Phosphoimager. Southern blot analysis was performed as described [Yang et al., Nat. Biotech. 15:859–865 (1997), Example 1 above]. For fine restriction mapping of the modified BACs, DNA from wildtype BAC 169, BAC169.tIRES.EGFP and BAC169.ILPA were digested with EcoRI and HindIII and separated on 1% agarose gel. A Southern blot was prepared from the gel and was probed separately with the 1.6 kb XbaI-HindIII genomic DNA probe and the entire 131 kb BAC 169 probe.

Measurement of IGL area and granule cell density. P20 to P22 cerebella were taken and mounted in TISSUETEK mounting media for frozen sections, the IGL area was measured from a digitized image of a cresyl violet stained 10 $\mu$m sections and the MacMeasure (NIH image) image analysis program. To minimize the variations due to weight differences, mice were weight-matched to be within 0.5 grams of the average weight. The granule cell density was counted using a grid measuring 900 $\mu m^2$ that was randomly placed in the middle region of lobule V. For each cerebellum, six sections were counted and the average density was calculated. The statistical significance was calculated using a t-test.

Immunohistological Staining for phosphorylated H3. Staining was performed on mid-sagittal sections from paraffin embedded P9 cerebella. The sections were rehydrated and stained with a polyclonal antibody to phosphorylated histone H3 (Upstate Biotechnologies) and revealed using a vectastain ABC kit (Vector laboratories), DAB (Sigma) and counterstained with cresyl violet. The total number of labeled cells in the EGL was counted.

Granule cell proliferation assay. P8 cerebellar granule cells from the E6 line were prepared and cultured as re-aggregates as described [Gao et al., Neuron 6:705–714 (1991)]. At least six wells of 500,000 cells per well per genotype were used in each assay. In each well, 1.5 $\mu$Ci $^3$H-thymidine (NEN) was added and the cells were incubated at 37° C. for 22 hrs. The cells were washed in CMF-PBS, lysed by adding 4×volume of $H_2O$ and the DNA were precipitated using 10% TCA. Incorporation of $^3$H-thymidine was determined by scintillation counting of the precipitated material.

In situ detection of granule cell death. Sagittal sections (12 $\mu$m) were prepared from P8 cerebella of the E6 line. The broken DNA ends in the dying cells were labeled using the In situ cell death detection kit (POD) (Boehringer-Mannheim).

Analysis of cerebellar foliation pattern. Cerebella from weight-matched P20–P22 D1, E6 and Y7 mice were dissected out, lightly stained with cresyl violet and directly inspected for foliation pattern under a dissection microscope.

Analysis of the skin phenotype. Animals were sacrificed and skin from the back near the midline was taken and fixed overnight in 75% Ethanol and 25% Acetic Acid. The tissue was dehydrated and embedded in paraffin. Tangential 10 $\mu$m sections were taken for cresyl violet and anti-phospho H3 immunohistological staining.

Results

A genetic analysis of Ru49 in vivo by gene targeting [M. R. Capecchi, Science 244:1288–1292 (1989)) and bacterial artificial chromosome (BAC) mediated transgenesis [Example 1 above, Yang et al., Nat. Biotech. 15:859–865 (1997)] is presented below. While no obvious phenotype was observed in Ru49 null mutant mice, increased Ru49 expression in vivo results in an increase in granule cell proliferative capacity and an increase in granule cell number. The formation of intralobular fissures is elevated in the Ru49 BAC transgenic mice, revealing an important role for this factor in cerebellar morphogenesis. In addition, in a subset of transgenic mice in three independent transgenic lines, increased Ru49 gene dosage also resulted in hair loss secondary to overproliferation of precursors in the skin and abnormal follicular development. These results demonstrate a role for Ru49 in the proliferation of granule cell precursors during postnatal development, and document the important contribution of postnatal granule cell proliferation to the final stages of cerebellar morphogenesis. Furthermore, they reveal the expression of Ru49 in the skin and demonstrate a role for Ru49 in proliferation of progenitor cells and tissue histogenesis at that site. These results further illustrate the utility of BAC mediated gene dosage experiments for investigation of redundant genetic functions in the mouse.

Figure 13:
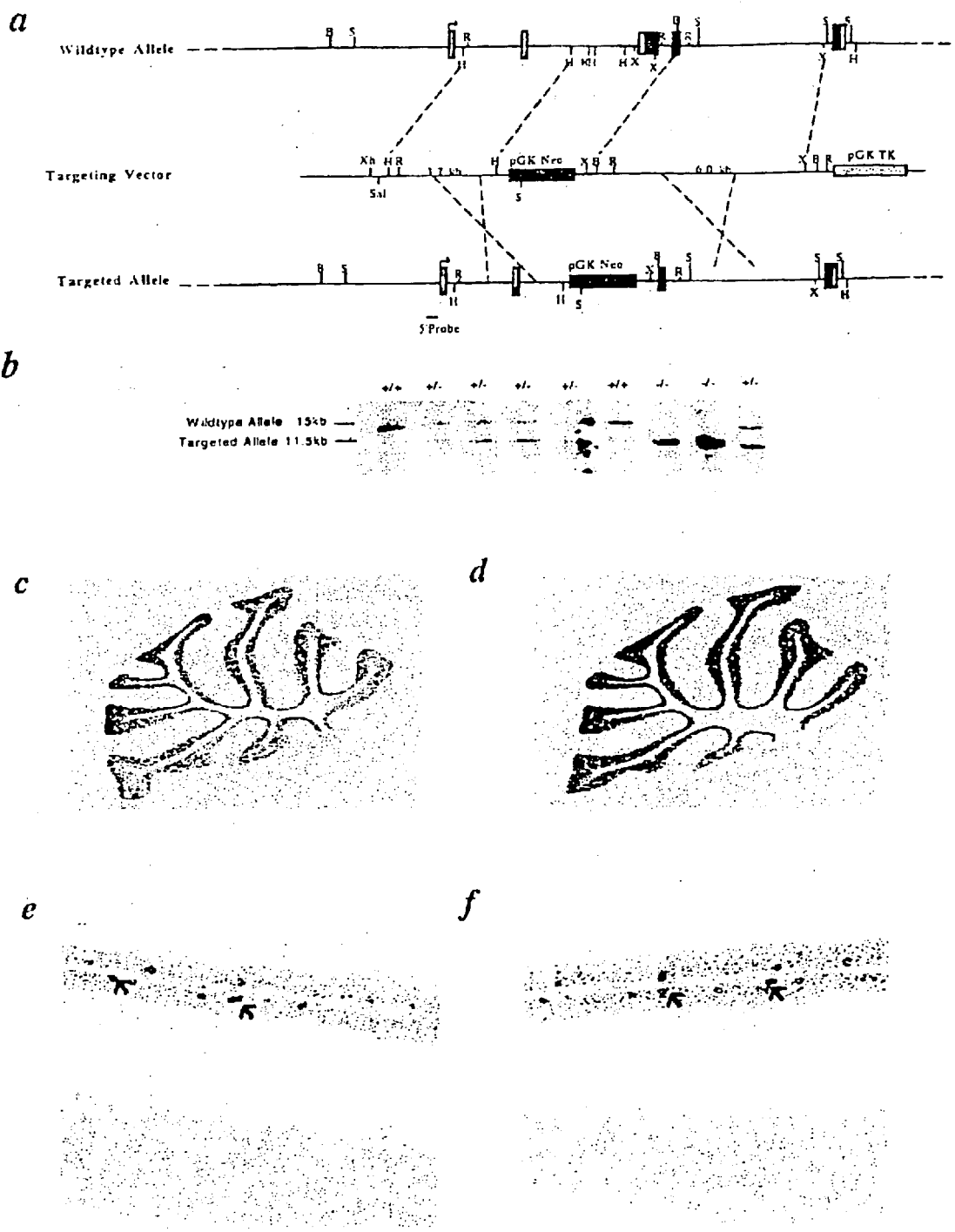
FIGS. 13a–13f show the targeted disruption of Ru49 gene.

Ru49 loss-of-function genetic analysis: To test the role of Ru49 in vivo, mice were prepared with a targeted loss-of-function mutation at the Ru49 locus. As shown in FIG. 13a, the gene targeting vector employed for this work resulted in replacement of the entire first coding exon and half of the second exon of the Ru49 gene with the neo gene [Southern and Berg, J. Mol. Appl. Genet 4:327–341 (1982)]. This results in deletion of both the Ru49 activation domain [Chowdhury et al., Mech. Dev. 39:129–141 (1992)] and the LeR or SCAN box domains [Pengue et al., Nucleic Acids Res. 22:2908–2914 (1994); Williams et al., J. Biol. Chem. 2709:22143–22152 (1995)]. Since no in frame methionine residue is found in the remaining Ru49 coding exons until well into the fourth zinc finger motif, the zinc finger DNA binding domain [Klug and Rhodes, Cold Spring Harb. Symp. Quant. Biol. 52:473–482 (1987)] is also severely truncated, leading us to conclude that this targeting event produces a null mutation.

Ru49$^{-/-}$ mice are born in a Mendelian ratio, they are fertile and display no apparent morphological or behavioral abnormalities. To assess the effect of the loss of Ru49 activity in the cerebellum, both the size and morphology of the cerebella of Ru49$^{-/-}$ mice were measured relative to their Ru49$^{+/-}$ and wild type littermates (FIG. 13b). No statistically significant difference in the size or morphology of the cerebellum was evident in these animals (FIGS. 13c and 13d). Since the final number of neurons in the developing brain reflects both the proliferation of the precursor cells and programmed cell death in the postmitotic cells [Cowan et al., Science 225:1258–1265 (1984)], a failure to observe changes in granule cell number in the adult could result from compensatory changes in cell death that might mask possible differences in granule cell proliferation. To address this possibility, the number of mitotic cells in the external germinal layer (EGL) of P9 cerebella were directly measured using an antibody to phosphorylated histone H3 [Juan et al., Cytometry 32:71–77 (1998)] (FIGS. 13e and 13f). In five Ru49$^{-/-}$ mice, the average number of mitotic cells in midline sagittal cerebellar sections is 261+/−34, while in five wildtype littermates, the number is 252+/−61. Thus, no significant difference in the number of EGL mitotic cells was observed (P=0.9) between the two groups. It is therefore reasonable to conclude that this type of genetic manipulation does not result in an obvious and informative phenotype for the Ru49 gene.

Figure 14:
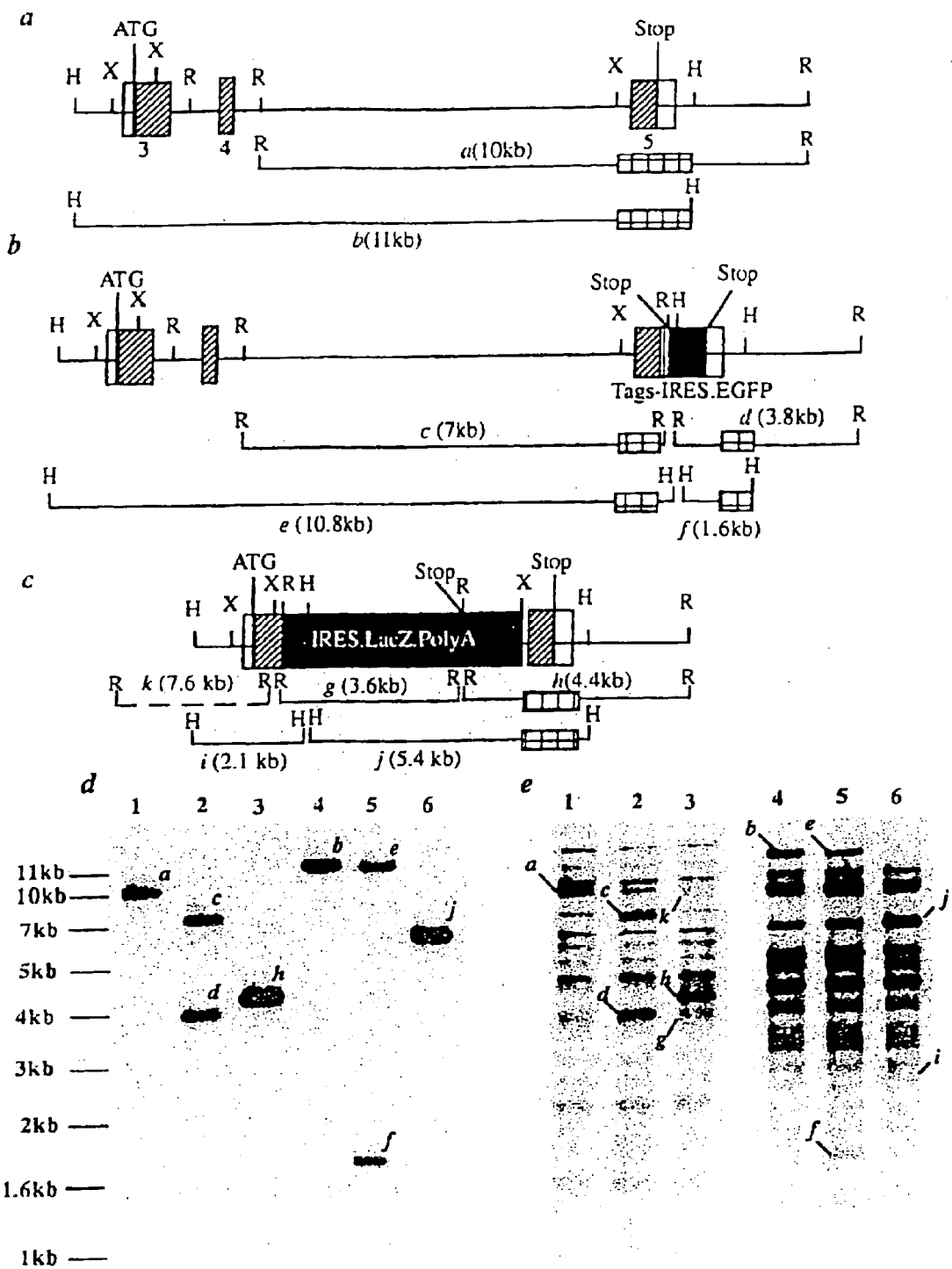
FIG. 14 contains a schematic drawing of the relevant regions of the BAC169, BAC169.tEGFP and BAC169.ILPA. and fine restriction mapping of these BACs. A part of BAC169 containing the Ru49 exon 3-5 are shown (FIG. 14a). The corresponding region containing the modification made in BAC169.tEGFP (FIG. 14b) and BAC169.ILPA (FIG. 14c) are also shown. The open box represents the untranslated region of an exon. The closed box represents the coding region of the exons. The location of restriction sites for HindIII (H) and EcoRI (R) are indicated. For each BAC construct, the size of the EcoRI fragment(s) and HindIII fragment(s) containing the 1.6 kb Xba-Hind fragment are also shown. Each fragment is labeled with italicized alphabet from α to k and each corresponds to a labeled fragment shown in the Southern blot below (FIGS. 14d and e).

Preparation of modified Ru49 BACs for genetic analysis: Since functional redundancy might account for the absence of an evident loss-of-function phenotype for many mammalian genes, the strategy of increasing Ru49 gene dosage to gain insight into its role in vivo was pursued. Previously, it was reported that a 131 kb bacterial artificial chromosome (BAC) covering the Ru49 locus in which a lacZ marker gene was inserted in place of Ru49 coding exons exhibited proper expression (BAC169.ILPA, FIG. 14c) [Yang et al., Nat. Biotech. 15:859–865 (1997), Example 1 above]. The same approach was therefore employed to increase Ru49 gene dosage in vivo. To perform this experiment, a modified BAC construct (BAC169tEGFP) was constructed that fused the Ru49 C-terminus with two in frame epitope tags and appended an IRES/EGFP marker gene (FIGS. 14a and 14b). Due to the presence of the internal ribosome entry site (IRES) sequence [Pelletier and Sonnenberg, Nature 334:320–325 (1998)], the fusion transcript translates two proteins, epitope-tagged Ru49 and EGFP 1. To control for the possible presence of other dosage sensitive genes carried on the BAC that might contribute to any phenotypic change, the previously described Y7 BAC169.ILPA transgenic line was used [Yang et al., Nat. Biotech. 15:859–865 (1997), Example 1 above]. The BAC169.ILPA BAC contains identical sequences outside of the Ru49 gene, but does not express the Ru49 protein (FIG. 14c). To assess whether the BACs are correctly modified, detailed restriction mapping of the original BAC 169 and the two derivatives, BAC169.ILPA and BAC169tEGFP, were performed using restriction digests with NotI, PmeI, XbaI, XhoI, EcoRI and HindIII. As shown for the EcoRI and HindIII digests in FIG. 14d, Southern blots using the 1.6 kb Xba-HindIII probe from the Ru49 locus reveal the correct targeted DNA fragments for both BAC169.tEGFP and BAC169.ILPA. When the same blot was probed with the entire BAC169 to reveal all restriction fragments, it was apparent that all visible differences between BAC 169tEGFP, BAC169.ILPA and the wildtype BAC169 can be accounted for by expected changes within the targeted regions (FIG. 14e). These results demonstrate that the modification of these BACs by homologous recombination in E. coli [Yang et al., Nat. Biotech. 15:859–865 (1997), Example 1 above] yielded only the intended insertions and replacements, and that no unplanned rearrangements occurred during the procedure.

Figure 15:
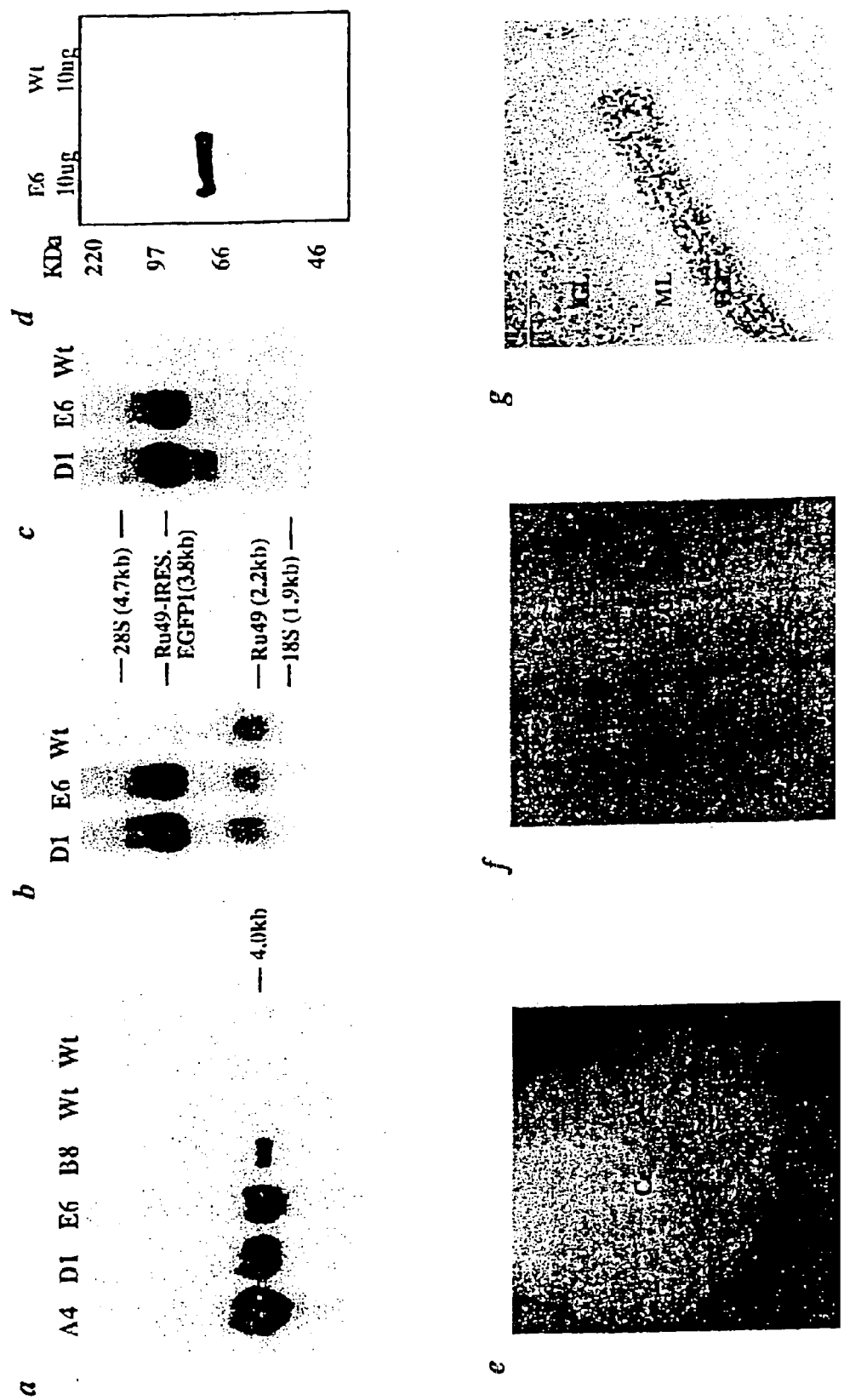
FIGS. 15a–15g show the generation of BAC169tRGFP transgenic mice.

A role for Ru49 in granule cell proliferation revealed by increased gene dosage using BAC transgenic analysis. Four transgenic mouse lines carrying BAC169tEGFP were produced (FIG. 15). Copy number analysis shows that the A4 line contains fourteen copies, the D1 and the E6 line six copies each, and the B8 line one copy. Lines D1 and E6 were chosen for further analysis because the BAC transgene copy number in these strains was comparable to that in the control Y7 line (four copies). Northern blot analysis showed that the D1 and E6 transgenic cerebella expressed a 3.8 kb fusion mRNA containing both the Ru49 and the IRES.EGFP1 sequences, in addition to the wildtype 2.2 kb Ru49 mRNA (FIGS. 15b and 15c). Quantitative analysis of these results established that the D1 line expresses approximately 4 fold and the E6 line 5 times the wildtype level of Ru49 transcript. As shown in the BAC 169.ILPA line (FIG. 15g), the BAC169tEGFP lines expressed the EGFP marker proteins at a higher level in the EGL than in the IGL of the developing cerebellum (FIGS. 15e and 15f), as expected from the pattern of expression of the endogenous Ru49 gene [Yang et al., Development 122:555–566 (1996)]. The transgenic animals also produce epitope tagged Ru49 protein of the expected size in the cerebellum (FIG. 15d). Correct expression was also seen in the dentate gyrus, olfactory bulb, thymus, testis and skin; no ectopic expression was observed.

Figure 16:
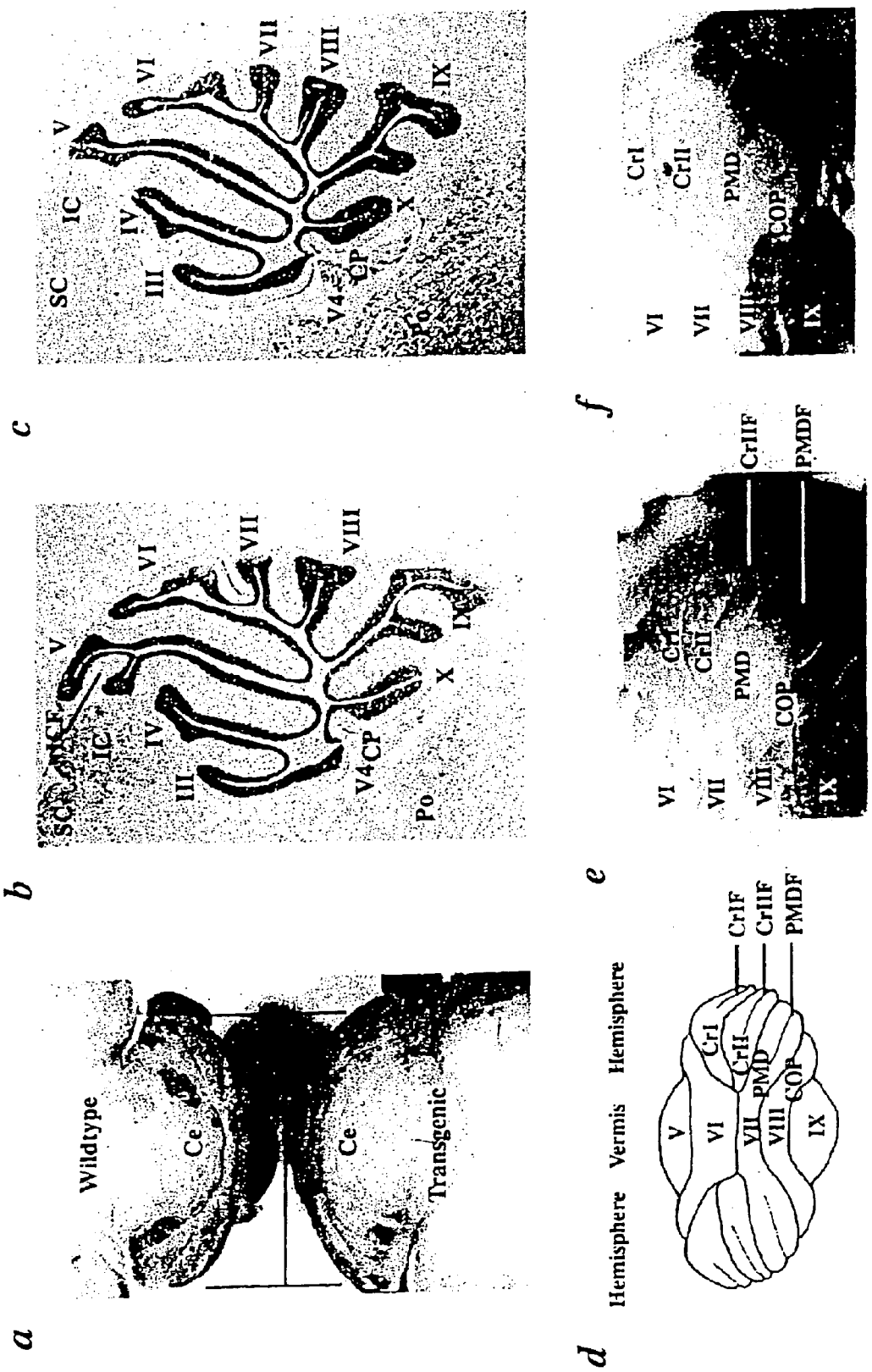
FIGS. 16a–16f show the morphological alterations in the BAC169tEGFP transgenic cerebella.

The D1, E6 and Y7 transgenic mice are fertile, of normal weight and longevity, and have no apparent motor or behavioral abnormalities. However, the cerebellum of P10 to P20 transgenic mice are consistently larger than those of their wildtype littermates, as shown in whole mount (FIG. 16a) or in midsagittal section of the cerebellar vermus (FIGS. 16b and 16c). Since Ru49 overexpression is restricted to the granule cell lineage, the granule cell number was estimated by measuring the IGL area and granule cell density in vermal sagittal sections from the D1 and E6 cerebella. As shown in Table 1, there is a significant increase in the total vermal IGL area in the D1 (17%) and E6 cerebella (16%), and in the IGL area of individual cerebellar folia compared to their wildtype littermates. In contrast, the Y7 transgenic cerebella, which do not overproduce Ru49, show no increase in IGL area when compared to their wildtype littermates (Table 1). No significant difference is observed in granule cell density in the D1, E6 and Y7 transgenic mice compared to their wildtype littermates. It can be concluded that increased Ru49 gene dosage in vivo leads to an elevation in the number of granule cells in all regions of the cerebellar cortex. Furthermore, there is no significant difference in cerebellar size in these transgenic lines at P0, indicating that Ru49 gene dosage influences the granule cell acquisition postnatally.

TABLE 1

Comparison of the cerebellar granule cell densities and the IGL area in P20–P22 BAC169tEGFP and BAC169.ILPA cerebella. The number of animals used for each measurement is shown in parenthesis. Each data point is shown as Mean +/− SEM. Statistical significance was measured using a t-test.

| | BAC169tEGFP (Ru49 Overexpression Transgenic Lines) | | | | BAC169.ILPA (Control Transgenic Line) | |
|---|---|---|---|---|---|---|
| | D1 Tg | D1 Wt | E6 Tg | E6 Wt | Yt Tg | Y7 Wt |
| Granule Cell | | | | | | |
| Density (GC# per 900 μm2) | 37.2 ± 1.68 (n = 3) | 37.3 ± 1.66 (n = 3) | 36.5 ± 1.74 (n = 3) | 37.2 ± 1.63 (n = 3) | 39.6 ± 1.46 (n = 3) | 39.0 ± 1.73 (n = 3) |
| IGL Area (mm2) | | | | | | |
| Total | 5.94 ± 0.12 (n = 8) *p = 0.005 | 5.06 ± 0.18 (n = 8) | 4.68 ± 0.19 (n = 9) *p = 0.02 | 4.04 ± 0.19 (n = 9) | 5.92 ± 0.42 (n = 5) | 5.85 ± 0.29 (n = 5) |
| Lobule II | 0.66 ± 0.04 *p = 0.05 | 0.56 ± 0.005 | 0.52 ± 0.03 *p = 0.01 | 0.41 ± 0.02 | 0.67 ± 0.08 | 0.73 ± 0.03 |
| Lobule IV | 0.71 ± 0.02 *p = 0.001 | 0.54 ± 0.04 | 0.57 ± 0.03 *p = 0.02 | 0.48 ± 0.02 | 0.60 ± 0.05 | 0.69 ± 0.05 |
| Lobule V | 1.29 ± 0.05 *p = 0.02 | 1.09 ± 0.07 | 0.92 ± 0.02 *p < 0.001 | 0.78 ± 0.03 | 1.17 ± 0.12 | 1.16 ± 0.06 |
| Lobule VI & Lobule VII | 1.64 ± 0.05 *p = 0.04 | 1.42 ± 0.10 | 1.38 ± 0.05 *p = 0.04 | 1.20 ± 0.09 | 1.70 ± 0.07 | 1.67 ± 0.05 |
| Lobule VIII | 1.08 ± 0.04 | 1.06 ± 0.04 | 0.89 ± 0.07 | 0.82 ± 0.07 | 1.24 ± 0.13 | 1.13 ± 0.09 |
| Lobule IX | 0.49 ± 0.02 | 0.40 ± 0.02 | 0.40 ± 0.04 | 0.34 ± 0.04 | 0.53 ± 0.07 | 0.46 ± 0.04 |

Figure 17:
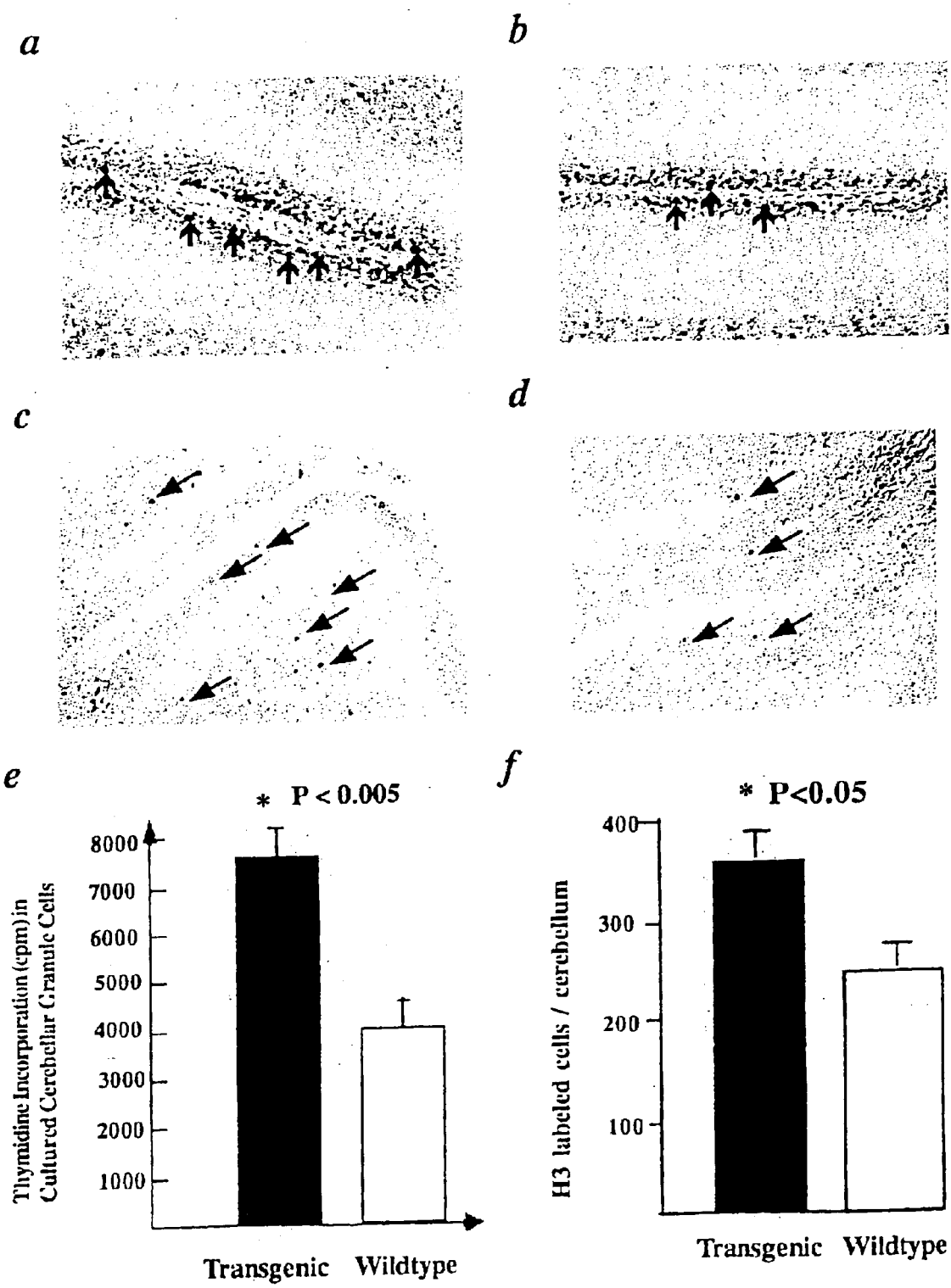
FIGS. 17a–17f contrast cell proliferation vs cell death in the BACI69tEGFP transgenic mice. Midsagittal cerebellar sections from P9 transgenic (FIG. 17a) and wildtype (FIG. 17b) mice stained with an antibody to phospho-Histone 3, a marker of mitotic cells. Cell death in transgenic (FIG. 17c) and wildtype (FIG. 17d) midsagittal cerebellar sections from P8. The arrows indicate cells positively labeled using the TUNEL method, reflecting an approximate twofold increase in cell death in the IGL.

To investigate whether the generation of more granule cells in the transgenic lines is due to an increase in granule cell proliferation, the in vitro proliferative capacity of purified P8 cerebellar granule cells from the E6 line were measured using $^3$H-thymidine incorporation assays [Gao et al., Neuron 6:705–714 (1991)]. In four independent experiments, a relative increase in $^3$H-thymidine incorporation level was seen in granule cells derived from Ru49 over-expressing mice versus those from their wildtype littermates (80% average increase, SEM 10%). A representative experiment from this series is shown in FIG. 17e. To assess the effect of Ru49 gene dosage on granule cell proliferation in vivo, the number of mitotic cells present in EGL of the cerebellum were measured (FIGS. 17a and 17b) in midline sagittal sections of P9 BAC transgenic pups versus their wild type littermates using anti-H3 antibodies [Pelletier and Sonnenberg, Nature 334:320–325 (1988)]. Cell counts revealed elevated numbers of mitotic cells in the EGL are present in the transgenic mice (359+/−34, n=5, P<0.05) compared to their wildtype littermates (253+/−34, n=6), (FIG. 17f) indicating that Ru49 also acts in vivo to increase granule cell proliferation.

Overproduction of granule cells results in increased cell death in the IGL of RU49 overexpressing mice. The increase in granule cell proliferation observed in these experiments would be expected to result in the generation of a very large excess of cerebellar granule cells in the developing animal. Since the increase in total IGL area measured in the adult BAC transgenic animals was less than twenty percent, it seemed probable that the overproduction of granule cells in the BAC transgenic animals must be partially masked by increased cell death in the cerebellum of these developing animals. To determine whether this is the case, in situ end labeling [Gavrieli et al., J. Cell Biol. 119:493–501 (1992)] was used to detect dying cells in the P8 cerebellum. As shown in FIGS. 17c and 17d, more dying cells are present in the cerebella of Ru49 over-expressing BAC transgenic mice than in their wild-type littermates, particularly in the internal granular layer. In a representative experiment, the average number of dying cells in the EGL and IGL over multiple sagittal sections is 285+/10.1, which is significantly higher (P<0.001, t-test) than that of the wildtype cerebellum (154+/−8.35). Thus, overproduction of granule cells in the transgenic strains due to elevated Ru49 gene dosage is accompanied by an increase in cell death, perhaps due to the inability of the additional granule cells to integrate properly into the developing cerebellum.

Ru49 is important for formation of intra lobular fissures in the cerebellum. Granule cell proliferation is postulated to play an important role in the formation of the cerebellar fissures and lobules [Mares and Lodin, Brain Res. 23:343–352 (1970)]. There are two types of fissures in the murine cerebellum. The major fissures that separate lobules (interlobular fissures) are invariable among the inbred mice strains, whereas the smaller intralobular fissures are both genetically variable between strains and highly heritable within an inbred strain [Inouye and Oda, J. Comp. Neurol. 190:357–362 (1980); Neumann et al., Brain Res. 524:85–89 (1990)]. Although several patterning genes, such as En-2 [Millen et al., Development 120:695–706 (1994)] and BDNF [Schwartz et al., Neuron 19:269–281 (1997)], have been shown to affect formation of the interlobular fissures, very little is known about genes that influence the formation of the intralobular fissures. The percentage of cerebella having intralobular fissures is significantly increased in both the D1 and E6 transgenic mice (FIG. 18). Thus, the Intraculminate fissure (ICF) (FIG. 16b), the Crus I fissure (CrIF) and the Crus II fissure (CrIF) (FIGS. 16d–16f) all appear at much higher frequency in animals with increased Ru49 gene dosage (FIGS. 18a–18c). In the E6 line, a significant increase in the presence of a fourth intralobular fissure, the Paramedian fissure (PMDF), was also observed (FIG. 18d). Since in the control Y7 line, the presence of these intralobular fissures is about the same in transgenic and wildtype mice, these morphological effects appear to be due to over-expression of the Ru49 gene rather than increased expression of other genes present on the BAC.

The Ru49 over-expressing mice also displayed an acceleration in the formation of intralobular fissures. For example, in the E6 line at P4.5, two out of three transgenic cerebella have the intraculminate fissure (ICF), whereas none of the wildtype littermates (n=8), nor P4.5 transgenic cerebella from the control Y7 line (n=11), have the ICF (P<0.025, $\chi^2$ analysis). These results demonstrate that Ru49 plays a critical role in the development of intralobular fissures in the cerebellum. Since no morphological differences were observed in the D1 or E6 cerebella at P0, the major action of Ru49 on cerebellar morphogenesis occurs postnatally.

Figure 19:
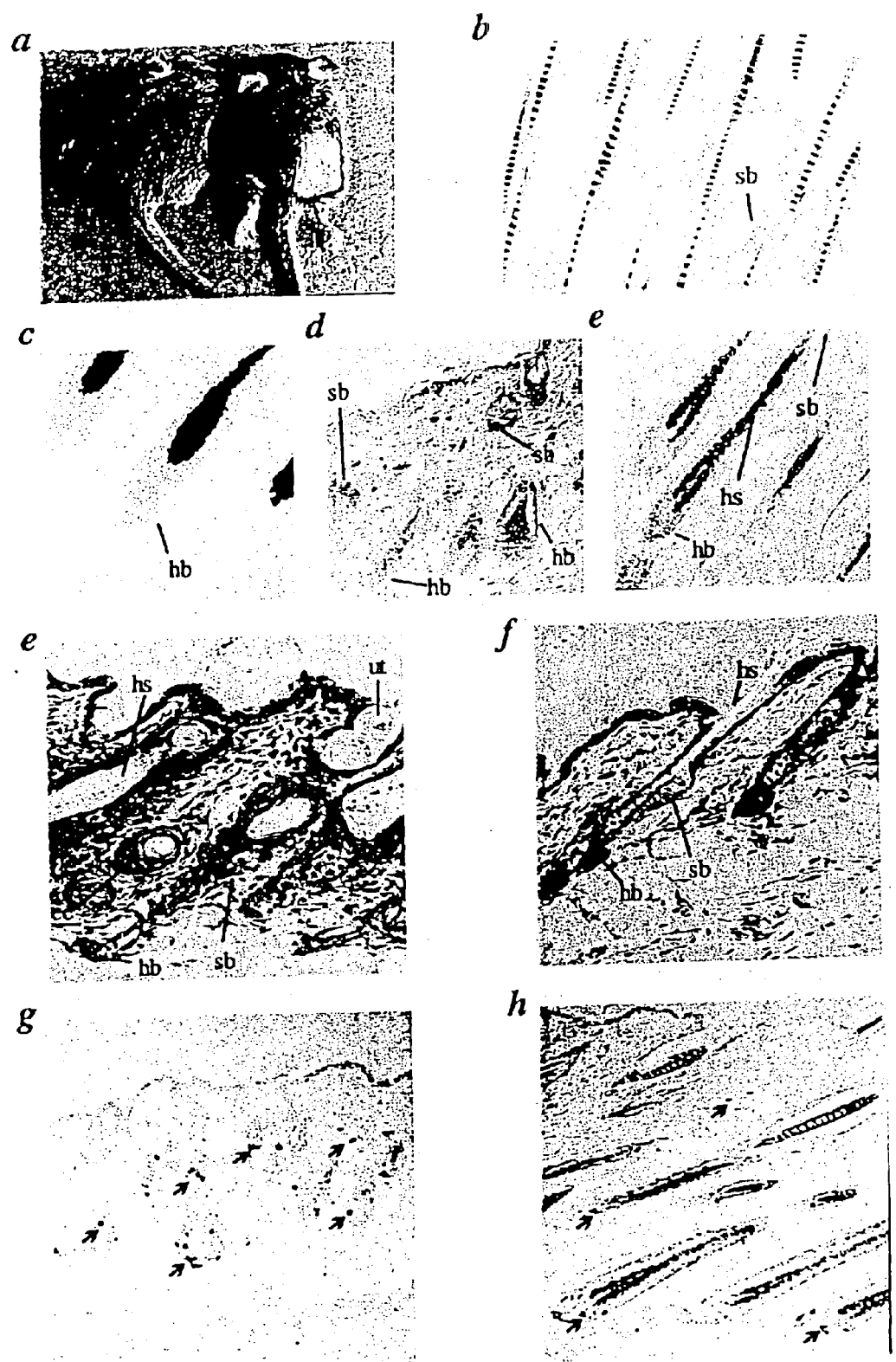
FIGS. 19a–19h show the skin phenotype of Ru49 transgenic mice versus wildtype mice.

A role for Ru49 in epidermal cell proliferation and hair follicle development: Expression of the Ru49 transgenes in mouse skin is evident from the marker gene expression patterns in the BAC169.ILPA and BAC169.tEGFP transgenic mice relative to their wild-type littermates. Examination of the lacZ expression in the Y7 line revealed cells highly expressing lacZ in the hair follicles and sebaceous glands, as well as faint general staining in other cells of the epidermis (FIGS. 19b and 19c). EGFP expression in the skin of BAC169.tEGFP transgenic mice was detected immunocytochemically, confirming the lacZ expression results and demonstrating highest levels of expression in the hair follicles and sebaceous glands (FIGS. 19d and 19e). These results agree with in situ hybridization analysis revealing Ru49 expression in the developing hair follicles of embryonic mice, and with the presence of Ru49 EST sequences in skin cDNA libraries as revealed by blast search of dbest. As in the cerebellum, no skin phenotype was observed in the Ru49 loss-of-function mutant mice. However, in a subset of Ru49 over-expressing transgenic mice, a regional alopecia phenotype was observed (FIG. 19a). This phenotype was variably penetrant. Thus, alopecia was observed in seven E6 transgenic animals, two D1 transgenic animals and eight A4 BAC transgenic animals from ~30 transgenic animals analyzed for each line. In the wildtype littermates from these lines (>100), in Y7 transgenic mice (>100), and in other animals from our colony, this pattern of hair loss was not observed. These results suggest that the skin phenotype in these animals is dependent both on the increased Ru49 gene dosage and other unknown genetic or environmental factors.

The skin of the affected transgenic animals was initially indistinguishable from their littermates. However, by P17 to P22 these mice began to lose hair progressively. The pattern of alopecia varied among the affected animals, from the flanks and lower back in mildly affected animals to substantial hair loss including the entire back, both flanks, chest and shoulders in severely affected mice (FIG. 19a). Even the most affected animals still have normal hair on the head, belly, tail and limbs. By P30, growth of new hair in the affected areas occurs in all of these animals and they suffer another cycle of hair loss at ~P50. Thereafter, the regrown hair remains relatively thin compared to wildtype littermates. The timing of the alopecia in the transgenic mice corresponds to the termination of the embryonic hair cycle (by P15) and first two postnatal hair cycles [M. H. Hardy, Trends Genet. 8:55–61; Sundberg and King, J. Invest. Dermatol. 106:368–376 (1996)]. These results are quite different in pattern and timing from the hair loss due to over-grooming that is sometimes observed in C57BL/6j and other inbred mouse lines [Sundberg and King, J. Invest. Dermatol. 106:368–376 (1996)]. Therefore, it may be concluded, that increased Ru49 gene dosage can affect hair development, but that this effect may not persist throughout life.

Histologic examination of the affected skin from P25 transgenic mice revealed a dermis with high cellularity, few normal hair follicles and frequent epithelioid cysts containing no or abnormal hair shafts. This is dramatically different from the normal cellular organization observed in wildtype littermates (FIGS. 19e and 19f). Since the morphology of some of these cysts are recognizable as aberrant hair follicles, most of the epithelioid cysts may represent altered development of the hair follicles in the first postnatal hair cycle. The density of these abnormal hair follicles (28.6+/−0.85 per 2 mm skin, n=2) is significantly higher than the density of hair follicles in wildtype littermates (1 5.9+/−2.34, n=2; P<0.05). The epidermis itself appears to be relatively unaffected in the transgenic mice. Since the expression of the lacZ marker gene is concentrated in these abnormal hair follicles and in the sebaceous gland these data suggest that elevated Ru49 protein acts intrinsically in these cells to perturb hair follicle development.

To determine whether this histologic phenotype is accompanied by changes in cell proliferation in the transgenic skin, mitotic cells were again revealed using the antibody against phosphorylated histone H3 [Juan et al., Cytometry 32:71–77 (1998)]. As shown in FIGS. 19g and 19h more mitotic cells were evident in the epithelioid cysts of the P22 Ru49 BAC transgenic animals than in the hair follicles of their wild type littermates. Thus, counting mitotic cells over multiple sections revealed 49.4+/−3.3 mitotic cells/5001 $\mu$m of skin in the transgenic mouse versus 32.4+/−2.2 in the wild type littermate (P=0.002). These results clearly document that progenitor cell proliferation is increased in the skin of the Ru49 over-expressing mice.

Discussion

The function of Ru49 in the cerebellum: The phenotypes of the BAC transgenic mice carrying increased Ru49 gene dosage strongly support a role for this transcription factor in the postnatal proliferation of cerebellar granule cells. Thus, increased Ru49 gene dosage results in more granule cells in the adult, an increase in the proliferative capacity of cultured granule cells in vitro, and elevated numbers of mitotic cells in the developing cerebellum in vivo. Consistent with the overproduction of granule cells postnatally, an increase in apoptotic cell death was observed in the developing internal granule layer, perhaps due to the failure of these cells to properly incorporate into the maturing circuitry of the cerebellar cortex.

Recent studies have provided strong evidence that the Sonic hedgehog (Shh) pathway plays a major role in regulating the proliferation of cerebellar granule cells. Thus, activation of this pathway due to mutations of the human [Vorechovsky et al., Oncogene 15:361–366 (1997)] or mouse (Goodrich et al., Science 277:1109–1113 (1997)] patched (ptc) genes can result in development of medulloblastoma. Furthermore, Shh can induce proliferation of cerebellar granule cell precursors in vitro and in situ, and production of Shh blocking antibodies in the developing cerebellum strongly inhibits the generation of granule cells in vivo [Wechsler-Reya and Scott, Neuron 22:103–114 (1999)]. These results establish Shh as a major mitogen for granule cell precursors. The effects of Ru49 on granule cell production suggest that Ru49 could participate in the response of granule cells to Shh. The simple idea that Ru49 can directly regulate the response to Shh by modulating ptc expression levels appears to be incorrect, since the expression of ptc mRNA is not altered in Ru49 overexpressing animals. However, this result does not rule out the idea that Ru49 expression or function is regulated by the Shh pathway, and that its role in the cell is to increase the proliferative response through an intrinsic cellular pathway. In this model, Ru49 is a target for the Shh pathway, and the genes regulated by Ru49 play an important role in regulating traversal through the cell cycle.

The present results also demonstrate a direct relationship between postnatal granule cell proliferative capacity and the formation of intralobular cerebellar fissures. Since the fissures formed as a consequence of increased Ru49 gene dosage also occur naturally as heritable morphological differences between inbred mouse strains [Inouye and Oda, *J. Comp. Neurol.* 190:357–362 (1980); Neumann et al., *Brain Res.* 524:85–89 (1990)], increased Ru49 expression does not alter patterning of the cerebellum. Rather, the present evidence is most consistent with the hypothesis that granule cell proliferation is required to reveal a program of pattern formation that is established early in development under the influence of many other genes [Alder et al., *Neuron* 17:389–399 (1996); Miale and Sidman, *Exp. Neurol.* 4:277–296 (1961); Fujita et al., *J. Comp. Neurol.* 128:191–208 (1966)]. As one ascends the evolutionary ladder, the numbers of lobules, sulci, folia and fissures in the cerebellar and cerebral cortices increases, and the morphology of the brain becomes highly complex. Given the recent evolutionary expansion of the zinc finger transcription factor family [Clark and Berg, *Science* 282:2018–2022 (1998); Bellefroid et al., *DNA* 8:377–387 (1989)], a role for this class of molecule in determining the morphological complexity of the vertebrate brain appears to be apparent.

A role for Ru49 in hair follicle development and epidermal cell proliferation: The present investigation of the skin in Ru49 BAC transgenic animals was prompted by the observation that both the lacZ and EGFP marker genes were expressed in the skin, which caused us to reevaluate the initial in situ hybridization analyses and to confirm that this is a site of expression for the endogenous Ru49 gene. Given the proliferative effect of Ru49 in the cerebellum, and the reports that activation of the Shh pathway in the skin can lead to basal cell carcinoma [Johnson et al., *Science* 272:1668–1671 (1996); Oro et al., *Science* 276:817–821 (1997); Xie et al., *Nature* 391:90–92 (1998)], the transient alopecia in the Ru49 over-expressing animals is very provocative. While this phenotype is variably penetrant in the transgenic lines, the increased cell proliferation, follicular density and formation of epthelioid cysts is not present in the Y7 control line or wild type littermates, documenting a significant role for Ru49 in progenitor cells of this tissue. Although the sites of enhanced cellular proliferation in the Ru49 BAC transgenic animals (epitheloid cysts) is different from the extensive hyperplasia observed in the epidermis of the Shh over-expressing mice, this might simply be due to the fact that the keratin promoter used to drive Shh expression in these animals is specific to the epidermis [Oro et al., *Science* 276:817–821 (1997)]. Thus, the present results are also consistent with a role for Ru49 and its target genes in the Shh pathway in this tissue.

Several features of the alopecia (onset, shoulder to tail progression and epithelioid cysts) observed in the Ru49 transgenic mice strongly resemble those of the mouse mutant, hairless, prompting us to consider an alternative model. Hairless mice suffer from permanent and complete alopecia due to a mutation in a different zinc finger transcription factor [Cachon-Gonzalez et al., *Proc. Natl. Acad. Sci.* 91:7717–7721 (1994)]. The Ru49 and hairless genes show no significant homology at either the DNA or protein levels. Interestingly, the hairless gene is also expressed in the cerebellar granule cells, and its expression is strongly induced by thyroid hormone [Thompson, *J. Neurosci.* 16:783240 (1996)). Thyroid hormone has been shown to influence the formation of the same cerebellar intralobular fissures affected by increased Ru49 gene dosage [Lauder et al., *Brain Res.* 76:33–40 (1974)], suggesting that Ru49 and hairless could function in the same hormonally responsive genetic pathway to regulate proliferation in the cerebellum and skin. Since the proliferation of precursor cells in vivo is probably controlled by the integration of a complex set of genetic and environmental factors, it is also possible that Ru49 operates downstream from both Shh and thyroid hormone in an intrinsic cellular pathway.

BAC transgenic mice as tools for genetic research. To study the function of Ru49 in vivo, both a traditional loss-of-function mouse mutant as well as BAC transgenic mouse lines with increased Ru49 gene dosage were generated. The loss-of-function mutant mice have no obvious phenotype in the cerebellum or other tissues. In contrast, the Ru49 BAC transgenic lines expressing increased levels of the transcription factor display several specific phenotypes that document a role for Ru49 in proliferation of granule cell precursors in the developing cerebellum, and progenitor cell division during early postnatal development of the hair follicles. From these results, it can be concluded that both that Ru49 function is redundant in the mouse, and that important insights into its function can be obtained from increased gene dosage. BAC transgenic experiments using the mouse Clock gene support this conclusion [King et al., *Cell* 89:641–653 (1989); Antoch et al., *Cell* 89:655–667 (1989)]. Thus, transgenic mice carrying BACs from the mouse Clock locus both rescue the long period and loss-of-rhythm phenotypes of the original Clock mutation, and shorten the circadian period on the wild type background [Antoch et al., *Cell* 89:655–667 (1989)]. An important distinction between these two studies is that the present study of Ru49 was conducted to uncover a biochemical function for a gene that is functionally redundant and displays no obvious null phenotype, whereas the Clock studies were performed to "clone by rescue" a mutant circadian phenotype.

Several considerations indicate that the approach disclosed herein may yield important information for many genes. First, the average mouse gene is between 30–40 kb. Thus, BACs often contain all the information necessary for correct copy number-dependent and position-independent transcription in transgenic mice [Example 1 above; Yang et al., *Nat. Biotech.* 15:859–865 (1997)]. For most genes, this ensures that the phenotypes observed reflect increased dosage in the proper cell types in vivo and reproducible results in different transgenic lines carrying equivalent copy numbers. Second, the ability to construct precisely modified BACs by homologous recombination in *E. coli* [Example 1 above; Yang et al., *Nat. Biotech.* 15:859–865 (1997)] allows the insertion of marker genes to rapidly confirm that transgene expression reflects the endogenous locus, and to prepare appropriate controls for dosage of other genes that might be carried on these large genomic fragments. Third, while it has been demonstrated that duplication or triplication of most loci in *D. melanogaster* does not result in an overt phenotype [Painter and Muller, *Genes Dev.* 1:913–923 (1929)], genetic analysis using high level expression via P-element insertion, heat shock promoters and the GAL4 UAS system has revealed relevant functions for many fly gene products [P.A. Rørth, *Natl. Acad. Sci.* 93:12418–12422 (1996); Perrimon, *Proc. Natl. Acad. Sci.* 95:9716–9717 (1998); Rørth, *Development* 125:1049–1057 (1998)]. Similar results have been obtained in *C. elegans* (Jansen et al., *Nat. Genet.* 28:414–419 (1999)]. Thus, dosage experiments for the large family of worm G-protein coupled receptors revealed functions for several members of this family that did not display an informative phenotype using loss-of-function analysis. Based on these results, and given the small fraction of genes that yield an apparent loss-of-function phenotype [Miklos and Rubin, Cell 86:521–529 (1996)], BAC mediated gene dosage analysis provides an important new tool for functional analysis of mammalian genes.

EXAMPLE 3

Rapid Modification and High Throughput Resolution of Bacterial Artificial Chromosomes in Liquid Introduction Traditionally, overexpression of cDNA in eukaryotic cells and transgenic mice has been widely used for the study of gene function and regulation. However, the cDNA itself is often missing important elements for regulation of gene activity, such as high-level, tissue-specific, and integration site-independent expression of the transgene. Those elements such as enhancers, locus control regions (LCR), and insulators, may reside at a large distance (>50 kb) from the gene itself. A intact genomic loci as a transgene will be essential for this expression. Bacterial artificial chromosome (BACs) and P-1 derived artificial chromosomes (PACs) have become a widespread and powerful resource in manipulating the large genomic DNA in E. coli. However, although BAC transgenic technology has been used for studying gene function and regulation, the efficiency for modifying and resolving these BACs can be improved.

Results

In order to increase the efficiency of the cointegration and resolution, a strategy has been developed that allows for liquid modification, and high throughput. This method employs specific elements that are constructed in a BAC shuttle vector. First, a R6Kγ DNA replication origin which requires the expression of the pir protein is included to allow selective reproduction dilution of the shuttle vector depending on the strain of bacteria containing the shuttle vector. Second, a gene encoding a recombination protein, e.g., rec A, is employed to transiently allow homologous recombination. The shuttle vector also comprises a specific drug resistant gene, e.g., Ala, (the BAC contains a chloramphenicol-resistant gene). Third, the shuttle vector includes a positive counterselection marker, e.g., the SacB gene. Fourth, the shuttle vector also comprises a marker gene, e.g., IRESEGFP that is adjacent to the A box, (homology region) thereby enabling the detection of the gene product of the gene of interest comprised in the BAC when it is expressed. Fifth, AscI and SmaI sites are introduced into the shuttle vector surrounding the A box. In one particular embodiment exemplified herein, the shuttle vector also comprises two FRT sites (see FIG. 20). In a second embodiment, the shuttle vector has two copies of the IRES EGFP marker that bracket the desired insert (see FIG. 23) rather than the two FRT sites (see FIG. 23).

The replication origin for this vector (R6Kγ) allows growth at a high copy number in strains containing the pir gene, but it cannot replicate in DH10B, the host for the BACs [Metcalf et al., Plasmid 35:1–13 (1996)]. This is advantageous both because it is very simple to obtain large amounts of DNA for cloning into this vector, and because the plasmid cannot persist on its own in the BAC strain. The Asc1 and Sma1 sites and corresponding restriction enzymes are used because they allow the preparation of the shuttle vector for directional cloning of the "A box" with very little background due to failure of the recircularization of the vector. Following ligation, approximately 50% of the colonies plated contained the PCR amplified insert when this vector was used. Finally, the SacB gene is added to the vector because it is a powerful negative selectable marker for use in subsequent steps of the modification protocol.

A protocol for cloning of the shuttle vectors for each BAC is as follows:

1. 100 ug (enough for 1000 ligation reactions) of the Asc/Sma1 digested shuttle vector are prepared by incubation overnight in appropriate amounts of the restriction enzymes. The digested vector is purified from small fragments by gel filtration using DNA fragment purification columns (e.g., GENECLEAN spin columns, Bio101, Inc.). Aliquots are tested to determine the background of undigested or single digested shuttle vector. If background undigested or single digested shuttle vector is observed, the shuttle vector is re-digested until the background disappears. This stock of predigested vector is aliquoted and stored for use in "A box" cloning.
2. Homology regions from a gene of interest from C57b1/6 J genomic DNA, for example, is amplified by PCR using primers to the 3'UTRs of the gene of interest (using a 5'primer to incorporate the ASC1 site). The products are digested overnight with Asc1, and the digested fragments are purified by gel electrophoresis in low melting point agarose (one gel per week for at least twenty amplified fragments).
3. The agarose is melted and the digested shuttle vector (100 ng) from step (1) above, are ligated with the purified fragments (25 ng) from step (2), transformed and plated on LB amp plates. The ligation occurs between the "A" box of the shuttle vector and the PCR fragments from the genomic DNA.
4. A few colonies (e.g., 4) per ligation are picked individually and tested for correct insertion by PCR using a 5' end primer spanning from the shuttle vector to the gene specific 3' end primer used to amplify the "A box".
5. DNA minipreps are then prepared for positive shuttle vectors for each gene for use in modification. The shuttle vectors now contain the nucleic acid fragment in the "A" box that is to be inserted into the gene of interest of the BAC.

Figure 21:
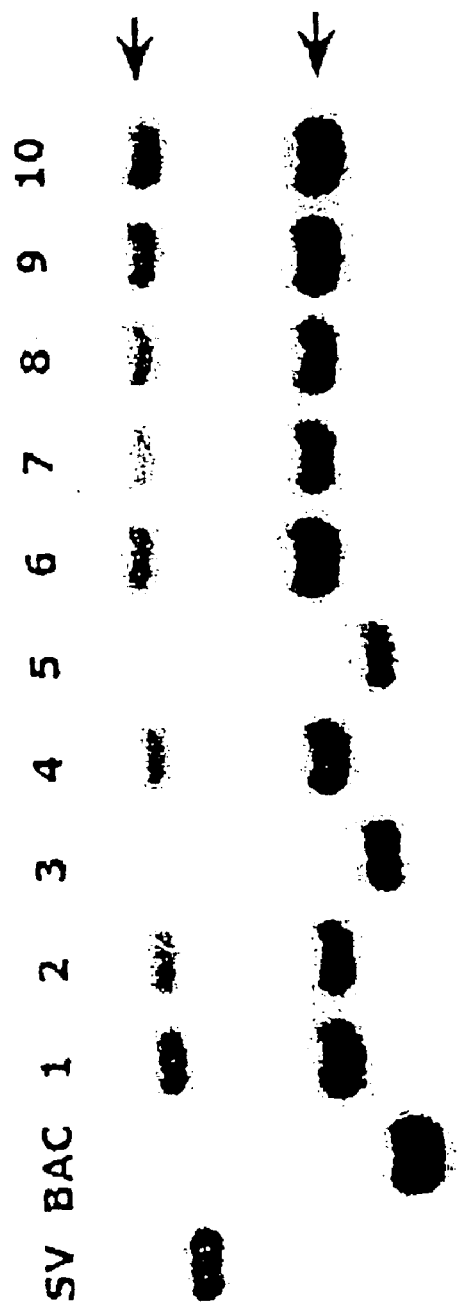
FIG. 21 depicts a Southern blot demonstrating the efficacy of performing transient homologous recombination to modify a BAC using the vector of FIG. 20. Eight of the ten colonies picked for analysis contained the desired product.

The use of the R6Kγ origin of replication has dramatically improved the efficiency of this step of the BAC modification procedure to close to 100%. This is an important improvement that significantly alters the amount of work required for preparation of the modified BACs. In other protocols, large numbers of colonies (>20) had to be screened at this step of the protocol in order to identify a proper cointegrate because the temperature sensitive origin comprised by the shuttle vector did not always strongly select against free shuttle vector in the BAC strain. The fact that the new shuttle vector absolutely cannot replicate in the BAC strain (DH10B) means that selection for both the chloramphenicol marker on the BAC and the ampicillin marker on the shuttle vector yields only those colonies in which the shuttle vector has integrated into the BAC or the E. coli genome (outside of the background discussed above). Furthermore, all of the selections can be done in liquid culture simply by serial dilution. A Southern blot demonstrating the efficacy of this procedure is shown in FIG. 21. In this case, eight of the ten colonies picked for analysis (i.e., 80%) contained the desired product.-

A protocol for preparation of the cointegrates is as follows:
1. The PLD55-modified shuttle vector containing a selected nucleic acid sequence, i.e., an homology region, for the gene of interest which is contained by a BAC is transformed into BAC competent cells by electroporation. 40 ul of competent cells containing the BAC are thawed on ice, and then mixed with 2 $\mu$l of DNA(0.5 $\mu$g/$\mu$l). The mixture is then placed on ice for 1 minute. Each sample is then transferred to a cold 0.1 cm cuvette. A Gene Pulser apparatus is used to carry out the electroporation. The Gene Pulser apparatus is set at 25 $\mu$F, the voltage to 1.8 KV and pulse controller to 200 $\Omega$.
2. 1 ml of SOC media is added to each cuvette right after the electroporation. The cells are resuspended and the cell suspension is transferred to a 17×100 mm polypropylene tube. The tube is then incubated at 37° C. for one hour with shaking at 225 RPM.
3. The transformed cells are select with 5 ml of LB supplemented with chloramphenicol (12.5 $\mu$g/$\mu$l) and ampicillin (25 $\mu$g/ml), and then incubated at 37° C. overnight.
4. The overnight culture is diluted 1 to 1000 and grown in 5 ml of LB with chloramphenicol (12.5 $\mu$g/ml) and ampicillin (50 $\mu$g/ml)at 37° C. for about six hours. This culture is diluted 1 to 5000 and grown in the same media at 37° C. for about 4 to 5 hours. A series of dilutions are made, and they are placed on Amp plates, incubated at 37° C. overnight.
5. Three picks from each colony are made per plate, inoculated with 5 ml of LB supplemented with 100 $\mu$g/ml Ampicillin, and grown overnight at 37° C. Miniprep DNA is prepared from 3 ml cultures by the alkaline lysis method. Proper cointegrates are identified for each clone using appropriate primers for PCR amplification to detect the presence of the cointegrate.

To improve the efficiency for removal of the shuttle vector from the cointegrates to generate the modified BACs two different strategies have been used. The first involves excision by flip recombinase. This procedure expresses flp recombinase within the cointegrate containing cells to excise the shuttle vector sequences [Hoang et al., Gene 212:77–86 (1998)]. The flp recombinase works via the "frt" sites surrounding the shuttle vector and it is highly efficient for excision (see FIG. 20). By adopting this strategy for the final step of BAC modification, 20% efficiency has been achieved.

A protocol for this procedure is as follows:
1. Each individual bacterial colony containing the cointegrate is grown in 1 ml of LB supplemented with chloramphenicol (12.5 ug/ml) until the $OD_{600}$ is about 0.6.
2. The cells are spun down at 3000 rpm and each sample is resuspended with 100 mM $CaCl_2$. The cells are transformed with a plasmid containing the AraBADflp, a kanamycin resistant gene and a temperature sensitive origin. The cells are then grown on Kana/Chl plates at 30° C. overnight to select for transformants containing the Flp recombinase plasmid.
3. The colonies (e.g., 3) picked up are placed in 3 ml of LB supplemented with Kanamycin and Chloramphenicol, and grown until an $OD_{600}$ of about 0.5 is observed. Flp recombinase is induced with arabinose for three hours.
4. Excision is selected for by growth on sucrose plates at 43° C. overnight. This also cures the Flp expressing plasmid because of its temperature sensitive origin of replication.
5. The loss of vector sequences are screened by PCR.
6. DNA is prepared from a 10 ml culture (40 total), and the location of the gene within the BAC is mapped by digestion with Asc1 and Not1. Pulsed field gel electrophoresis is used to detect the introduced Asc1 site relative to the ends of the genomic DNA insert (Not I sites).
7. Preferred BAC construct DNA is selected, and when desired, prepared for transgenic injection.

Preferably, efficiencies of excision of the vector sequences from the cointegrates are comparable to the published data (about 90%) are obtained [Hoang et al., Gene 212:77–86 (1998)]. A schematic drawing depicting this procedure, culminating in using the modified BAC to make transgenic mice is shown in FIG. 22.

Figure 24:
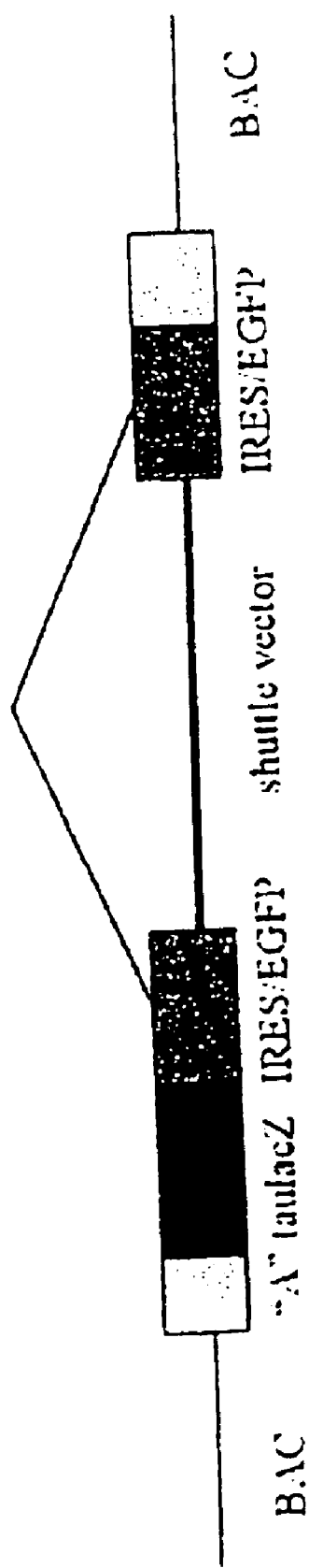
FIG. 24 depicts the conintegrate of the shuttle vector of FIG. 23 and the BAC.

An alternative method for this step of the modification utilizes the same homologous recombination event to form the cointegrate, but a second homologous recombination event to resolve out the vector sequences. In this case, the shuttle vector has two copies of the IRES EGFP marker that bracket the desired insert (see FIG. 23) rather than the two FRT sites. When this shuttle vector integrates into the BAC, it produces a cointegrate that is depicted in FIG. 24.

Figure 25:
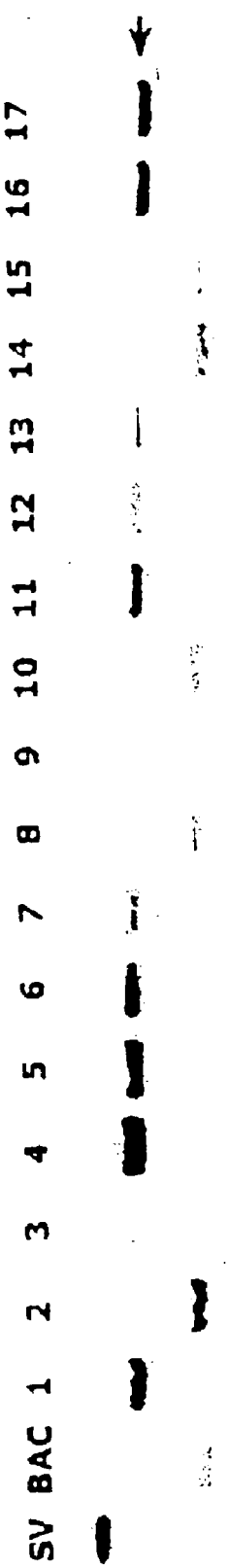
FIG. 25 depicts a Southern blot monitoring the final resolution step using the conditional replication shuttle vector of FIG. 23. 11 of 17 colonies tested yielded the desired product (arrow,), 5 others have correctly resolved cointegrates that resolved back through the "A box" to give the original unmodified BAC. No DNA was recovered in the final sample (lane 9).

Since the duplicated EGFP is not homologous to the BAC, the cointegrate always forms through the "A box", again with close to 100% efficiency. However, the two copies of the EGFP now flank the shuttle vector and these can be used for homologous recombination to resolve the cointegrate to get rid of the shuttle vector. Since the EGFP is much larger than the A box homology region that was used for cointegration, the resolution step occurs with much greater frequency through the EGFP sequences. If the negative selection for SacB is sufficiently strong, the percentage of correctly resolved modified BACs should be comparable to those seen with the Flp/FRT system. This system has been tested yielding 80% correct cointegration events and 100% correct resolution of those cointegrated plasmids. In the resolution step shown, 11 of 17 colonies tested yielded the desired product (arrow, FIG. 25), 5 others represented correctly resolved cointegrates that resolved back through the "A box" to give the original unmodified BAC, and one appeared to be a failed miniprep in which no DNA was recovered (lane 9).

A protocol for this procedure is as follows:
11. Each colony of cointegrate is picked up from the Amp plates. Each colony is then inoculated with 5 ml of LB supplemented with chloramphenicol(12.5 $\mu$g/ml) and 6% sucrose and then incubated at 37° C. for eight hours.
2. The culture is next diluted 1 to 5000 and then plated on the agar plate with chloramphenicol(12.5 $\mu$g/ml) and 6% sucrose, and incubated at 37° C. overnight.
3. Five colonies per plate are picked up and inoculated with 5 ml of LB supplemented with chloramphenicol (12.5 $\mu$g/ml) only and incubated at 37° C. overnight. Miniprep DNA is prepared from those cultures by the alkaline lysis method. The resolved BACs are screened by PCR using the 5' EGFP primer and 3' primer downstream of the A box.

One advantage of this system over the Flp/FRT system is that there is no need to transform with a second plasmid to express the Flp recombinase. In this case, therefore, the entire procedure could be accomplished by serial dilution into different selective media in liquid culture and a single step of plating onto sucrose.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

---

What is claimed is:

1. A method of selectively performing homologous recombination with a particular nucleotide sequence of a Bacterial or Bacteriophage-Derived Artificial Chromosome (BBPAC) that is contained in a recombination deficient host cell comprising introducing a conditional replication shuttle vector into a recombination deficient host cell and therein enabling homologous recombination in the host cell via the transient expression of a recombination protein in the host cell;

wherein the host cell comprises a Bacterial or Bacteriophage-Derived Artificial Chromosome (BBPAC) which contains the particular nucleotide sequence; wherein the conditional replication shuttle vector encodes a recombination protein that is transiently expressed by the host cell; wherein the conditional replication shuttle vector contains homologous nucleic acid sequences capable of selectively integrating into the particular nucleotide sequence when the recombination protein is expressed; and wherein the expressed recombination protein effectuates recombination of the shuttle vector and the Bacterial or Bacteriophage-Derived Artificial Chromosome (BBPAC).

2. A method of selectively modifying a particular nucleotide sequence of a Bacterial or Bacteriophage-Derived Artificial Chromosome (BBPAC) that is contained in a recombination deficient host cell comprising:

(a) introducing a conditional replication shuttle vector into a recombination deficient host cell; wherein the host cell comprises a Bacterial or Bacteriophage-Derived Artificial Chromosome (BBPAC) that comprises a gene of interest which contains the particular nucleotide sequence; wherein the conditional replication shuttle vector encodes a recombination protein that is expressed by the host cell and permits homologous recombination to occur in the host cell; wherein the conditional replication shuttle vector contains homologous nucleic acid sequences capable of selectively integrating into the particular nucleotide sequence when the recombination protein is expressed forming a co-integrate; wherein the nucleic acid sequences that selectively integrate into the particular nucleotide sequence and the nucleic acid encoding the recombination protein are positioned on the conditional replication shuttle vector such that upon resolution of the co-integrate, the nucleic acid encoding the recombination protein remains with the conditional replication shuttle vector; and wherein the expressed recombination protein effectuates recombination of the shuttle vector and the Bacterial or Bacteriophage-Derived Artificial Chromosome (BBPAC); and (b) growing the host cell under conditions in which the conditional replication shuttle vector cannot replicate, therein diluting out the conditional replication shuttle vector encoding the recombination protein, and thereby preventing further recombination events in the recombination deficient cells.

3. The method of claim 2 wherein the conditional replication shuttle vector further comprises a nucleic acid that encodes a marker protein or peptide and wherein the nucleic acid that selectively integrates into the particular nucleotide sequence and the nucleic acid encoding the marker protein or peptide are positioned on the conditional replication shuttle vector such that upon resolution of the co-integrate, the nucleic acid encoding the marker protein or peptide is inserted into or adjacent to the particular nucleotide sequence.

4. The method of claim 2 wherein the conditional replication shuttle vector cannot replicate in the host cell because the conditional replication shuttle vector requires a particular protein for replication and neither the host cell nor the Bacterial or Bacteriophage-Derived Artificial Chromosome (BBPAC) encode the particular protein.

5. The method of claim 2 wherein the BBPAC is a BAC or a PAC.

6. The method of claim 5 wherein the conditional replication shuttle vector cannot replicate in the host cell because the conditional replication shuttle vector comprises a R6K origin of replication and neither the host cell nor the BAC encode pir.

7. The method of claim 6 wherein the conditional replication shuttle vector further comprises a first frt site that is positioned on one side of the nucleic acid that selectively integrates into the particular nucleotide sequence, and a second frt site that is positioned on the other side of the nucleic acid that selectively integrates into the particular nucleotide sequence and wherein the resolution of the co-integrate is performed by adding flp recombinase to the host cell.

8. The method of claim 6 wherein the conditional replication shuttle vector further comprises a nucleic acid encoding a marker protein or peptide that is positioned in between the two frt sites and is also adjacent to the nucleic acid that selectively integrates into the particular nucleotide sequence such that after the resolution, the marker protein or peptide is contained by the BAC.

9. The method of claim 7 wherein flp recombinase is added to the host cell by introducing a plasmid that encodes flp recombinase to the host cell.

10. The method of claim 9 wherein the plasmid contains a conditional origin of replication.

11. The method of claim 6 wherein the conditional replication shuttle vector further comprises two homologous nucleotide sequences that are homologous to each other but are not homologous to the BAC; wherein the two homologous nucleotide sequences are positioned on the conditional replication shuttle vector to be on opposite sides of the nucleic acid that selectively integrates into the particular nucleotide sequence; and wherein the resolution of the co-integrate is performed by a recombination event between the two homologous nucleotide sequences.

12. The method of claim 6 wherein the recombination deficient host cell cannot independently support homologous recombination because the host cell is RecA⁻.

13. The method of claim 6 further comprising adding a counterselection agent after the resolution of the co-integrate to remove host cells that comprise the conditional replication shuttle vector; wherein the conditional replication shuttle vector further comprises a counterselection gene that is positioned on the conditional replication shuttle vector such that upon resolution of the co-integrate the counterselection gene remains with the conditional replication shuttle vector.

14. The method of claim 13 wherein the counterselection agent is sucrose and the counterselection gene is SacB.

15. The method of claim 14 wherein the recombination deficient host cell cannot independently support homologous recombination because the host cell is RecA⁻.

16. The method of claim 15 wherein the recombination protein is selected from the group consisting of recA, the rec E and rec T protein pair, the Lambda beta protein, and the *Arabidopsis thaliana* DRT100 gene product.

17. The method of claim 2, wherein said BBPAC is modified after resolution to result in nucleic acids insertions, and/or nucleic acids deletions, and/or point mutations on the BBPAC.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: PCR primer

<400> SEQUENCE: 1
aaagtcctgc tggctcggga atc    23

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gcctcctctg catttcaggg    20